(12) United States Patent
Anthamatten et al.

(10) Patent No.: US 8,172,873 B2
(45) Date of Patent: May 8, 2012

(54) SHAPE MEMORY POLYMERS

(75) Inventors: Mitchell L. Anthamatten, Rochester, NY (US); Jiahui Li, Rochester, NY (US); Christopher L. Lewis, Rochester, NY (US)

(73) Assignee: University of Rochester, Rochester, NY (US)

( * ) Notice: Subject to any disclaimer, the term of this patent is extended or adjusted under 35 U.S.C. 154(b) by 0 days.

(21) Appl. No.: 13/047,354

(22) Filed: Mar. 14, 2011

(65) Prior Publication Data

US 2011/0251364 A1 Oct. 13, 2011

Related U.S. Application Data

(63) Continuation-in-part of application No. 11/820,693, filed on Jun. 20, 2007, now Pat. No. 7,935,131, application No. 13/047,354.

(60) Provisional application No. 61/313,712, filed on Mar. 13, 2010, provisional application No. 60/854,249, filed on Oct. 25, 2006.

(51) Int. Cl.
*A61B 17/04* (2006.01)
*C08F 26/06* (2006.01)

(52) U.S. Cl. ....... 606/231; 606/151; 623/1.15; 128/864; 526/302; 526/312; 526/263; 526/264

(58) Field of Classification Search .................. 606/231, 606/151; 623/1.15; 128/864; 526/302, 312, 526/263, 264

See application file for complete search history.

(56) References Cited

U.S. PATENT DOCUMENTS

| 6,538,089 B1 | 3/2003 | Samra et al. |
| 2005/0017396 A1 | 1/2005 | Pearce et al. |

FOREIGN PATENT DOCUMENTS

| WO | 03093341 A1 | 11/2003 |
| WO | 2004016598 A1 | 2/2004 |

OTHER PUBLICATIONS

Yamauchi et al.; Thermoreversible Poly(alkyl acrylates) Consisting of Self-Complementary Multiple Hydrogen Bonding; Macromolecules, 2003, vol. 36; pp. 1083-1088; XP-002260387.
Ahir et al.; Self-Assembled Shape-Memory Fibers of Triblock Liquid-Crystal Polymers; Advanced Functional Materials, 2000; pp. 1-6.
Brunsveld et al.; Supramolecular Polymers; Chemical Reviews, 2001, vol. 101; pp. 4071-4097.
Cao et al.; Hydrogen-bonded polymer network—poly(ethylene glycol) complexes with shape memory effect; Journal Mater. Chem., 2002, vol. 12; pp. 2957-2960.
Cates; Nonlinear Viscoelasticity of Wormlike Micelles (and Other Reversibly Breakable Polymers); Journal of Phys. Chem., 1990, vol. 94; pp. 371-375.
Cates; Reptation of Living Polymers: Dynamics of Entangled Polymers in the Presence of Reversible Chain-Scission Reactions; Macromolecules, 1987, vol. 20; pp. 2289-2296.
Chino et al.; Themoreversible Cross-Linking Rubber Using Supramolecular Hydrogen-Bonding Networks; Macromolecules, 2001, vol. 34; pp. 9201-9204.
Diab et al.; Polymer Complexes: Part VIII—Thermal Stability of Poly(2-Acrylamidopyridine) and Polymer Complexes of 2-Acrylamidopyridine with Some Transition Metal Chlorides; Polymer Degradation and Stability, 1989, vol. 24; pp. 51-58.
Farnik et al.; Synthesis and Self Assembly of Hydrogen-Bonded Supramolecular Polymers; Macromol. Symp., 2004, vol. 217; pp. 247-266.
Hirschberg et al.; Supramolecular Polymers from Linear Telechelic Siloxanes with Quadruple-Hydrogen-Bonded Units; Macromolecules, 1999, vol. 32; pp. 2696-2705.
IRIE; Chapter 9: Shape memory polymers; Otsuka and Wayman eds.; Shape Memory Materials, 1998; Cambridge University Press; pp. 203-219.
Jeong et al.; Shape memory polyurethane containing amorphous reversible phase; Journal of Materials Science, 2000, vol. 35; pp. 1579-1583.
Jiang et al.; Polymers Move in Response to Light; Advanced Materials, 2006, vol. 18, No. 11; pp. 1471-1475.
Kim et al.; Polyurethanes having shape memory effects; Polymer, 1996, vol. 37; No. 26; pp. 5781-5793.
Lendlein et al.; Biodegradable, Elastic Shape-Memory Polymers for Potential Biomedical Applications; Science, 2002, vol. 296; pp. 1673-1676.
Lendlein et al.; Shape-Memory Polymer Networks from Oligo (ε-caprolactone)Dimethacrylates; Journal of Polymer Science: Part A: Polymer Chemistry, 2005, vol. 43; pp. 1369-1381.
Lendlein et al.; Light-induced shape-memory polymers; Nature, 2005, vol. 434; pp. 879-882.
Lin et al.; Study on Shape-Memory Behavior of Polyether-Based Polyurethanes. I. Influence of the Hard-Segment Content; Journal of Applied Polymer Science, 1998, vol. 69; pp. 1563-1574.
Liu et al.; Shape Memory of Hydrogen-Bonded Polymer Network/ Poly(ethylene glycol) Complexes; Macromolecules, 2004, vol. 37; pp. 2228-2232.
Liu et al.; Chemically Cross-Linked Polycyclooctene: Synthesis, Characterization, and Shape Memory Behavior; Macromolecules, 2002, vol. 35; pp. 9868-9874.
Rabani et al.; Synthesis and characterization of two shape-memory polymers containing short aramid hard segments and poly(ε-caprolactone) soft segments; Polymer, 2006, vol. 47; pp. 4251-4260.
Sakurai et al.; Crystal transformation of styrene-butadiene block copolymer; Polymer, Sep. 1994, vol. 35; pp. 4238-4239.
Sherrington et al.; Self-assembly in synthetic macromolecular systems via multiple hydrogen bonding interactions; Chem. Soc. Rev., 2001, vol. 30; pp. 83-93.
Sijbesma et al.; Reversible Polymers Formed from Self-Complementary Monomers Using Quadruple Hydrogen Bonding; Science, 1997, vol. 278; pp. 1601-1604.
Sivakova et al.; Utilization of a Combination of Weak Hydrogen-Bonding Interactions and Phase Segregation to Yield Highly Thermosensitive Supramolecular Polymers; J. Am. Chem. Soc., 2005, vol. 127; pp. 18202-18211.

(Continued)

*Primary Examiner* — Robert D. Harlan
(74) *Attorney, Agent, or Firm* — Hodgson Russ LLP

(57) ABSTRACT

The present disclosure relates to Shape Memory Polymers (SMP's) comprising function groups that allow the polymers to be elastically deformed, utilized in the elastically deformed state, and subsequently returned to the original polymorphic shape.

19 Claims, 20 Drawing Sheets

OTHER PUBLICATIONS

Sontjens et al.; Stability and Lifetime of Quadruply Hydrogen Bonded 2-Ureido-4[1H]-pyrimidinone Dimers; J. Am. Chem. Soc., 2000, vol. 122; pp. 7487-7493.

Suzuki et al.; Supramolecular Crosslinked Linear Poly(Trimethylene Iminium Trifluorosulfonimide) Advanced Materials, 2006, vol. 18; pp. 1043-1046.

Tobushi et al.; Thermomechanical properties in a thin film of shape memory polymer of polyurethane series; Smart Mater. Struct., 1996, vol. 5; pp. 483-491.

Toensmeier; Compounders Thwart Counterfeiting With Covert Additive Techniques; Plastics Engineering, 2005; pp. 10-11.

Wubbenhorst et al.; Complex Dynamics of Hydrogen Bonded Self-assembling Polymers; IEEE Transactions on Dielectrics and Electrical Insulation, Jun. 2001, vol. 8, No. 3; pp. 365-372.

Xu et al.; Synthesis and shape memory effects of Si-O-Si cross-linked hybrid polyurethanes; Polymer, 2006, vol. 47; pp. 457-465.

Zheng et al.; Shape memory properties of poly(D,L-lactide)/hydroxyapatite composites; Biomaterials, 2006, vol. 27; pp. 4288-4295.

Diab et al.; Polymer Complexes: Part VI—Thermal Stability of Poly(2-Acrylamidophenol) Homopolymer and Complexes of Poly(2-Acrylamidophenol) with Some Transition Metal Salts; Polymer Degradation and Stability, 1988, vol. 23; pp. 83-90.

Cate et al.; Enantioselective Cyclization of Racemic Supramolecular Polymers; Journal of American Chemical Society, vol. 125, 2003; pp. 6860-6861.

Geurts et al.; Syntheses of New Amino-Functionalized Methacrylates and Their Use in Free Radical Polymerizations; Journal of Applied Polymer Science, vol. 80, 2001; pp. 1401-1415.

Lendlein et al.; Shape Memory Polymers; Angew. Chem. Int. Ed., vol. 41, 2002; pp. 2035-2057.

Yamauchi et al.; Thermoreversible Poly(alkyl acrylates) Consisting of Self-Complementary Multiple Hydrogen Bonding; Macromolecules, vol. 36, 2003; pp. 1083-1088.

% UPy = polymers formed from reactions wherein 1 and 2 mole % of Hydrogen Bonding monomers having the R⁴ unit with the formula:

were employed as starting materials.

SHAPE MEMORY POLYMERS

CROSS-REFERENCE TO RELATED APPLICATIONS

This application is a continuation-in-part of U.S. patent application Ser. No. 11/820,693, filed Jun. 20, 2007, now U.S. Pat. No. 7,935,131 which claims priority to U.S. provisional patent application no. 60/854,249, filed Oct. 25, 2006, the disclosures of which are incorporated herein by reference. This application also claims priority to U.S. provisional patent application No. 61/313,712, filed Mar. 13, 2010, the disclosure of which is incorporated herein by reference.

STATEMENT REGARDING FEDERALLY SPONSORED RESEARCH

This invention was made with government support under contract no. DMR-0906627 awarded by the National Science Foundation. The government has certain rights in the invention.

FIELD OF THE INVENTION

The present invention generally relates to Shape Memory Polymers (SMP's). More particularly, the present invention relates to Shape Memory Polymers (SMP's) that have surprising properties. The polymers can be elastically deformed, utilized in the elastically deformed state, and subsequently returned to the original polymorphic shape.

BACKGROUND OF THE INVENTION

Most materials behave elastically at low levels of strain. For crystalline solids and amorphous glasses, elasticity occurs up to a strain limit rarely exceeding 1%. Elastic strain is related to the extent to that atoms are dislodged from their equilibrium positions. However, elasticity in polymers is very different, and polymeric materials can exhibit elastic behavior to several hundred percent strain. Polymeric elastomers are usually high molecular weight molecules, well above their glass transition temperature, $T_G$, and they typically contain a network of chemical or physical crosslinks that act as permanent entanglements and restrict long range (irreversible) slippage of chains. When a polymer elastomer is stretched, a restoring force arises because molecular chains are distorted from their most probable and preferable configuration—this phenomenon is known as entropic elasticity. Several classes of polymers exhibit entropic elasticity, including natural and synthetic rubbers and polyurethanes.

Entropy-based elasticity must be differentiated from the so called "shape-memory effect" defined by the literature. A shape-memory material is one that returns to its original shape only after the application of an external stimulus (Irie, "Shape Memory Materials." Chapter 9: "Shape Memory Polymers" Otsuka and Wayman eds. Campbridge University Press, 1998). For example, a thermo-responsive shape-memory material returns to its "remembered" shape only upon heating past a critical shape-memory temperature $T_{SM}$. Above $T_{SM}$ such a material can be elastically deformed by subjecting it to external stresses, and then cooling it (while under stress) beneath $T_{SM}$. In the cooled state, external stresses can be removed and the material retains its deformed shape. Upon subsequent heating above $T_{SM}$, the material recovers its elastic strain energy and returns to its original shape. Metallic alloys and ceramics are well-known to exhibit this shape-memory effect. Shape-memory polymers (SMP's) are noted for their ability to recover extremely large strains—up to several hundred percent—that are imposed by mechanical loading. The large-strain recovery observed in SMP's is a manifestation of entropy elasticity.

SMP's offer tremendous advantages to the fields of biotechnology and medicine (Lindlein et al., "Shape Memory Polymers" Angew, Chem. Int. Ed. 41, p 2034 (2002)). By exploiting the large-strain recovery of SMP's, surgeons can implant bulky objects into the body through small incisions. Biodegradable SMP's enable the development of degradable sutures and vascular stents. Biological MicroElectroMechanic Systems (Bio-MEMS) can perform intricate gripping, releasing, or even stitching operations. SMP's can also be used in non-biological applications including rewritable storage media, intelligent packaging materials, shapeable tools, and deployable objects for space exploration. SMP's can also be used in the development of recyclable thermosets and materials processing.

BRIEF SUMMARY OF THE INVENTION

In the present invention it was surprisingly discovered that incorporation of certain functional groups into polymer backbones affords these polymers the ability to conserve, or mechanically stabilize elastically deformed states of strain in polymeric materials.

The present disclosure relates to shape memory polymers having the formula:

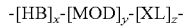

comprising:
i) hydrogen bonding units, HB, having at least one hydrogen bond donor moiety and at least one hydrogen bond acceptor moiety;
ii) backbone modifier units, MOD; and
iii) crosslinking units, XL, that are capable of forming one or more irreversible crosslinks;

the index x is from about 0.5 to about 20, the index y is from about 75 to about 99.6, and the index z is from about 0.1 to about 5; wherein the polymer is characterized by having a shape memory temperature, $T_{SM}$, such that the polymer can be elastically deformed at the shape memory temperature, and subsequently lowered to a shape memory temperature, $T_F$, and the method of elastic deformation is removed, the polymer will return to its with a rate slower than the rate observed if the method of mechanical elastic deformation were removed at $T_{SM}$; provided the shape memory freezing temperature $T_F$ is above the transition, $T_G$, of the polymer, and provided the polymer is in the amorphous state at $T_F$.

In an embodiment, the present invention provides a polymer having the formula:

comprising:
a) hydrogen bonding units, HB, having at least one hydrogen bond donor moiety and at least one hydrogen bond acceptor moiety;
b) backbone modifier units, MOD; and
c) photochemical crosslinking units, PXL, that are capable of reversibly or irreversibly forming one or more crosslinks as a result of photochemical reactions;
where the indices x, y, and z represent the mole fraction of each unit, the index x is from 0.1 to 40, the index y is from 0.5 to 99.8, and the index z is from 0.1 to 20.

These and other objects, features and advantages will become apparent to those of ordinary skill in the art from a reading of the following detailed description and the appended claims. All percentages, ratios and proportions herein are by weight, unless otherwise specified. All temperatures are in degrees Celsius (° C.) unless otherwise specified. All documents cited are in relevant part, incorporated herein by reference.

DETAILED DESCRIPTION OF THE INVENTION

Figure 1:
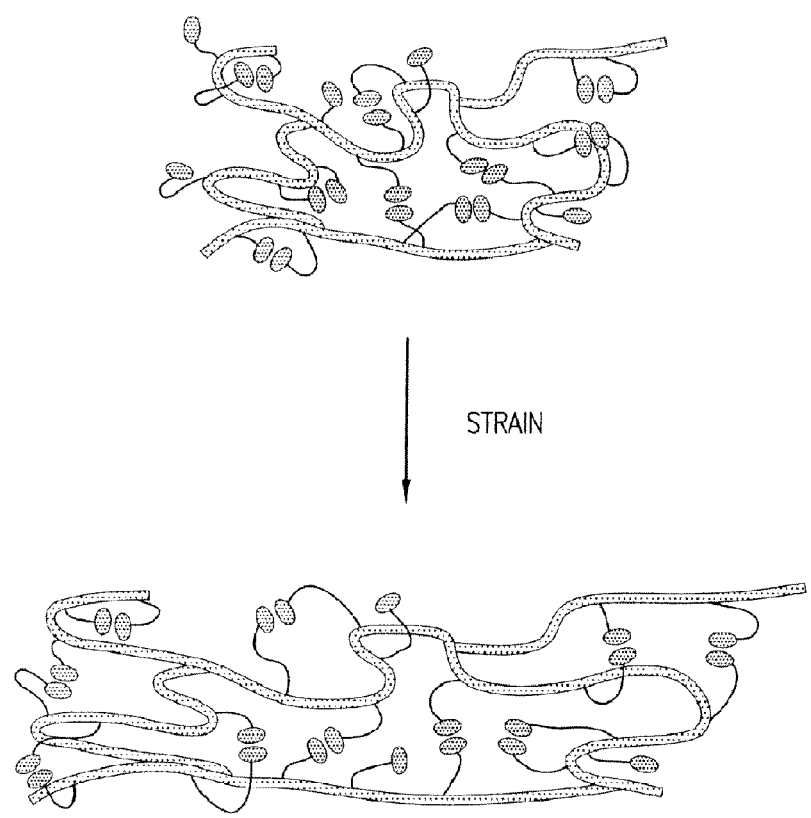
FIG. 1 is a schematic of how the Shape Memory Polymers disclosed herein reassociate after being elastically strained.

Throughout this specification, unless the context requires otherwise, the word "comprise," or variations such as "comprises" or "comprising," will be understood to imply the inclusion of a stated integer or step or group of integers or steps but not the exclusion of any other integer or step or group of integers or steps.

It must be noted that, as used in the specification and the appended claims, the singular forms "a," "an" and "the" include plural referents unless the context clearly dictates otherwise.

"Optional" or "optionally" means that the subsequently described event or circumstance can or cannot occur and that the description includes instances where the event or circumstance occurs and instances where it does not.

Ranges can be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that when a value is disclosed that "less than or equal to" the value, "greater than or equal to the value," and possible ranges between values are also disclosed, as appropriately understood by the skilled artisan. For example, if the value "10" is disclosed, then "less than or equal to 10" as well as "greater than or equal to 10" is also disclosed. It is also understood that throughout the application data are provided in a number of different formats and that these data represent endpoints and starting points and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

A weight percent of a component, unless specifically stated to the contrary, is based on the total weight of the formulation or composition in which the component is included.

By "sufficient amount" and "sufficient time" means an amount and time needed to achieve the desired result or results, e.g., dissolve a portion of the polymer.

"Admixture" or "blend" is generally used herein means a physical combination of two or more different components. In the case of polymers, an admixture, or blend, of polymers is a physical blend or combination of two or more different polymers as opposed to a copolymer that is single polymeric material that is comprised of two or more different monomers.

"Molecular weight" as used herein, unless otherwise specified, refers generally to the relative average chain length of the bulk polymer. In practice, molecular weight can be estimated or characterized in various ways including permeation chromatography (GPC) or capillary viscometry. GPC molecular weights are reported as the weight-average molecular weight ($M_w$) as opposed to the number-average molecular weight ($M_n$). Capillary viscometry provides estimates of molecular weight as the Inherent Viscosity determined from a dilute polymer solution using a particular set of concentration, temperature, and solvent conditions.

The term "number average molecular weight" ($M_n$) is defined herein as the mass of all polymer molecules divided by the number of molecules that are present.

The term "weight average molecular weight" ($M_w$) is defined herein as the mass of a sample of a shape memory polymer divided by the total number of molecules that are present.

The present disclosure relates to Shape Memory Polymers (SMP's) having surprising properties. The Shape Memory Polymers of the present disclosure have three distinct features and/or advantages:
  i) the SMP's are transparent to light at all processing temperatures; they have no glassy or crystalline domains that can scatter light;
  ii) the SMP's exhibit amorphous or rubbery "fixed" states; thereby providing a malleable polymer that functionality can be taken advantage of for permanent as well as temporary uses; and
  iii) the SMP's can be precisely tuned to have differential recovery rates and recovery temperatures based upon the specific need of the formulator.

The Shape Memory Polymers of the present disclosure are, for example, a crosslinked polymer containing reversibly associating side-groups. A schematic of the polymer architecture is shown in FIG. 1. When the material is elastically strained, self-complementary side-groups associate to temporarily hold or "pin" the material in its strained state. Since the association of side-groups is a completely reversible process, the material slowly relaxes to its original, equilibrium shape. From an architectural standpoint, the material can be viewed as having covalent crosslinks that are superimposed onto dynamic, non-covalent crosslinks. The material stiffness is determined by the number of covalent crosslinks, and its shape recovery rate is determined by the number of noncovalent crosslinks and the dynamics of associating side-groups.

The polymers of the present disclosure have a unique combination of properties due to their constituent units that allow the polymers to be deformed or elastically strained from a first shape or size, then subsequently become temporarily pinned into a second deformed or elastically strained state. The bonds formed by the Hydrogen Bonding Units described herein below, serve to lock or pin the polymers into the second state. The polymers of the present disclosure can be returned to the initial state by one of three ways described herein below.

Typically the shape memory polymers are elastically deformed or strained at a particular temperature, the shape memory temperature, $T_{SM}$, that is particular for each application for which the polymer is used and is unique to each polymeric species. First the polymer is raised to a temperature, $T_{SM}$, that provides necessary energy for fast dissociation of existing hydrogen bonds between various units and thereby enables the deformation of the polymer into the desired second shape or configuration. Then the polymer is elastically strained by an applied mechanical force and subsequently cooled to a temperature that is referred to herein as the shape memory freezing temperature, $T_F$, that is also unique to each species of polymer and can be manipulated by the formulator, usually by selection of the type and number of hydrogen bonding units in the polymer. After cooling to the shape memory freezing temperature, the mechanical load is removed. During cooling and before the mechanical elastically straining force is removed, the hydrogen bonding units begin to form new local hydrogen bonds with other units also capable of forming hydrogen bonds. These newly formed hydrogen bonds now serve to lock or pin the polymer into the deformed or strained configuration.

A single hydrogen bond is relatively weak, typically on the order of 5 to 40 kJ/mol. By increasing or decreasing the number of hydrogen bonding units, and, therefore, the number of possible hydrogen bonds capable of being formed within a molecule, the formulator can adjust both the shape memory temperature, as well as the shape memory freezing temperature. However, since one of the advantages of the present polymers is their light transparency and amorphous state, the shape freezing temperature, $T_F$, can be well above the glass transition temperature, $T_G$.

The polymers of the present disclosure also exhibit characteristic strain recovery and mechanical creep that are properties of the particular species and can be adjusted by the formulator. If, for example a mechanical load is applied, cumulative hydrogen bond forces stabilize the polymer's mechanical state, resisting creep. The mechanical creep rate depends on temperature and is much faster at higher temperatures. Furthermore, if a mechanical load is removed, cumulative hydrogen bonds stabilize the polymer's strained state, shape recovery. Likewise, the rate of shape recovery depends on temperature and is much faster at higher temperature. However, the shape memory polymers disclosed herein can be elastically strained by any method that distends the polymer, for example thermally, electrically, and the like.

Figure 2:
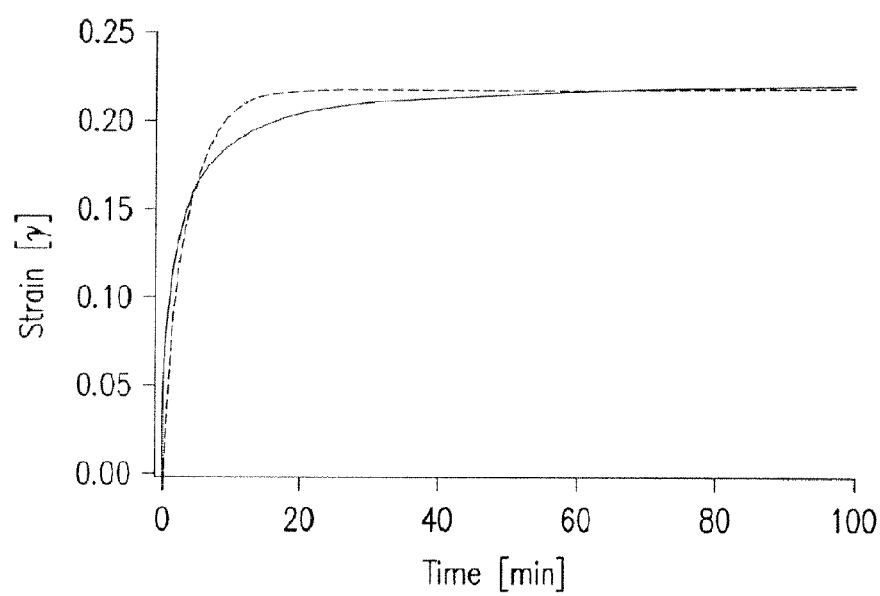
FIG. 2 is a graph of the isothermal (47° C.) creep data for the polymer of Example 4 using a 50 mN tensile load (solid line) and the least-squares fit of these data to the nonlinear constitutive model (dotted line).
Figure 3:
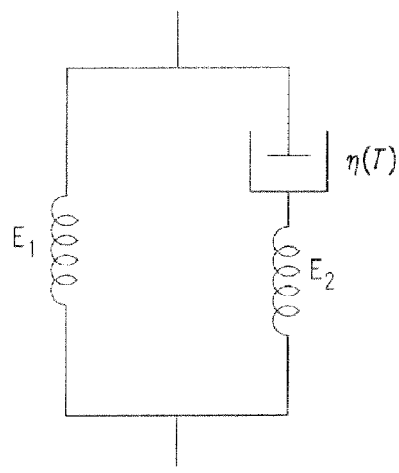
FIG. 3 is structure used to model mechanical behavior of a polymer of the present invention.

Mechanical creep behavior and shape recovery can be studied using a thermogravimetric analysis apparatus. FIG. 2 represents the isothermal mechanical creep data acquired on the polymer described in Example 4 herein below. The measurement temperature was 47° C. and the mechanical load was 50 mN. The dotted line represents the line derived from the mathematical model derived from the constitutive equation below, whereas the solid line represents a least-square fit to the data using a simple model such as that shown in FIG. 3. In FIG. 1, $E_1$, and $E_2$ refer to the elastic moduli corresponding to the springs in the model and $\eta(T)$ refers to the temperature dependent viscosity that is typically measured isothermally in order to design into the polymer the desired recovery rate at the temperature at which the polymer will be used. $E_1$ describes the polymer's instantaneous response to a stress and $E_2$ and $\eta(T)$ taken in series with one another represent a Maxwell element. The constitutive equation for this model is:

$$(E_1 + E_2)\sigma + \eta(T)\frac{d\sigma}{dt} = E_1 E_2 \gamma + E_1 \eta(T)\frac{d\gamma}{dt} \qquad \text{Equation 1}$$

where σ is applied stress and γ is polymer elongation. For a creep experiment, the initial condition is γ=0 and the boundary condition is specified by the applied load, i.e. σ is constant.

Figure 4:
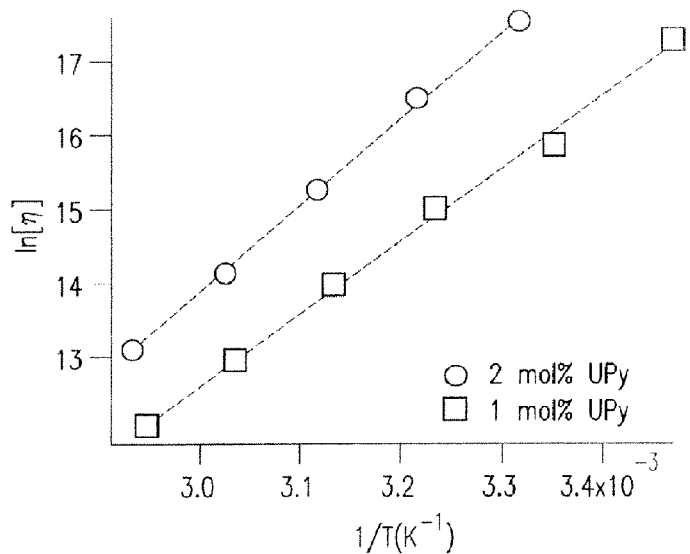
FIG. 4 depicts the Arrhenius temperature-dependence of fitted viscosities obtained from creep data for the polymers of Examples 4 and 5 measured at various temperatures.
Figure 4:
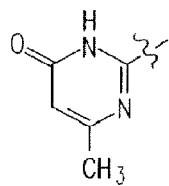

Non-linear least square regression fits to Equation 1 using isothermal creep data, such as those shown in FIG. 2, result in values for $E_1$, $E_2$, and η. A plot of ln(η) against inverse temperature is shown in FIG. 4 for two of the samples discussed herein. By utilizing data such as those found in FIG. 4, the formulator can determine the relative rate of elongation change, dγ/dt, and therefore the relaxation rate or creep for a particular polymer.

Figure 5:
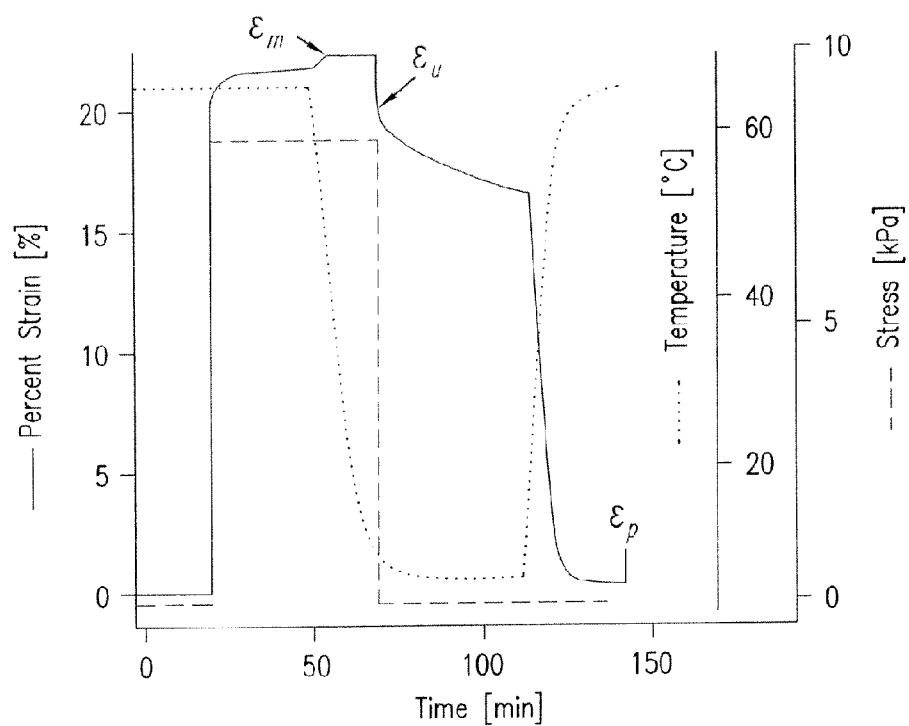
FIG. 5 depicts the shape-memory response curve of the polymer of Example 4.

FIG. 5 depicts an example of the shape-memory response curve for the polymer of Example 4. Shape-memory response curves such as this can be utilized by the formulator to determine the effects that adjustments in the polymer composition will have on relaxation times and other features of the polymer's shape memory response. For example, the solid line in FIG. 4 indicates the percent strain of the polymer at a particular temperature. As the data indicate, the polymer of Example 4 was first equilibrated at the $T_{SM}$ (66° C.) for 20 minutes after which a mechanical force of 50 mN was applied. This force resulted in rapid elongation (solid line) of the shape memory polymer. While maintaining the 50 mN applied force, the temperature of the shape memory polymer was then lowered to the $T_F$ (5° C.). Cooling the polymer furthers its elongation to its maximum ($\epsilon_m$, solid line) that is due to entropy elasticity, and will vary in amount from species to species. Once the polymer is equilibrated at the $T_F$ temperature, the mechanical force is removed and the polymer begins to creep back to its original state at a relaxation rate depicted by the section of the curve immediately following $\epsilon_u$. This rate of deformation is slow but can be accelerated by increasing temperature. As can be seen in FIG. 4, there is a sharp inflection in the curve at the point wherein the temperature of the polymer is raised above the $T_F$. The formulator, by extrapolating outward the curve of percent strain (level of relaxation) versus time measured isothermally at $T_F$, will be able to determine how long it will take the shape-memory polymer to return to the original state. This information will allow the formulator to determine the effects on polymer relaxation rates that adjustments in the relative amounts of polymer constituents will have.

The polymers of the present disclosure are comprised of three types of units:

i) Hydrogen Bonding Units—HB;

ii) Backbone Modifying Units—MOD; and iii) Crosslinking Units—XL.

Each of these units fulfills a function that affects the properties of the final polymer. The Hydrogen Bonding Units serve to form temporary crosslinks between polymer chains (inter chain hydrogen bonding) or semi-permanent crosslinks between other hydrogen bonding units of the same polymer chain (intra chain hydrogen bonding). These HB units serve to temporarily "pin" the polymers of the present disclosure into an elastically strained state. While HB units do undergo dissociation below $T_F$, at low temperatures (below $T_F$) the dissociation rate is slow enough that the polymer remains elongated for relevant application timescales.

The formulator, by incorporating more or less hydrogen bonding units into the shape memory polymer will be able to control the relaxation rate or creep recovery of the polymer back as it returns to its original form (permanent shape) at a given temperature. For a given temperature, increasing the number of hydrogen bonding units will cause a slower relaxation rate, while the number of hydrogen bonding units will cause the polymer to have a faster relaxation rate. In addition, the number of crosslinking units and their length will also affect the relaxation rate.

One way in which the formulator can cause the polymers to rapidly relax into the original state is to raise the temperature of the material above the shape memory temperature, $T_{SM}$, or to a temperature above it. Raising the temperature of the polymer above $T_F$ will also increase the rate of creep, but at a slower rate than raising the temperature to $T_{SM}$ or above.

The present disclosure utilizes the term "hydrogen bond" in the same manner as the artisan of ordinary skill. The terms "hydrogen bond acceptor moiety" and "hydrogen bond donor moiety" are defined herein as "moieties that are capable when at least one acceptor moiety is present and at least one donor moiety is present, of forming a hydrogen bond."

The following are non-limiting examples of the hydrogen bonding formed by the units that comprise the shape memory polymers of the present disclosure:

i) an example of two similar units that are capable of forming two hydrogen bonds between the units:

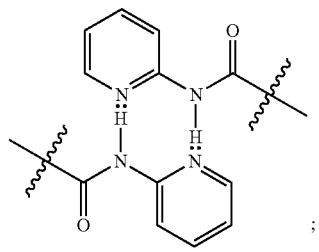

ii) an example of two different units that are capable of forming three hydrogen bonds between the units:

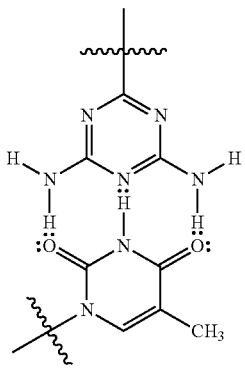

iii) an example of a hydrogen bonding unit wherein hydrogen bonds are formed between Z units (donors) and $R^4$ units (acceptors) that are further described herein below. Those of ordinary skill in the art will also recognize the presence of a potential intra moiety hydrogen bond (arrow) that can help further determine the orientation of the Z and $R^4$ units relative to one another by further assisting in holding hydrogen bonding units in alignment.

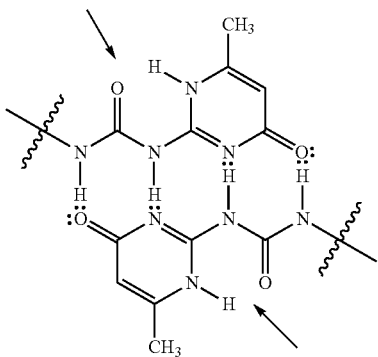

It will be understood by the artisan of ordinary skill, that other refinements and changes to the Q units defined herein below via modification of $R^4$, W, Y, and Z, that are also further defined herein below, will provide variation in the degree of hydrogen bonding.

As shown below, substitution of the ring N—H units will be another means for the formulator to adjust the alignment of hydrogen bonding units in the Q units of the present disclosure, for example, the units having the formula:

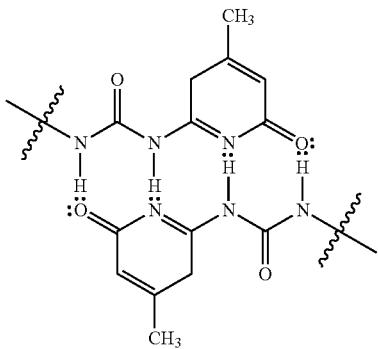

As will be seen further herein below in the description of the present disclosure, the formulator will have great latitude in choosing units that will provide more or less hydrogen bonding, and therefore provide the formulator with a method for varying the properties of the shape memory polymers. The propitious choice of $R^4$ units, mixtures, or variations in $R^4$ will allow the formulator profound latitude in creating various arrays of hydrogen bonds.

The following chemical hierarchy is used throughout the specification to describe and enable the scope of the present disclosure and to particularly point out and distinctly claim the units that comprise the compounds of the present disclosure, however, unless otherwise specifically defined, the terms used herein are the same as those of the artisan of ordinary skill. The term "hydrocarbyl" stands for any carbon atom-based unit (organic molecule), the units optionally containing one or more organic functional group, including inorganic atom comprising salts, inter alia, carboxylate salts, quanternary ammonium salts. Within the broad meaning of the term "hydrocarbyl" are the classes "acyclic hydrocarbyl" and are used to divide hydrocarbyl units into cyclic and non-cyclic classes.

As it relates to the following definitions, "cyclic hydrocarbyl" units may comprise only carbon atoms in the ring (carbocyclic and aryl rings) or may comprise one or more heteroatoms in the ring (heterocyclic and heteroaryl). For "carbocyclic" rings the lowest number of carbon atoms in a ring are 3 carbon atoms; cyclopropyl. For "aryl" rings the lowest number of carbon atoms in a ring are 6 carbon atoms; phenyl. For "heterocyclic" rings the lowest number of carbon atoms in a ring is 1 carbon atom; diazirinyl. Ethylene oxide comprises 2 carbon atoms and is a $C^2$ heterocycle. For "heteroaryl" rings the lowest number of carbon atoms in a ring is 1 carbon atom; 1,2,3,4-tetrazolyl. The following is a non-limiting description of the terms "acyclic hydrocarbyl" and "cyclic hydrocarbyl" as used herein.

A. Substituted and unsubstituted acyclic hydrocarbyl:

For the purposes of the present disclosure the term "substituted and unsubstituted acyclic hydrocarbyl" encompasses 3 categories of units:

1) linear or branched alkyl, non-limiting examples of that include, methyl ($C^1$), ethyl ($C^2$), n-propyl ($C^3$), iso-propyl ($C^3$), n-butyl ($C^4$), sec-butyl ($C^4$), iso-butyl ($C^4$), tret-butyl ($C^4$) and the like; substituted linear or branched alkyl, non-limiting examples of which includes, hydroxymethyl ($C^1$) chloromethyl ($C^1$), trifluoromethyl ($C^1$), aminomethyl ($C^1$), 1-chloroethyl ($C^2$), 2-hydroxyethyl ($C^2$), 1,2-difluoroethyl ($C^2$), 3-carboxypropyl ($C^2$), and the like.

2) linear or branched, alkenyl, non-limiting examples of which include, ethenyl ($C^2$), 3-propenyl ($C^3$), 1-propenyl (also 2-methylethenyl) ($C^3$), isopropenyl (also 2-methylethen-2-yl ($C^3$), buten-4-yl ($C^2$), and the like; substituted linear or branched alkenyl, non-limiting examples of which include, 2-chloroethenyl (also 2-chlorovinyl) ($C^2$), 4-hydroxybuten-1-yl ($C^4$), 7-hydroxy-7-methyloct-4-en-2-yl ($C^9$), 7-hydroxy-7-methyloct-3,5-dien-2-yl ($C^9$), and the like.

3) linear or branched alkynyl, non-limiting examples of which include, ethynyl ($C^2$), prop-2-ynyl (also propargyl) ($C^3$), propyn-1-yl ($C^3$), and 2-methyl-hex-4-yn-1-yl ($C^7$); substituted linear or branched alkynyl, non-limiting examples of which include, 5-hydroxy-5-methylhex-3-ynyl ($C^7$), 6-hydroxy-6-methylhept-3-yn-2-yl ($C^8$), 5-hydroxy-5-ethylhept-3-ynyl ($C^9$), and the like.

B. Substituted and unsubstituted cyclic hydrocarbyl:

For the purposes of the present disclosure the term "substituted and unsubstituted cyclic hydrocarbyl" encompasses 5 of units:

1) The term "carbocyclic" is defined herein as "encompassing rings comprising from 3 to 20 carbon atoms, wherein the atoms that comprise the rings are limited to carbon atoms, and further each ring can be independently substituted with one or more moieties capable of replacing one or more hydrogen atoms." The following are non-limiting examples of "substituted and unsubstituted carbocyclic rings" that encompass the following categories of units:

i) carbocyclic rings having a single substituted or unsubstituted hydrocarbon ring, non-limiting examples of which include, cyclopropyl ($C^3$), 2-methyl-cyclopropyl ($C^3$), cyclopropenyl ($C^3$), cyclobutyl ($C^4$), 2,3-dihydroxycyclobutyl ($C^4$), cyclobutenyl ($C^4$), cyclopentyl ($C^5$), cyclopentenyl ($C^5$), cyclopentadienyl ($C^5$), cyclohexyl ($C^6$), cyclohexenyl ($C^6$), cycloheptyl ($C^7$), cyclooctanyl ($C^8$), decalinyl ($C^{10}$), 2,5-dimethylcyclopentyl ($C^5$), 3,5-dichlorocyclohexyl ($C^6$), 4 hydroxycyclohexyl ($C^6$), and 3,3,5-trimethylcyclohex-1-ly-($C^6$).

ii) carbocyclic rings having two or more substituted or unsubstituted fused hydrocarbon rings, non-limiting examples of which include, octahydropentalenyl ($C^8$), -octahydro-1H-indenyl ($C^9$), 3a,4,5,6,7,7a-hexahydro-3H-inden-4-yl ($C^9$), decahydroazulenyl ($C^{10}$).

iii) carbocyclic rings that are substituted or unsubstituted bicyclic hydrocarbon rings, non-limiting examples of which include, bicyclo-[2.1.1]hexanyl, bicyclo[2.2.1]heptanyl, bicyclo[3.1.1]heptanyl, 1,3-dimethyl[2.2.1]heptan-2-yl,[bicyclo[2.2.2]octanyl, and bicyclo[3.3.3]undecanyl.

2) The term "aryl" is defined herein as "units encompassing at least one phenyl or naphthyl ring and wherein there are no heteroaryl or heterocyclic rings fused to the phenyl or naphthyl ring and further each ring can be independently substituted with one or more moieties capable of replacing one or more hydrogen atoms." The following are non-limiting examples of "substituted and unsubstituted aryl rings" that encompass the following categories of units:

i) $C^6$ or $C^{10}$ substituted or unsubstituted aryl rings; phenyl and naphthyl rings whether substituted or unsubstituted, non-limiting examples of which include, phenyl ($C^6$) naphthylen-1-yl)($C^{10}$), naphthylen-2-yl ($C^{10}$), 4-fluorophenyl ($C^6$), 2-hydroxyphenyl ($C^6$), 3-methylphenyl ($C^6$), 2-amino-4-fluorophenyl ($C^6$), 2-(N,N-diethylamino)phenyl ($C^6$), 2-cyanophenyl ($C^6$), 2,6-di-tert-butylphenyl ($C^6$), 3-methoxyphenyl ($C^6$), 8-hydroxynaphthylen-2-yl ($C^{10}$), 4,5-dimethoxynaphthylen-1yl ($C^{10}$) and 6-cyano-naphthylen-1-yl)($C^{10}$).

ii) $C^6$ or $C^{10}$ aryl rings fused with 1 or 2 saturated rings non-limiting examples of which include, bicyclo[4.2.0]octa-1,3,5-trienyl ($C^8$) and indanyl ($C^9$).

3) The terms "heterocyclic" and/or "heterocycle" are defined herein as "units comprising one or more rings having from 3 to 20 atoms wherein at least one atom in at least one ring is a heteroatom chosen from nitrogen (N), oxygen (O), or sulfur (S), or mixtures of N, O, and S, and wherein further the ring that comprises the heteroatom is also not an aromatic ring." The following are non-limiting examples of "substituted and unsubstituted heterocyclic rings" that encompass the following categories of units:

i) heterocyclic units having a single ring containing one or more heteroatoms, non-limiting examples of which include, diazirinyl ($C_1$), aziridinyl ($C_2$), urazolyl ($C_2$), azetidinyl ($C_3$), pyrazolidinyl ($C_3$), imidazolidinyl ($C_3$), oxazolidinyl ($C_3$), isoxazolinyl ($C_3$), isoxazolyl ($C_3$), thiazolidinyl ($C_3$), isothiazolyl ($C_3$), isothiazolinyl ($C_3$), oxathiazolidinonyl ($C_3$), oxazolidinonyl ($C_3$), hydantoinyl ($C_3$), tetrahydrofuranyl ($C_4$), pyrrolidinyl ($C_4$), morpholinyl ($C_4$), piperazinyl ($C_4$), piperidinyl ($C_4$), dihydropyranyl ($C_5$), tetrahydropyranyl ($C_5$), piperidin-2-onyl (valerolactam) ($C_5$), 2,3,4,5-tetrahydro-1H-azepinyl ($C_6$), 2,3-dihydro-1H-indole ($C_8$), and 1,2,3,4-tetrahydro-quinoline ($C_9$).

ii) heterocyclic units having 2 or more rings one of which is a heterocyclic ring, non-limiting examples of which include hexahydro-1H-pyrrolizinyl ($C_7$), 3a,4,5,6,7,7a-hexahydro-1H-benzo[d]imidazolyl ($C_7$), 3a,4,5,6,7,7a-hexahydro-1H-indolyl ($C_8$), 1,2,3,4-tetrahydroquinolinyl ($C_9$), and decahydro-1H-cycloocta[b]pyrrolyl ($C_{10}$).

4) The term "heteroaryl" is defined herein as "encompassing one or more rings comprising from 5 to 20 atoms wherein at least one atom in at least one ring is a heteroatom chosen from nitrogen (N), oxygen (O), or sulfur (S), or mixtures of N, O, and S, and wherein further at least one of the rings that comprises a heteroatom is an aromatic ring." The following are non-limiting examples of "substituted and unsubstituted heterocyclic rings" that encompass the following categories of units:

i) heteroaryl rings containing a single ring, non-limiting examples of which include, 1,2,3,4-tetrazolyl ($C_1$), [1,2,3]triazolyl ($C_2$), [1,2,4]triazolyl ($C_2$), triazinyl ($C_3$), thiazolyl ($C_3$), 1-H-imidazolyl ($C_3$), oxazolyl ($C_3$), furanyl ($C_4$), thiopheneyl ($C_4$), pyrimidinyl ($C_4$), 2-phenylpyrimidinyl ($C_4$), pyridinyl ($C_5$), 3-methylpyridinyl ($C_5$), and 4-dimethylaminopyridinyl ($C_5$).

ii) heteroaryl rings containing 2 or more fused rings one of which is a heteroaryl ring, non-limiting examples of which include: 7H-purinyl ($C_5$), 9H-purinyl ($C_5$), 6-amino-9H-purinyl ($C_5$), 5H-pyrrolo[3,2-d]pyrimidinyl ($C_6$), 7H-pyrrolo[2,3-d]pyrimidlinyl ($C_6$), pyrido[2,3-d]pyrimidinyl ($C_7$), 2-phenylbenzo[d]thiazolyl ($C_7$), 1H-indolyl ($C_8$), 4,5,6,7-tetrahydro-1-H-indolyl ($C_8$), quinoxalinyl ($C_8$), 5-methylquinoxalinyl ($C_8$), quinazolinyl ($C_8$), quinolinyl ($C_9$), 8-hydroxy-quinolinyl ($C_9$), and isoquinolinyl ($C_9$).

5) $C_1$-$C_6$ tethered cyclic hydrocarbyl units (whether carbocyclic units, $C_6$ or $C_{10}$ aryl units, heterocyclic units, or heteroaryl units) that are connected to another moiety, unit, or core of the molecule by way of a $C_1$-$C_6$ alkylene unit. Non-limiting examples of tethered cyclic hydrocarbyl units include benzyl $C_1$—($C_6$) having the formula:

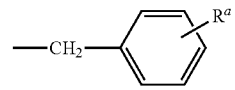

wherein $R^a$ is optionally one or more independently chosen substitutions for hydrogen. Further examples include other aryl units, inter alia, (2-hydroxyphenyl)hexyl $C_6$—($C_6$); naphthalene-2-ylmethyl $C_1$—($C_{10}$), 4-fluorobenzyl $C_1$—($C_6$), 2-(3-hydroxy-phenyl)ethyl $C_2$—($C_6$), as well as substituted and unsubstituted $C_3$-$C_{10}$ alkylenecarbocyclic units, for example, cycloprophlmethyl $C_1$—($C_3$), cyclopentylethyl $C_2$—($C_5$), cyclohexylmethyl $C_1$—($C_6$). Included within this category are substituted and unsubstituted $C_1$-$C_{10}$ alkylene-heteroaryl units, for example a 2-picolyl $C_1$—($C_6$) unit having the formula:

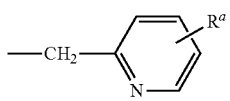

wherein $R^a$ is the same as defined above. In addition, $C_1$-$C_{12}$ tethered cyclic hydrocarbyl units include $C_1$-$C_{10}$ alkylencheterocyclic units and alkylene-heteroaryl units, non-limiting examples of which include, aziridinylmethyl $C_1$—($C_2$) and oxazol-2-ylmethyl $C_1$—($C_3$).

For the purposes of the present disclosure carbocyclic rings are from $C_3$ to $C_{20}$; aryl rings are $C_6$ or $C_{10}$; heterocyclic rings are from $C_1$ to $C_9$; and heteroaryl rings are from to $C_1$ to $C_9$.

For the purposes of the present disclosure, and to provide consistency in defining the present disclosure, fused ring units, as well as spirocyclic rings, bicyclic rings and the like, that comprise a single heteroatom will be characterized and referred to herein as being encompassed by the cyclic family corresponding to the heteroatom containing ring, although the artisan may have alternative characterizations. For example, 1,2,3,4-tetrahydroquinoline having the formula:

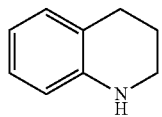

is, for the purposes of the present disclosure, considered a heterocyclic unit. 6,7-Dihydro-5H-cyclopentapyrimidine having the formula:

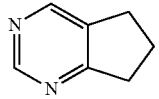

is, for the purposes of the present disclosure, considered a heteroaryl unit. When a fused ring unit contains heteroatoms in both a saturated ring (heterocyclic ring) and an aryl ring (heteroaryl ring), the aryl ring will predominate and determine the type of category to which the ring is assigned herein for the purposes of describing the disclosure. For example, 1,2,3,4-tetrahydro-[1,8]naphthyridine having the formula:

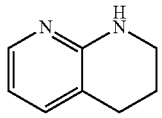

is, for the purposes of the present disclosure, considered a heteroaryl unit.

The term "substituted" is used throughout the specification. The term "substituted" is applied to the units described herein as "substituted unit or moiety is a hydrocarbyl unit or moiety, whether acyclic or cyclic, that has one or more hydrogen atoms replaced by a substituent or several substituents as defined herein below." The units, when substituting for hydrogen atoms are capable of replacing one hydrogen atom, two hydrogen atoms, or three hydrogen atoms of a hydrocarbyl moiety at a time. In addition, these substituents can replace two hydrogen atoms on two adjacent carbons to form the substituent, new moiety, or unit. For example, a substituted unit that requires a single hydrogen atom replacement includes halogen, hydroxyl, and the like. A two hydrogen atom replacement includes carbonyl, oximino, and the like. A two hydrogen atom replacement from adjacent carbon atoms includes epoxy, and the like. Three hydrogen replacement includes cyano, and the like. The term substituted is used throughout the present specification to indicate that a hydrocarbyl moiety, inter alia, aromatic ring, alkyl chain; can have one or more of the hydrogen atoms replaced by a substituent. When a moiety is described as "substituted" any number of the hydrogen atoms may be replaced. For example, 4-hydroxyphenyl is a "substituted aromatic carbocyclic ring (aryl ring)", (N,N-dimethyl-5-amino)octanyl is a "substituted $C_8$ linear alkyl unit, 3-guanidinopropyl is a "substituted $C_3$ linear alkyl unit," and 2-carboxypyridinyl is a "substituted heteroaryl unit."

The following are non-limiting examples of units that can substitute for hydrogen atoms on a carbocyclic, aryl, heterocyclic, or heteroaryl unit:
i) $C_1$-$C_4$ linear or branched alkyl; for example, methyl ($C_1$), ethyl ($C_2$), n-propyl ($C_3$), iso-propyl ($C_3$), n-butyl ($C_4$), iso-butyl ($C_4$), sec-butyl ($C_4$), and tert-butyl ($C_4$);
ii) —$OR^{30}$; for example, —OH, $OCH_3$, —$OCH_2CH_3$, —$OCH_2CH_2CH_3$;
iii) —$C(O)R^{30}$; for example, —$COCH_3$, —$COCH_2CH_3$, —$COCH_2CH_2CH_3$;
iv) —$C(O)OR^{30}$; for example, —$CO_2CH_3$, —$CO_2CH_2CH_3$, —$CO_2CH_2CH_2CH_3$;
v) —$C(O)N(R^{30})_2$; for example, —$CONH_2$, —$CONHCH_3$, —$CON(CH_3)_2$;
vi) —$N(R^{30})_2$; for example, —$NH_2$, —$NHCH_3$, —$N(CH_3)_2$, —$NH(CH_2CH_3)$;
vii) Halogen: —F, Cl, —Br, and I;
viii) —$CH_mX_n$; wherein X is halogen, m is from 0 to 2, m+n=3; for example, —$CH_2F$, —$CH_2F$, —$CHF_2$, —$CF_3$, —$CCl_3$, or —$CBr_3$; and
ix) —$SO_2R^{30}$; for example, —$SO_2H$; —$SO_2CH_3$; —$SO_2C_6H_5$ wherein each $R^{30}$ is independently hydrogen, substituted or unsubstituted $C_1$-$C_4$ linear, branched, or cyclic alkyl; or two $R^{30}$ units can be taken together to form a ring comprising 3-7 atoms. However, substituents that are suitable for replacement of a hydrogen atom are further defined herein below.

The Shape Memory Polymers of the present disclosure are formed from the reaction of one or more monomers from each of the following three categories; hydrogen bonding monomers, backbone modifying monomers, and crosslinking monomers.

As it relates to the amount of hydrogen bonding units present in the polymers of the present disclosure, the following three primary categories are defined herein as:
i) lightly hydrogen bonded polymers: the initial reaction mixture prior to polymerization comprises from about 0.5 mole percent, mol %, to about 5 mol %, of a hydrogen bonding monomer;
ii) moderately hydrogen bonded polymers: the initial reaction mixture prior to polymerization comprises from about 5 mol % to about 10 mol %, of a hydrogen bonding monomer; and
iii) heavily hydrogen bonded polymers: the initial reaction mixture prior to polymerization comprises greater than about 10 mol %, of a hydrogen bonding monomer. A first aspect of heavily hydrogen bonded polymers relates to SMP's having from 10 mol % to 15 mol %, of a hydrogen bonding monomer. Another aspect of heavily hydrogen bonded polymers comprises from 15 mol % to 40 mol %, of a hydrogen bonding monomer.

As it relates to the amount of crosslinking units present in the polymers of the present disclosure, the following four primary categories are defined herein as:

i) very lightly crosslinked polymers: the initial reaction mixture prior to polymerization comprises less than about 0.5 mole percent, mol %, of a crosslinking monomer;

ii) lightly crosslinked polymers: the initial reaction mixture prior to polymerization comprises from about 0.5 mole percent, mol %, to about 1.5 mol %, of a crosslinking monomer;

iii) moderately crosslinked polymers: the initial reaction mixture prior to polymerization comprises from about 1.5 mol % to about 2.5 mol %, of a crosslinking monomer; and iv) heavily crosslinked polymers: the initial reaction mixture prior to polymerization comprises greater than about 2.5 mol %, of a crosslinking monomer. A first aspect of heavily crosslinked polymers relates to SMP's having from 2.5 mol % to 3.5 mol %, of a crosslinking monomer. Another aspect of heavily crosslinked polymers comprises from 3.0 mol % to 5 mol %, of a crosslinking monomer.

As is disclosed further herein below, crosslinking monomer also encompasses monomers having a moiety which after chain formation can serve to form crosslinks between polymer chains or within a polymer chain.

Mole percent, mol %, according to the present disclosure is calculated as in the example that follows. The three monomers:

i) a HB monomer having the formula:

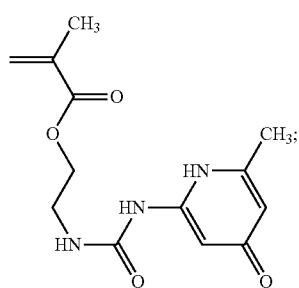

ii) a MOD monomer havig the formula:

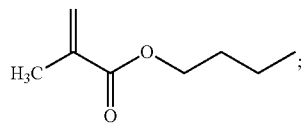

and iii) a XL monomer having the formula:

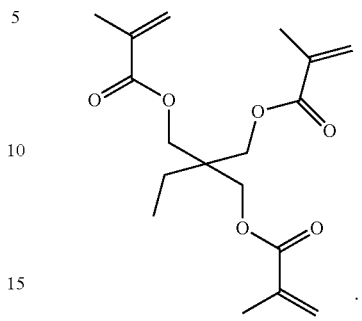

are admixed together prior to initiation of the polymerization reaction. The monomers have the following molecular weights respectively; HB=279.3 g/mol, MOD=142.2 g/mol, and XL=338.4 g/mol. The admixture comprises the following amount of each monomer:

| Monomer type | Mass (g) | Mol % |
|---|---|---|
| MOD | 13.51 | 95 |
| HB | 0.56 | 2 |
| XL | 1.02 | 3 |

The resulting polymer from this admixture is a heavily crosslinked polymer as defined herein.

Hydrogen Bonding Units, HB

The shape-memory polymers of the present disclosure comprise hydrogen bonding units, HB, having the formula:

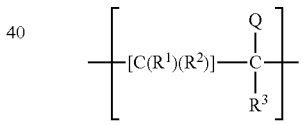

wherein each $R^1$ and $R^2$ is independently chosen from:
i) hydrogen;
ii) $C_1$-$C_6$ alkyl;
iii) halogen;
iv) cyano; and
v) phenyl;

$R^3$ is chosen from:
i) hydrogen; and
ii) $C_1$-$C_6$ alkyl.

The formulator may chose to use a single HB unit comprising monomer when forming the shape memory polymers of the present disclosure, or as described herein below, a mixture of hydrogen bonding monomers may be used. As it relates to the shape memory polymers of the present disclosure, one category of polymers comprises both $R^1$ and $R^2$ equal to hydrogen and $R^3$ equal to methyl. These HB units can be considered to be derivatives methacrylic acid. A further category of polymers comprises $R^1$, $R^2$, and $R^3$ equal to hydrogen. These HB units can be considered to be derivatives of acrylic acid.

Q represents a unit having at least one hydrogen bond donor moiety and at least one hydrogen bond acceptor moiety. Q is further defined as a unit having the formula:

wherein L is a linking unit having the formula:

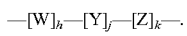

When the index i is equal to 1, the linking unit L is present, however, if the index i is equal to 0, the linking unit L is absent and $R^4$ is bonded directly to the polymer backbone providing a HB unit having the formula:

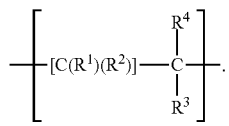

The expanded definition of Q, wherein the indices h, i, j, and k are each equal to 1, has the formula:

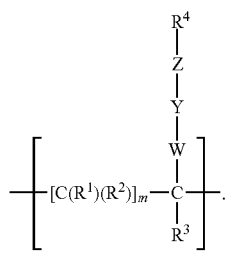

In various embodiments, the hydrogen bonding units have from 2 to 8 hydrogen-bonding units. The hydrogen-bonding units can have hydrogen bond acceptor units, hydrogen-bond donor units or a combination thereof. The units can be self-complementary or hetero-complementary. Self-complementary units can form intermolecular H-bonds with identical units. An example of a self-complementary H-bonding interaction is that between carboxylic acid groups. Hetero-complementary units can form intermolecular H-bonds with complementary units. An example of a hetero-complementary H-bonding interaction is that observed between guanine and cytosine.

The hydrogen bonding backbone units are incorporated into the Shape Memory Polymers by way of HB monomers. An example of one category of HB monomers has the formula:

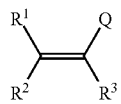

which when full expanded has the formula:

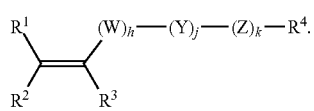

A first category of monomers relates to methacrylate-based monomers having the general formula:

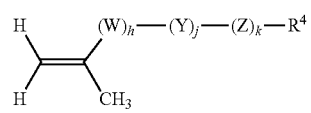

that are conveniently derived from methacrylic acid.

Another category of monomers relates to acrylate-based monomers having the general formula:

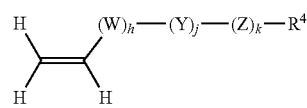

that are conveniently derived from acrylic acid.

As it relates to the position of the units that form the hydrogen bonds in the Q unit, it is not necessary that a hydrogen bonding acceptor or hydrogen bonding donor be present in any particular position, unit, or moiety; this is left to the prerogative of the formulator to increase and/or decrease the degree of potential hydrogen bond formation.

For example, in the first Category of HB units according to the present disclosure, hydrogen bonding donors and acceptors are found in the Z unit, as well as in the $R^4$ unit. For example, the Q unit having the formula:

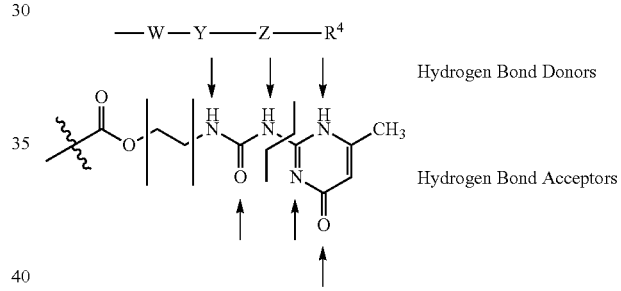

comprises hydrogen donors and acceptors in both the $R^4$ unit, as well as the Z unit. The categories of HB units will be set forth in detail herein below.

The units W and Z are each independently chosen from:
i) —C(O)—;
ii) —C(O)O—;
iii) —OC(O)—;
iv) —NH—;
v) —C(O)NH—;
vi) —NHC(O)—;
vii) —NHC(O)NH—;
viii) —NHC(=NH)NH—; and
ix) —O—;

wherein the indices h and k are independently equal to 0 or 1. When the index h is 0 the W unit is absent, however, when h is equal to 1 the W unit is present. Likewise, when the index k is equal to 0 the Z unit is absent, however, when k is equal to 1 the Z unit is present.

Y is a unit having one or more units chosen from:
i) —$(CR^{5a}R^{5b})_s$—;
ii) —$[(CR^{5a}R^{5b})_v(CR^{5a'}R^{5b'})_u]_w$—;
iii) —$[(CR^{5a}R^{5b})_tO]_w$—; or
iv) —$[(CR^{5a}R^{5b})_tO]_w(CR^{5a}R^{5b})_{s-}$;

wherein each $R^{5a}$ and $R^{5b}$ is independently chosen from:
i) hydrogen;
ii) hydroxyl; or
iii) $C_1$-$C_4$ alkyl;
$R^{5a'}$ and $R^{5b'}$ are each independently $C_1$-$C_4$ alkyl.

The index j is 0 or 1. When the index j is 0 the Y unit is absent, however, when j is equal to 1, the Y unit is present. The indices s, t, u, v, and w are each independent of one another and are defined as follows; the index s is from 0 to 10, the index t is from 2 to 10, the index u is from 1 to 10, the index v is from 1 to 10, the index w is from 1 to 10.

The first category of Y units relates to alkylene and alkyl substituted alkylene linking units having the formulae:

that provide for linking units comprising the same alkylene units or mixtures of different alkylene units.

The first aspect of the first category of Y units relates to Y units that comprise a (C2) alkylene linking unit thereby providing Y units having the formula —CH$_2$CH$_2$— (ethylene). This unit is defined herein as Y equal to:

wherein all $R^{5a}$ and $R^{5b}$ units are hydrogen and the index s is equal to 2. Ethylene units can be used to connect any of the W and Z units described herein above. The following are non limiting examples of combinations of W and Z units that can be suitably combined with this first category of Y units (ethylene):

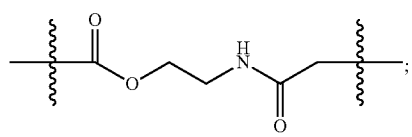
i)

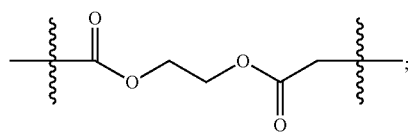
ii)

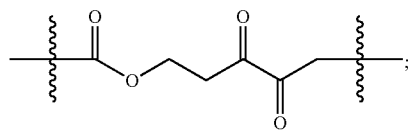
iii)

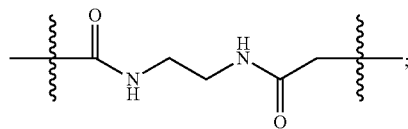
iv) and

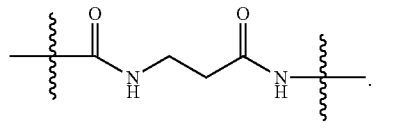
v)

The second of the first category of Y units relates to $C_3$ alkylene linking units. There are two iterations of Y units encompassed within the second aspect of the first category of Y units. The first iteration relates to units wherein the index s is equal to 3 and each $R^{5a}$ and $R^{5b}$ is equal to hydrogen thereby providing a propylene unit having the formula: —CH$_2$CH$_2$CH$_2$—.

A non-limiting example of a Y unit comprising a propylene unit taken together with a W unit and Z unit has the formula:

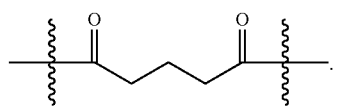

The second iteration of the second aspect of the first category of Y units relates to units having the formula:

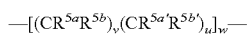

wherein the index v is equal to 1, the index u is equal to 1, and w can have the value from 1 to 10; $R^{5a}$ and $R^{5b}$ are each equal to hydrogen, $R^{5a'}$ is methyl and $R^{5b'}$ is hydrogen thereby providing the following two iso-propylene units having the formulae:

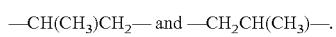

Non limiting examples of combinations of W and Z units that can be suitably combined with this second iteration of Y units include the following:
i) a Y unit wherein the index w is equal to 1 includes:

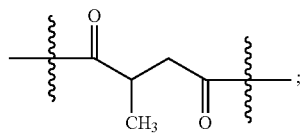

and
ii) a Y unit wherein the index w is equal to 2 includes:

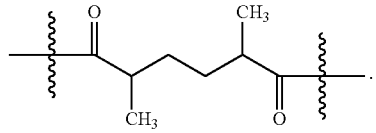

The third aspect of the first category of Y units relates to L linking units having the formula:

wherein each $R^{5a}$ and $R^{5b}$ is equal to hydrogen and the index s is from 4 to 10.

The first iteration of the third aspect of the first category of Y units relates to units wherein the index is from 4 to 6, the units chosen from:
i) —CH$_2$CH$_2$CH$_2$CH$_2$—; (butylene)
ii) —CH$_2$CH$_2$CH$_2$CH$_2$CH$_2$—; (pentylene) and
iii) —CH$_2$CH$_2$CH$_2$CH$_2$CH$_2$CH$_2$— (hexylene).

The second iteration of the third aspect of the first category of Y units relates to units wherein the index s is from 7 to 10, the units chosen from:
i) —CH$_2$CH$_2$CH$_2$CH$_2$CH$_2$CH$_2$CH$_2$—; (heptylene)
ii) —CH$_2$CH$_2$CH$_2$CH$_2$CH$_2$CH$_2$CH$_2$CH$_2$—; (octylene)
iii) —CH$_2$CH$_2$CH$_2$CH$_2$CH$_2$CH$_2$CH$_2$CH$_2$CH$_2$—; (nonylene) and
iv) —CH$_2$CH$_2$CH$_2$CH$_2$CH$_2$CH$_2$CH$_2$CH$_2$CH$_2$CH$_2$—; (decylene)

The second category of Y units relates to alkyleneoxyalkylene units having the formula:

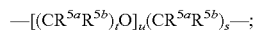

wherein the first aspect of the second category of Y units encompasses ($C_2$) ethyleneoxy units wherein the indices s and t are both equal to 2, each $R^{5a}$ and $R^{5b}$ unit is hydrogen, and u is from 1 to 10. Non-limiting examples of ethyleneoxy units in combination with a W and a Z unit include the following:

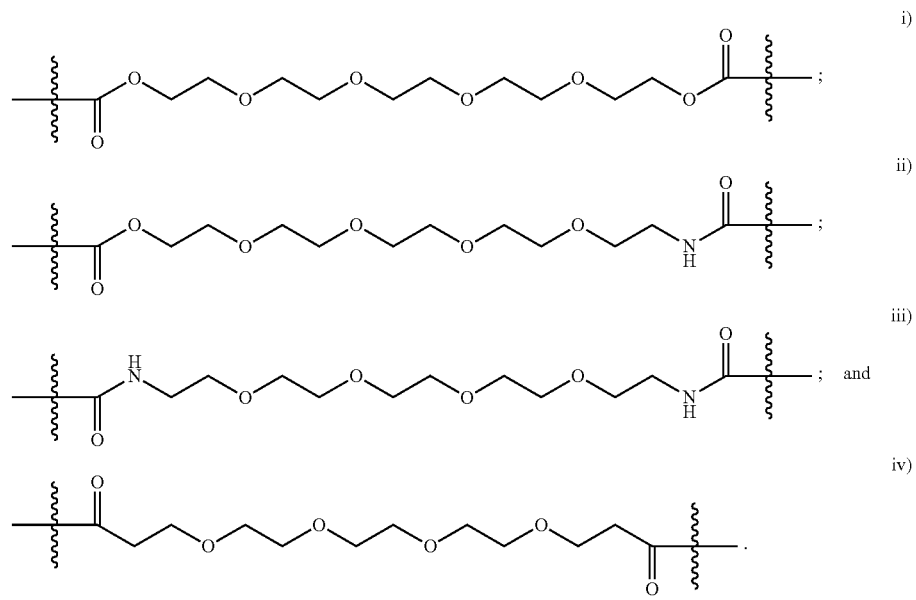

A second aspect of the second category of Y units relates to alkyleneoxyalkylene units having the formula:

$$—[(CR^{5a}R^{5b})_t O]_w (CR^{5a}R^{5b})_s—;$$

wherein at least one $R^{5a}$ unit of the Y unit is equal to methyl and the remaining non-methyl $R^{5a}$ units are hydrogen, while all the $R^{5b}$ units present are hydrogen. This aspect, therefore, encompasses at least one propyleneoxy ($C_3$) unit in the linking unit Y, non-limiting examples which when taken in combination with a W and a Z unit include the following:

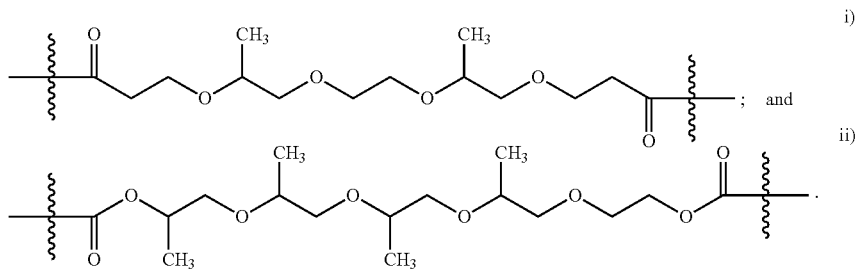

The third category of Y units relates to units wherein at least one $R^{5a}$ unit in the Y unit is equal to hydroxy, for example, a Y unit taken together with a W and a Z unit having the formula:

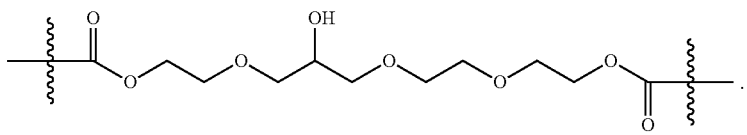

The artisan of ordinary skill will understand that units comprising a hydroxyl can be incorporated into Y units in various ways known in the art. As a non-limiting example, the two step process:

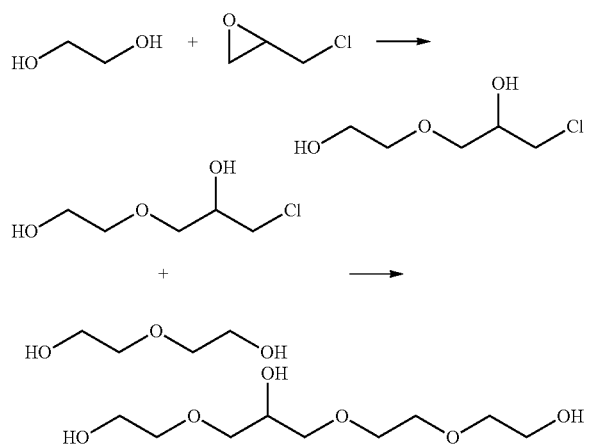

is one method that the artisan can use to prepare a unit containing a hydroxyl unit and that can then be linked to compatible W and Z units.

$R^4$ is a unit chosen from:
i) Hydrogen;
ii) a substituted carbocyclic ring;
iii) a substituted aryl ring;
iv) a substituted or unsubstituted heterocyclic ring; or
v) a substituted or unsubstituted heteroaryl ring;
the substitution is a moiety capable of being a hydrogen bond donor or a hydrogen bond acceptor. Because carbocyclic and aryl rings do not comprise a hydrogen bond forming unit, they are substituted with one or more units that are capable of forming a hydrogen bond.

The first category of $R^4$ units relates to substituted or unsubstituted heterocyclic and heteroaryl rings.

The first aspect of the first category of $R^4$ units relates to substituted or unsubstituted $C_3$ or $C_4$ heterocyclic or heteroaryl 5-member rings, non-limiting examples of that are chosen from:
i) a pyrrolidinyl ring having the formula;

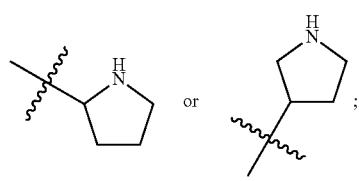

ii) a pyrrolyl ring having the formula:

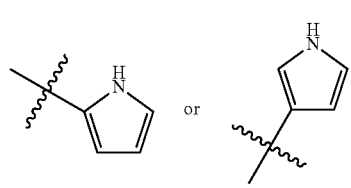

iii) a 4,5-dihydroimidazolyl ring having the formula:

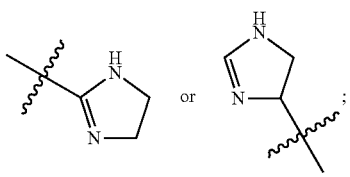

iv) an imidazolyl ring having the formula:

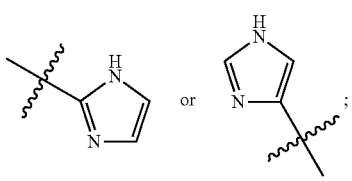

v) a pyrrolidinonyl ring having the formula:

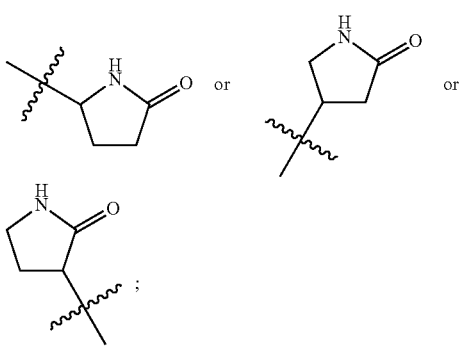

vi) an imidazolidinonyl ring having the formula:

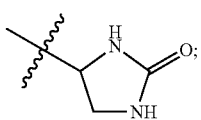

vii) an imidazol-2-only ring having the formula:

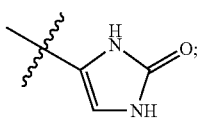

viii) an oxazolyl ring gnivah the formula:

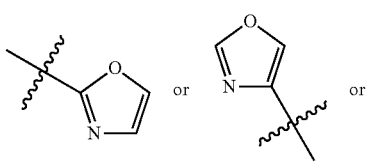

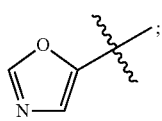

ix) a furanly ring having the formula:

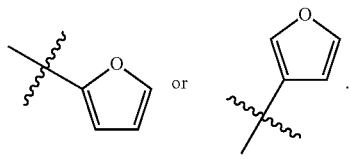

Rings belonging to this first category of $R^4$ can be substituted rings bonded to the balance of the HB unit via a nitrogen heteroatom, for example

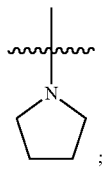

the units comprising one or more hydrogen bonding moieties, for example, pyrrolidinyl units derived from proline, hydroxyproline, or hydroxypyrrolidine having the formulae:

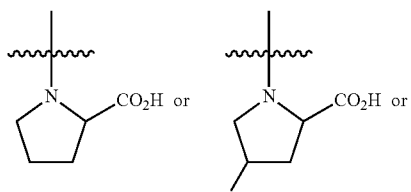

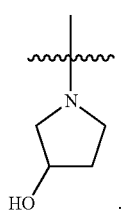

Other rings belonging to this category can be similarly substituted, for example,

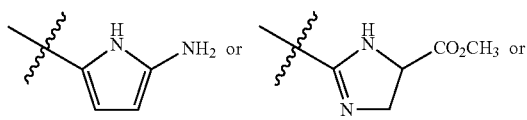

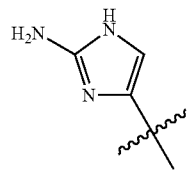

The second aspect of the first category of $R^4$ units relates to substituted or unsubstituted $C_3$, $C_4$ or, $C_5$ heterocyclic or heteroaryl 6-member rings, non-limiting examples of which are chosen from:

i) a morpholinyl ring having the formula:

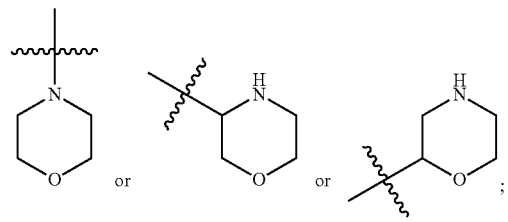

ii) a piperidinyl ring having the formula:

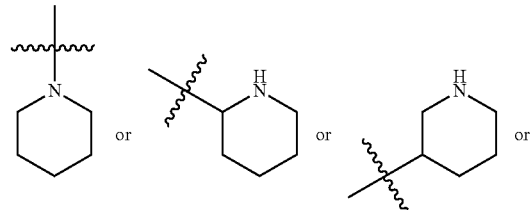

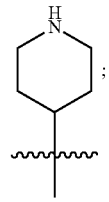

iii) a pyridinyl ring having the formula:

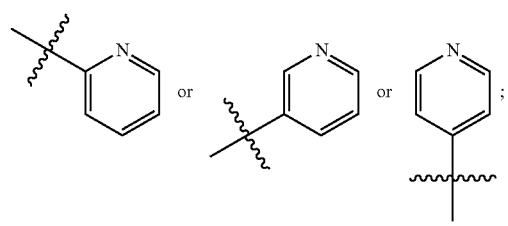

iv) a piperazinyl ring having the formula:

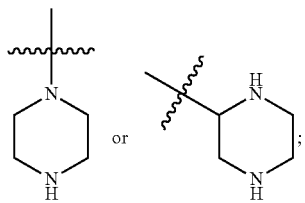

v) a ketopiperazinyl ring having the formula:

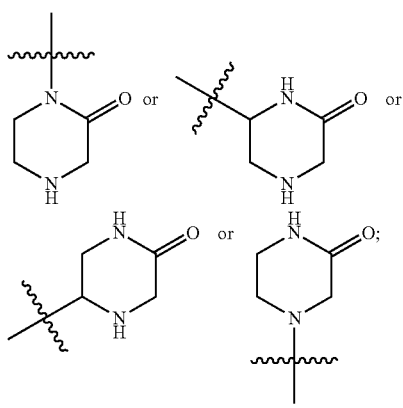

vi) a dihydropyrazin2-onyl ring having the formula:

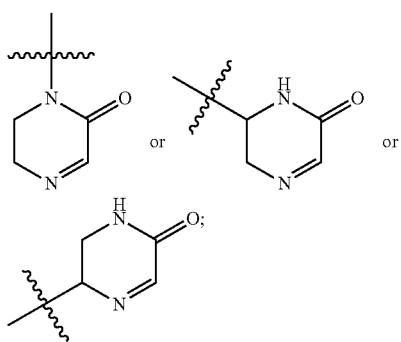

vii) a pyrazin-2-onyl ring having the formula:

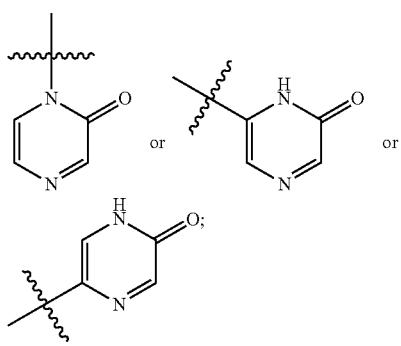

viii) dihydropyrimidin-4-onyl having the formula:

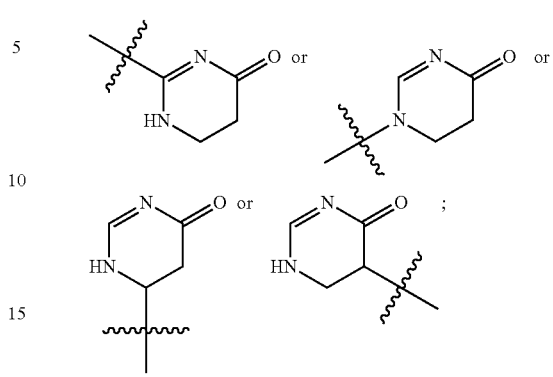

ix) a uracil ring having the formula:

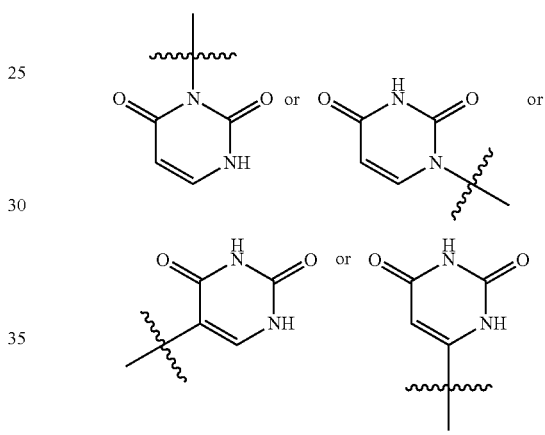

and x) a triazinyl ring having the formula:

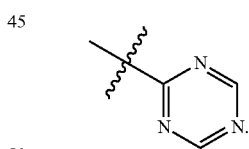

Hydrogen bonding units that are readily incorporated into the shape-memory polymers of the present disclosure include:

i) 6-methylpyrimidin-4-(1H)-on-2-yl having the formula:

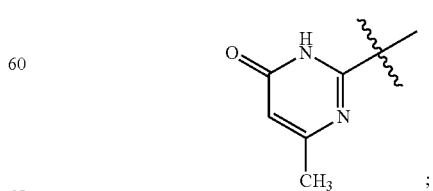

ii) 6-methylpyrimidin-4-(3H)-on-2-yl having the formula:

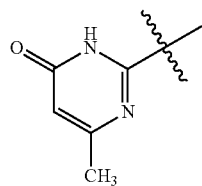

iii) 6-aminopyrimidin-4-(1H)-on-2-yl having the formula:

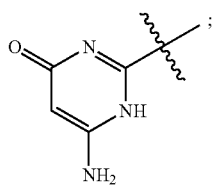

and iv) 6-aminopyrimidin-4-(3H)-on-2-yl having the formula:

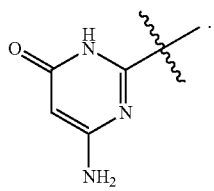

As is the case with the 5-member heterocyclic and heteroaryl rings, the 6-member rings can be substituted with one or more units capable of forming a hydrogen bond.

The third aspect of the first category of $R^4$ units relates to substituted or unsubstituted $C_4$, $C_5$, or $C_6$ heterocyclic or heteroaryl 9-member fused rings, non-limiting examples of which are chosen from:

i) purinyl rings having the formula:

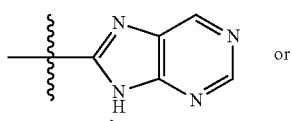

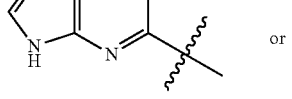

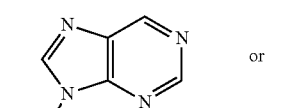

ii) amino purinyl rings having the formula:

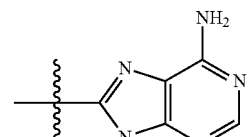

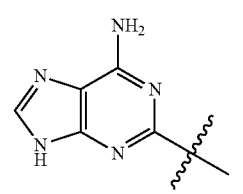

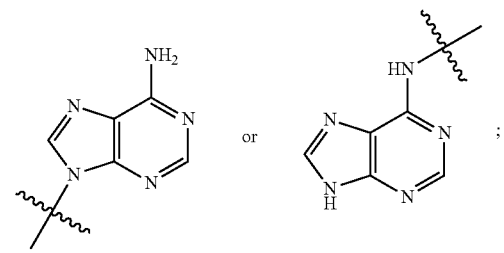

iii) aminopurinonyl rings having the formula:

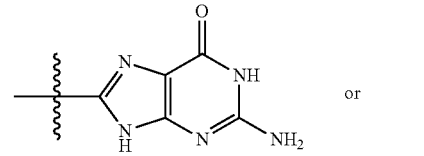

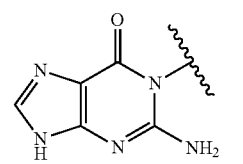

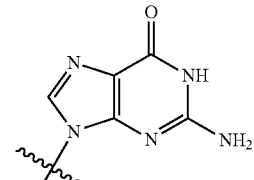

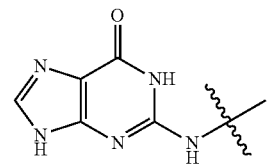

iv) pyrrolo[3,2-d]pyrimidinyl rings having the formula:

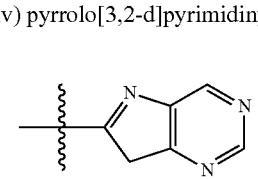

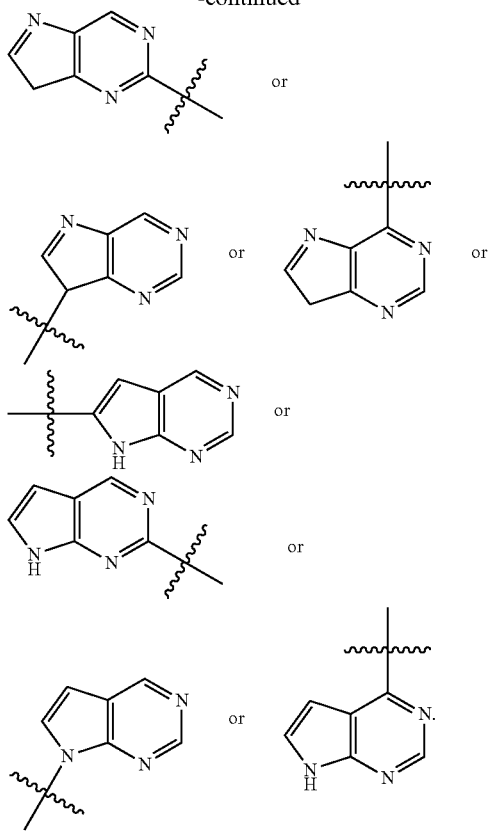

As is the case with the 5-member and 6-member heterocyclic and heteroaryl rings, the fused ring heterocyclic and heteroaryl units can be substituted with one or more units capable of forming a hydrogen bond.

As it relates to the substitutions that can replace a hydrogen atom on the heterocyclic or heteroaryl rings that comprise the $R^4$ units of the present disclosure, the following is a non-limiting description. Typically the substitutions are hydrogen bond accepting or hydrogen bond donating units, however, the alkyl units of the present disclosure are also acceptable substitutions for hydrogen. Without being limited by theory, the presence of alkyl substitutions may stabilize the ring or provide for a more favorable orientation. In addition to the substitutes for hydrogen defined herein above, the following are further non-limiting examples of substituents that are suitable for replacing a hydrogen atom of the $R^4$ units, the units are chosen from:

i) $C_1$-$C_4$ linear or branched alkyl; for example, methyl ($C_1$), ethyl ($C_2$), n-propyl ($C_3$), iso-propyl ($C_3$), n-butyl ($C_4$), iso-butyl ($C_4$), sec-butyl ($C_4$), and tert-butyl ($C_4$);

ii) —$NR^{6a}R^{6b}$; for example, —$NH_2$, —$NHCH_3$, —$N(CH_3)_2$, —$NHC_2H_5$, and —$N(C_2H_5)_2$;

iii) —$C(O)OR^7$; for example, —$C(O)OH$, —$C(O)OCH_3$; and —$C(O)OC_2H_5$;

iv) —$C(O)R^7$; for example, —$C(O)CH_3$; and —$C(O)C_2H_5$;

v) —$C(O)NR^{6a}R^{6b}$; for example, —$C(O)NH_2$, —$C(O)NHCH_3$, —$C(O)N(CH_3)_2$, —$C(O)NHC_2H_5$, and —$C(O)(C_2H_5)_2$;

vi) —$NR^8C(O)NR^{6a}R^{6b}$; for example, —$NHC(O)NH_2$, —$NHC(O)NHCH_3$, —$NHC(O)N(CH_3)_2$, —$NHC(O)NHC_2H_5$, and —$NHC(O)(C_2H_5)_2$;

vii) —$NR^8C(O)R^7$; for example, —$NHC(O)CH_3$, and —$NHC(O)C_2H_5$; and viii) —$NR^8C(=NR^8)NR^{6a}R^{6b}$; for example, —$NHC(=NH)NH_2$, —$NHC(=NH)NHCH_3$, —$NHC(=NH)N(CH_3)_2$, —$NHC(=NH)NHC_2H_5$, and —$NHC(=NH)(C_2H_5)_2$;

wherein $R^{6a}$, $R^{6b}$, $R^7$, and $R^8$ are each independently chosen from hydrogen, methyl, or ethyl.

The second category of $R^4$ units relates to substituted $C_6$ aryl(phenyl) and $C_{10}$ aryl (1-naphthyl and 2-naphthyl) units. The phenyl and naphthyl units that comprise the second category of $R^4$ units can be substituted with any of the units described herein above. Non-limiting examples of $C_6$ and $C_{10}$ substituted aryl units of the present disclosure include: 3-hydroxyphenyl, 4-hydroxyphenyl, 3,5-dihydroxyphenyl, 3-methoxyphenyl, 4-methoxyphenyl, 3,5-dimethoxyphenyl, 3-(dimethylamino)phenyl, 4-(dimethylamino)phenyl, 3-(acetyl)phenyl, 4-(dimethylamino)phenyl, 3-(acetyl)phenyl, 4-(acetyl)phenyl, 3-hydroxy-4acetylphenyl, and the like.

The hydrogen bonding units of the present disclosure can be changed to fit the precise needs that are desired by the formulator. In addition to the selection of W and Z units, as well as $R^4$ units, the length of the linking unit L can be shortened or lengthened by changing or omitting W, Y, and Z units. This lengthening or shortening of the Y unit will provide the formulator with a method for controlling the tether to which the hydrogen bonding $R^4$ unit is attached and, therefore, the distance over which hydrogen bonds may be formed inter or intra molecularly. For example, beginning with acryloyl chloride a hydrogen bonding monomer comprising the following general formula:

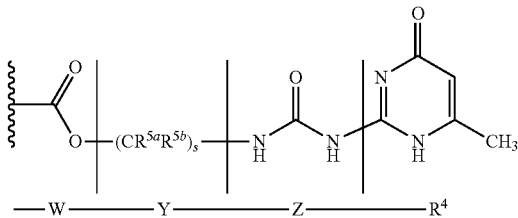

can be prepared over several steps, for example, by first reacting acryloyl chloride with a protected amino alcohol:

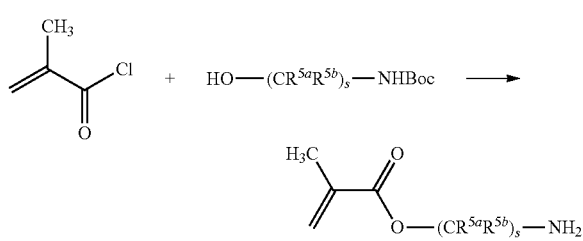

and thereby, a simple varying of the number of —$(CR^{5a}R^{5b})$— units in the amino alcohol, will provide a method for modifying the length of the tether to fit the needs of the formulator. This intermediate can then be reacted with hydrogen bonding moieties to form hydrogen bonding, HB, monomers. For example, joining the intermediate formed above with a —Z—$R^4$ precursor unit:

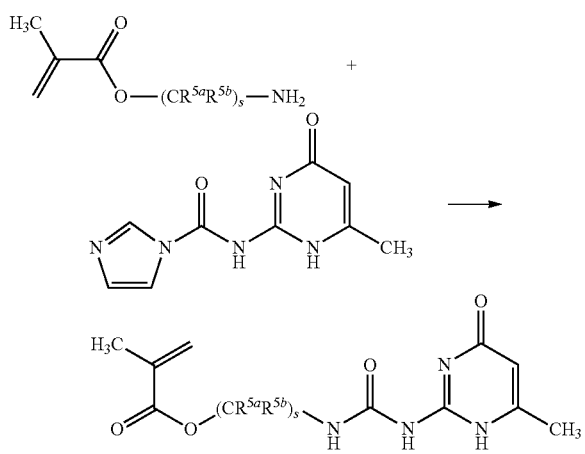

results in a hydrogen bonding monomer wherein the Y tether can be adjusted by the choice of initial reagents, as well as the $R^4$ and Z unit, to fit the variable needs of the formulator.

Another advantage of the present disclosure that the formulator can take into account when preparing the shape memory polymers of the present disclosure, is the differential rate at which hydrogen bonding units will "find" each other. For example, the more complex the hydrogen bonding unit, the long the time necessary for the units to locate a like hydrogen bonding unit once the elastically strained state is achieved. These more complex hydrogen bonding units will provide polymers having a slower relaxation time, but in addition, will also be provided a longer period of time when the polymer is initially elastically strained, wherein the formulator can make secondary adjustments to the shape memory polymer while the hydrogen bond ordering is occurring.

Backbone Modifier Units, MOD

The backbone modifier units of the present disclosure have the formula:

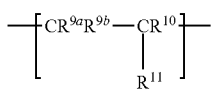

wherein each $R^{9a}$, $R^{9b}$, and $R^{10}$ is independently chosen from:
i) hydrogen; or
ii) $C_1$-$C_4$ alkyl; methyl ($C_1$), ethyl ($C_2$), n-propyl ($C_3$), iso-propyl ($C_3$), n-butyl ($C_4$), iso-butyl ($C_4$), sec-butyl ($C_4$), and tert-butyl ($C_4$).

$R^{11}$ is a unit chosen from;
i) hydrogen;
ii) $C_1$-$C_4$ linear or branched alkyl; for example, ethyl ($C_1$), ethyl ($C_2$), n-propyl ($C_3$), iso-propyl ($C_3$), n-butyl ($C_4$), iso-butyl ($C_4$), sec-buytl ($C_4$), and tert-butyl ($C_4$);
iii) —$NR^{12a}R^{12b}$; for example, —$NH_2$, —$NHCH_3$, —$N(CH_3)_2$, —$NHC_2H_5$, $N(C_2H_5)_2$, —$NHC_3H_7$, —$N(C_3H_7)_2$, —$N(CH_3)(C_2H_5)$, —$N(CH_3)(C_3H_7)$, and $N(C_2H_5)(C_3H_7)$;
iv) —$C(O)OR^{13}$; for example,
 a) —C(O)OH;
 b) —$C(O)OCH_3$;
 c) —$C(O)OCH_2CH_3$;
 d) —$C(O)OCH_2CH_2CH_3$;
 e) —$C(O)OCH(CH_3)_2$;
 f) —$C(O)OCH_2CH_2CH_2CH_3$;
 g) —$C(O)OCH_2CH_2CH_2CH_2CH_3$; and
 h) —$C(O)OCH_2CH_2CH_2CH_2CH_2CH_3$;
v) —$C(O)R^{13}$; for example,
 a) —$C(O)CH_3$;
 b) —$C(O)CH_2CH_3$;
 c) —$C(O)CH_2CH_2CH_3$;
 d) —$C(O)CH(CH_3)_2$;
 e) —$C(O)CH_2CH_2CH_2CH_3$;
 f) —$C(O)CH_2CH_2CH_2CH_2CH_3$; and
vi) —$C(O)NR^{12a}R^{12b}$; for example, —$C(O)NH_2$, —$C(O)NHCH_3$, —$C(O)N(CH_3)_2$, —$C(O)NHC_2H_5$, AND —$C(O)NH(C_2H_5)_2$;

Wherein $R^{12a}$, $R^{12b}$, and $R^{13}$ are each independently hydrogen or $C_1$-$C_{10}$ alkyl.

As in the case of hydrogen bonding units, backbone modifier units are incorporated into the Shape Memory Polymer of the present disclosure by way of MOD monomers.

A first category of MOD monomers has the formula:

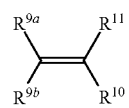

wherein $R^{9a}$ and $R^{9b}$ are each independently hydrogen or methyl ($C_1$), $R^{10}$ is chosen from hydrogen, methyl ($C_1$) and ethyl ($C_2$); $R^{11}$ is an ester or amide unit.

In a first aspect of the first category of backbone modifier units $R^{9a}$ and $R^{9b}$ are both hydrogen, $R^{10}$ is methyl ($C_1$), and $R^{11}$ is an ester unit having the formula —$C(O)OR^{13}$; providing a monomer having the formula:

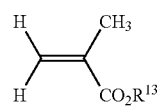

wherein $R^{13}$ is chosen from methyl ($C_1$), ethyl ($C_2$), n-propyl ($C_3$), n-butyl ($C_4$), n-pentyl ($C_5$), n-hexyl ($C_6$), and n-heptyl ($C_7$); thereby providing a backbone modifier unit having the formula:

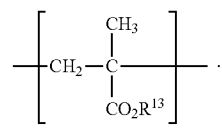

Non-limiting examples of this embodiment include:

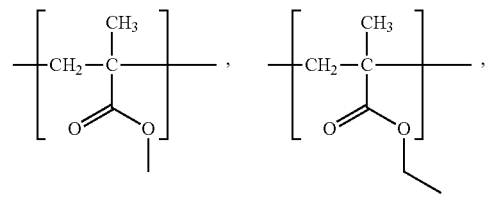

-continued

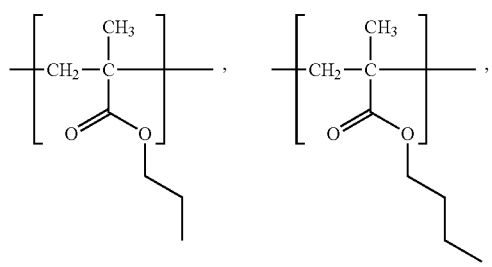

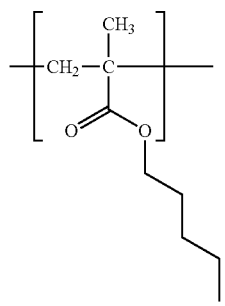  and

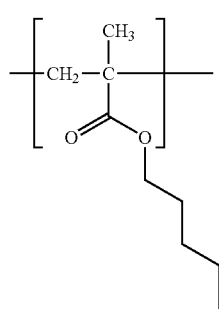

In a second aspect of the first category of backbone modifier units $R^{9a}$ and $R^{9b}$ are both hydrogen, $R^{10}$ is methyl ($C_1$), $R^{11}$ is an amide unit having the formula $-C(O)NR^{12a}R^{12b}$; wherein $R^{12a}$ is hydrogen, thereby providing a backbone modifier unit having the formula:

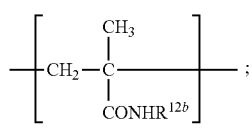

$R^{12b}$ is $C_1$-$C_{10}$ alkyl, inter alia, methyl ($C_1$), ethyl ($C_2$), n-propyl ($C_3$), n-butyl ($C_4$), n-pentyl ($C_5$), n-hexyl ($C_6$), and n-heptyl ($C_7$). Non-limiting examples of this embodiment include:

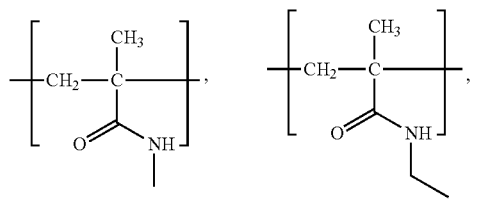

-continued

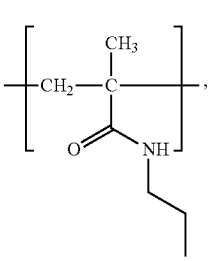

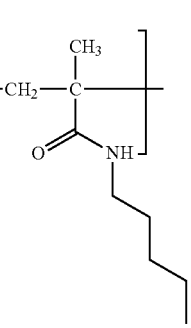 and

In a third aspect of the first category of backbone modifier units $R^{9a}$, $R^{9b}$, and $R^{10}$ are each hydrogen and $R^{11}$ is an ester unit having the formula $-C(O)OR^{13}$; providing a monomer having the formula:

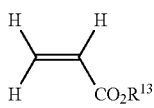

wherein $R^{13}$ is chosen from methyl ($C_1$), ethyl ($C_2$), n-propyl ($C_3$), n-butyl ($C_4$), n-pentyl ($C_5$), n-hexyl ($C_6$), and n-heptyl ($C_7$); thereby providing a backbone modifier unit having the formula:

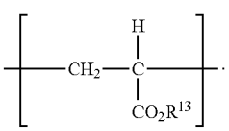

Non-limiting examples of this embodiment include:

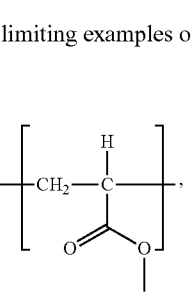

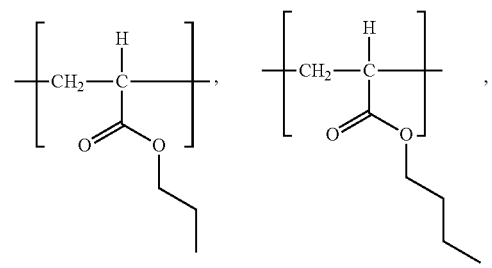
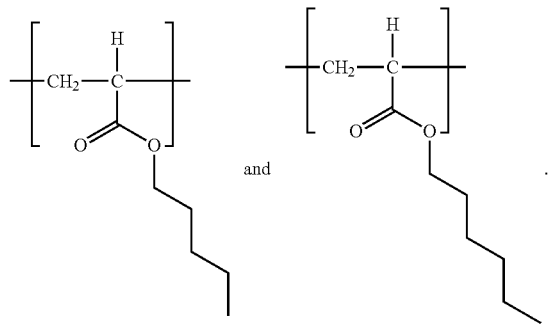

In a fourth aspect of the first category of backbone modifier units $R^{9a}$, $R^{9b}$, and $R^{10}$ are each hydrogen and, $R^{11}$ is an amide unit having the formula —C(O)NR$^{12a}$R$^{12b}$; wherein $R^{12a}$ is hydrogen, thereby providing a backbone modifier unit having the formula:

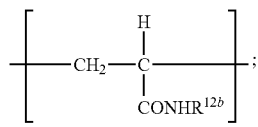

$R^{12b}$ is $C_1$-$C_{10}$ alkyl, inter alia, methyl ($C_1$), ethyl ($C_2$), n-propyl ($C_3$), n-butyl ($C_4$), n-pentyl ($C_5$), n-hexyl ($C_6$), and n-heptyl ($C_7$). Non-limiting examples of this embodiment include:

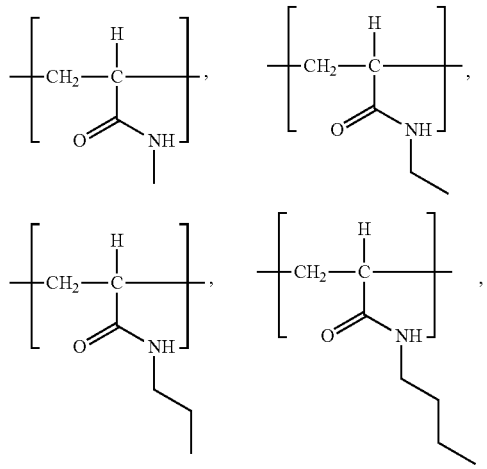

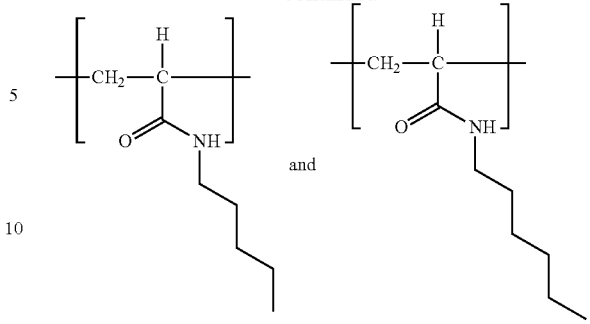

Crosslinking Units, XL

The crosslinking units of the present disclosure are units that are capable of forming a crosslink between two chains. In the first category of crosslinking units, the crosslink is formed between two crosslinking units on different chains, or sections of a single chain. In a second category, crosslinking may occur between a crosslinking unit having a reactive moiety and a functional group of a chain modifier unit.

The crosslinking units of the present disclosure can have the formula:

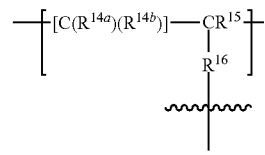

wherein $R^{14a}$, $R^{14b}$, and $R^{15}$ are each independently chosen from:
  i) hydrogen; or
  ii) $C_1$-$C_4$ alkyl; for example, methyl ($C_1$), ethyl ($C_2$), n-propyl ($C_3$), iso-propyl ($C_3$), n-butyl ($C_4$), iso-butyl ($C_4$), sec-butyl ($C_4$), and tert-butyl ($C_4$).

$R^{16}$ units serve to connect two polymer chains or separate sections of a chain. In an embodiment, where two separate polymer chains are crosslinked by a crosslinking unit, the two units once joined, $R^{16}$ will have the formula:

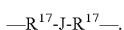

—R$^{17}$-J-R$^{17}$—.

Each $R^{17}$ is independently chosen from
  i) —(CH$_2$)$_p$C(O)(CH$_2$)$_q$—;
  ii) —(CH$_2$)$_p$C(O)O(CH$_2$)$_q$—;
  iii) —(CH$_2$)$_p$OC(O)(CH$_2$)$_q$—;
  iv) —(CH$_2$)$_p$NH(CH$_2$)$_q$—;
  v) —(CH$_2$)$_p$C(O)NH(CH$_2$)$_q$—;
  vi) —(CH$_2$)$_p$NHC(O)(CH$_2$)$_q$—;
  vii) —(CH$_2$)$_p$NHC(O)NH(CH$_2$)$_q$—;
  viii) —(CH$_2$)$_p$NHC(=NH)NH(CH$_2$)$_q$—; and
  ix) —(CH$_2$)$_p$O(CH$_2$)$_q$—
the indices p and q have the value from 0 to 10; when p is 0 the —(CH$_2$)— is absent; when q is 0 the —(CH$_2$)— is absent;
J is a unit having the formula:

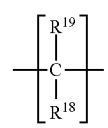

wherein $R^{18}$ and $R^{19}$ are each independently:
i) hydrogen; or
ii) $C_1$-$C_{10}$ alkyl; or
iii) a unit capable of forming a crosslink to a third XL unit, the unit chosen from:
a) —$(CH_2)_rC(O)H$;
b) —$(CH_2)_rC(O)OH$;
c) —$(CH_2)_pOC(O)H$;
d) —$(CH_2)_rNH_2$;
e) —$(CH_2)_pC(O)NH_2$;
f) —$(CH_2)_rNHC(O)H$;
g) —$(CH_2)_rNHC(O)NH_2$;
h) —$(CH_2)_rNHC(=NH)NH_2$;
i) —$(CH_2)_rC(=CH_2)CH_3$;
j) —$(CH_2)_rOH$; and wherein the index r has the value from 0 to 10; when r is 0 the —$(CH_2)$— is absent.

As with the HB and MOD units of the present disclosure, XL units are derived from monomers that react with HB and MOD units to form a polymer backbone. In a first category of XL units, there is a monomer that comprises two polymer chain forming units. The first aspect of the XL monomers relates to units having the formula;

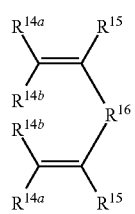

wherein each of the double bonds can independently react to form part of a separate polymer chain, $R^{16}$ is a unit that serves as a crosslinker. When the definition of $R^{16}$ is expanded, XL monomers of the first aspect of the first category have the formula:

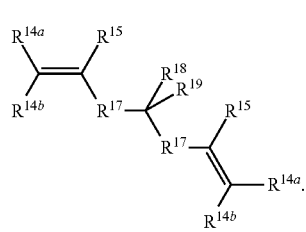

The following is a non-limiting example of a generic scheme that depicts the crosslinking of a XL unit according to the first category of crosslinking units. In this generic example both $R^{17}$ units are —C(O)O— units and J is a unit not capable of independently participating in polymer backbone formation. The generic crosslinking unit having the formula:

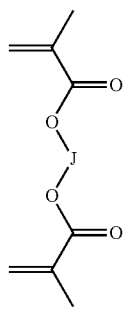

is reacted with a generic HB monomer and a generic MOD monomer to form a non-limiting example of a resultant generic polymer according to the scheme herein below.

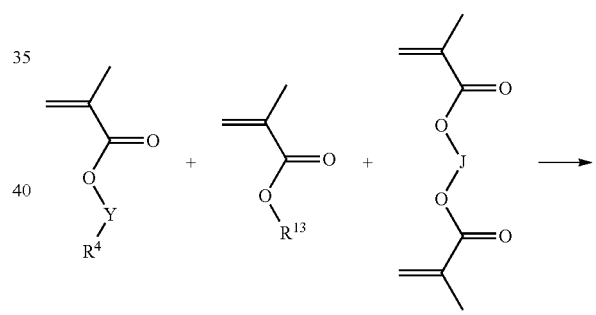

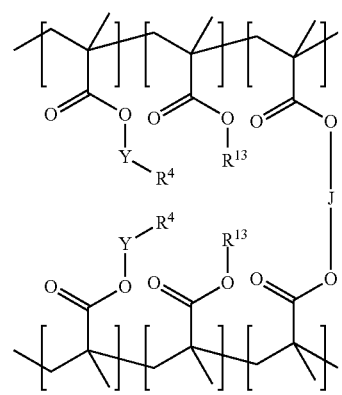

As discussed herein above, the formulator is not restricted to only one monomer from each category for preparing the memory polymers of the present disclosure. For example, the scheme below depicts two different HB units being incorporated into a shape memory polymer of the present disclosure.

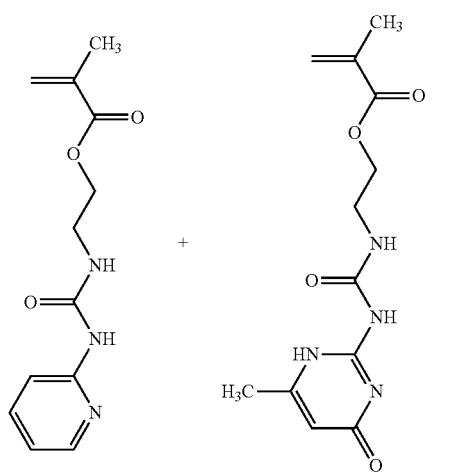

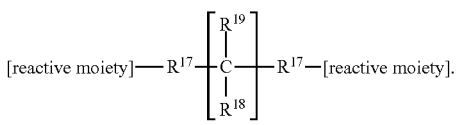

The reactive moieties that are suitable for undergoing reaction to form a crosslinked polymer chain include those that are capable of reacting under typical polymerization condition, inter alia, thermal, free radical, photo reaction, and cationic or anionic polymerization.

The artisan of ordinary skill will realize the reactive moieties of the polymer chain will in many instances be different from the reactive moiety that comprises the J unit precursor. As a non-limiting example, a bis-alcohol linking unit precursor can be reacted with a polymer chain comprising methacrylic acid units to form crosslinks as depicted herein below:

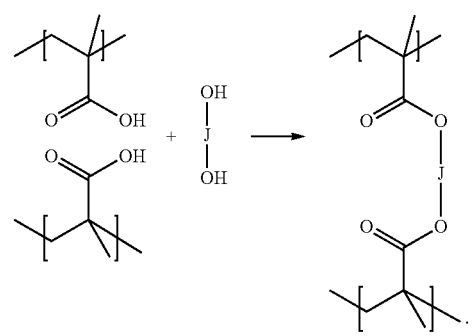

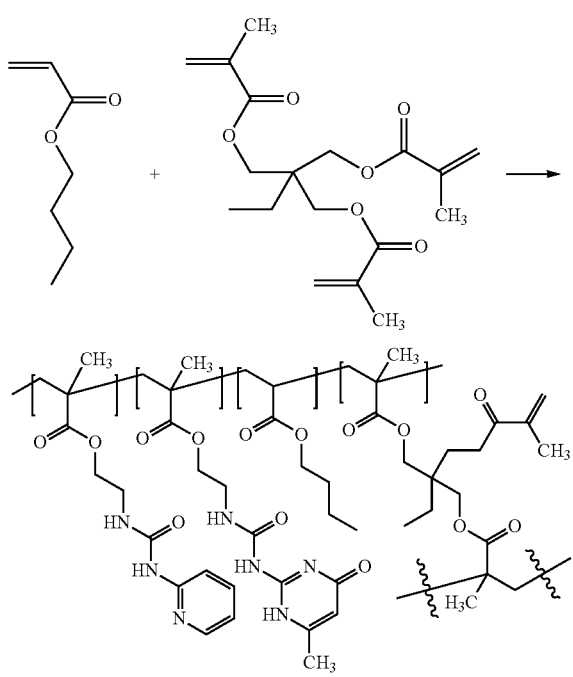

Likewise, any mixture of monomers can be used to formulate the shape memory polymers of the present disclosure.

The second category of XL units relates to monomers that comprise a unit that, once the polymer backbone is formed, contains a unit that can react with a reactive species that serves to form the final crosslink between two chains.

The XL monomers of the second category have the formula:

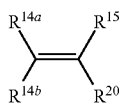

wherein $R^{20}$ is a unit comprising a reactive moiety capable of reaction with a reactive moiety of a J unit precursor, for example, a unit having the general formula:

A further category of XL cross-linking units relates to photo crosslinking units, for example, units that are capable of forming crosslinks between two polymer chains when exposed to electromagnetic radiation, i.e., UV light. Shape Memory Polymers comprising photo crosslinking units can be cured by exposure to UV radiation. By varying the exposure time and light intensity the formulator can control the amount of cross linking present.

In an embodiment, the XL crosslinking units as disclosed herein are photochemical crosslinking units. The photochemical crosslinking units of the present disclosure are units that are capable of forming a reversible or irreversible crosslink between two chains of the polymer. The crosslink can be formed between different chains (e.g., a photochemical crosslinking unit on one chain and another chain or two photochemical crosslinking units on different chains), or two parts of a single chain (e.g., a photochemical crosslinking unit on a first part of the chain and a second part of the chain or a photochemical crosslinking unit on a first part of the chain and a photochemical crosslinking unit on a second part of the chain).

In an embodiment, the PXL unit comprises a reactive moiety (a P unit) that on irradiation with the appropriate wavelength of light forms irreversible crosslinks. For example, the reactive moiety can form a radical species that reacts to form a covalent bond, e.g., by hydrogen atom abstraction. Non-limiting examples of such moieties include benzophenone, substituted benzophenones, benzyl ketals, acetophonones, substituted acetophenones, and the like.

In an embodiment, the PXL unit comprises a reactive moiety (P unit) that on irradiation with an appropriate wavelength of light reacts with a reactive moiety of another PXL unit to form a reversible crosslink. For example, on irradiation with an appropriate wavelength of light two reactive moieties can undergo a dimerization reaction which forms a reversible crosslink. Non-limiting examples of reactive moieties include coumarin, cinnimates, anthracenes, thyamines, and the like.

In an embodiment, the PXL unit has the formula:

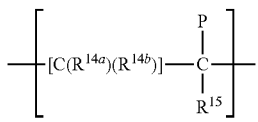

where each $R^{14a}$ and $R^{14b}$ is independently chosen from: hydrogen, $C_1$-$C_6$ alkyl, halogen, cyano, and $C_5$-$C_6$ aryl, and $R^{15}$ is independently selected from hydrogen and $C_1$-$C_6$ alkyl. P is a unit that on exposure to a first wavelength causes formation of an intrachain or interchain crosslink bond. In an embodiment, the P unit can include a linking unit as disclosed herein.

A non-limiting example of photo crosslinking unit (or a photochemical crosslinking unit) is found in the monomer comprising a coumarin unit, the monomer having the formula:

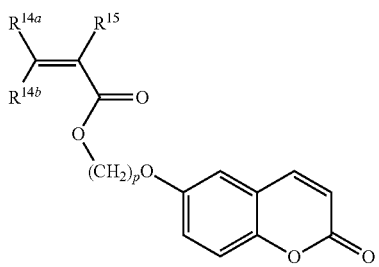

wherein $R^{14a}$, $R^{14b}$, $R^{15}$, and the index p are defined herein above.

In various embodiments, where the polymer comprises a photochemical crosslinker, after irradiation with the appropriate wavelength of light from 10% to 100% of the photochemical crosslinkers form crosslinks.

The formulator can, by using this method of crosslinking, have an admixture of non-crosslinked copolymers that is a liquid and crosslink the polymer to form a solid or non-flowable crosslinked shape memory polymer. The formulator can make use of this embodiment by pouring the admixture of linear copolymers into a mold or other shape forming container, applying UV light, and thereby obtain the shape memory polymer in a desire form. Or in an alternative, a viscous solution of linear copolymers can be drawn out under UV radiation to form long threads or wires of shape memory polymers. An iteration of this embodiment is to draw out the shape memory polymers that can be crosslinked at two different UV wavelengths, wherein one is more reactive. In this way a partially crosslinked polymer can be drawn out at first wavelength of UV radiation, formed into a desired configuration, then full crosslinked by UV radiation at a second wavelength.

The Shape Memory Polymers of the present disclosure are formed, e.g., by reacting under suitable conditions, three types of monomers;

a) from about 0.5 to about 5 mol % of a monomer having the formula:

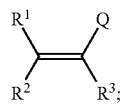

b) from about 90 to about 99 mol % of a monomer having the formula:

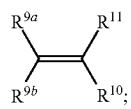

and c)
i) from about 0.5 to about 5 mol % of a monomer having the formula:

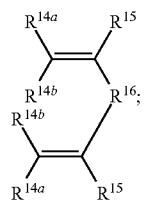

or ii) from about 0.5 to about 5 mol % of a monomer having the formula:

wherein $R^{20}$ is a reactive moiety capable of either:

a) reacting directly with another $R^{20}$ unit of a second polymer chain to for a $R^{16}$ crosslinking unit; or b) two $R^{20}$ units from two polymer chains are capable of reacting with a molecule that comprises two reactive groups capable of reacting with both $R^{20}$ units for form a $R^{16}$ crosslinking unit.

A first category of polymers relates to reaction of:

a) From about 0.5 to about 5 mol % of one or more monomers having the formula:

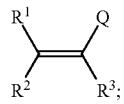

b) From about 90 to about 99 mol % of one or more monomers having the formula:

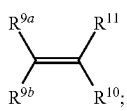

and c) From about 0.5 to about 5 mol % of one or more monomers having the formula:

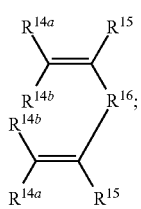

wherein each crosslinking monomer comprises a unit on two separate chains.

For example the generic monomer represented by the formula:

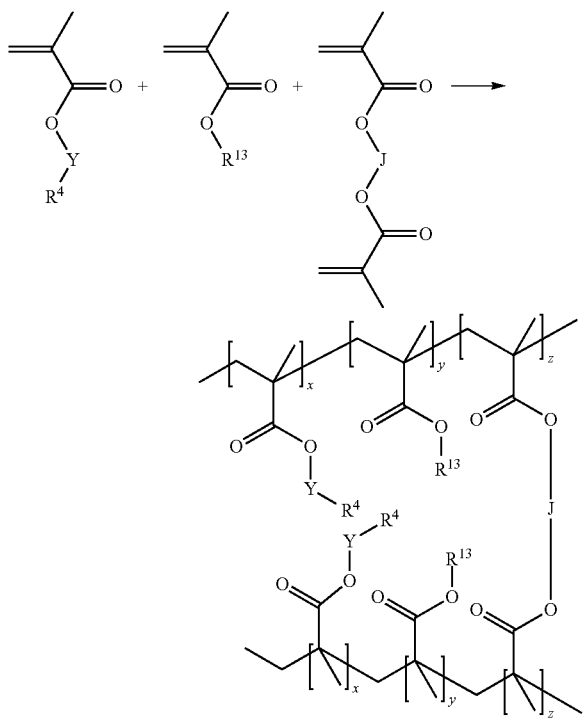

wherein the value for the index x (HB unit) is 5, the value for the index y (MOD unit) is 90, and the value for the index z (XL unit) is 5, as prepared by combining 5 mol % of a HB unit, 90 mol % of a MOD unit and 5 mol % of a crosslinking unit. This polymer would be represented the following formula:

-[HB]$_5$-[MOD]$_{90}$-[XL]$_5$-.

A second category of polymers relates to reaction of:

a) from about 0.5 to about 5 mol % of one or more monomers having the formula:

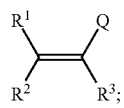

b) from about 90 to about 99 mol % of one or more monomers having the formula:

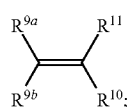

and c) from about 0.5 to about 5 mol % of one or more monomers having the formula:

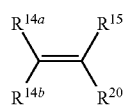

to form shape-memory polymer precursors in the form of linear polymeric chains that are then subsequently crosslinked, wherein $R^{20}$ comprises a reactive moiety that forms crosslinks after the polymer backbones are formed.

$R^{20}$ is a reactive moiety that is capable of reacting with an intermediate such that two $R^{20}$ units from two separate polymer chains react with the intermediate to form a crosslink between two polymer chains. A first iteration encompasses $R^{20}$ units chosen from:

i) —C(O)OR$^{21}$;
ii) —NCO; and
iii) —N$_3$;

wherein $R^{21}$ is hydrogen or $C_1$-$C_4$ linear or branched alkyl.

In addition, the $R^{20}$ units described herein above have reactive units capable of reacting with a di-functional molecule to form a shape memory polymer according to the present disclosure, the di-functional molecule has the formula:

$R^{22}$-J-$R^{22}$ $R^{22}$ each is independently chosen from:

i) ClC(O)(CH$_2$)$_b$—;
ii) Cl(CH$_2$)$_b$—;
iii) H$_2$N(CH$_2$)$_b$—;
iv) HOC(O)(CH$_2$)$_b$—;
v) HO(CH$_2$)$_b$—;
vi) OCN(CH$_2$)$_b$—; and
vii) N$_3$(CH$_2$)$_b$—;

the index b is from 1 to 10.

A non-limiting example of this aspect includes shape memory polymer precursor chains having a —C(O)OH reactive moiety, for example:

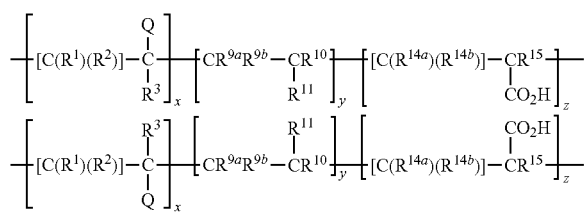

are treated with 1,8-dihydroxyoctane to form a shape memory polymer:

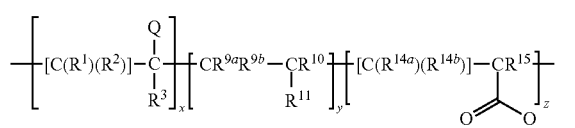

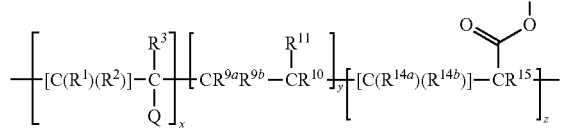

The following scheme shows the process for forming shape memory polymers of the present disclosure wherein the crosslinking is done after the polymer backbone is formed.

The first step involves forming linear polymer chains, for example, polymer chain formation produces a linear, crosslinkable backbone as depicted below, wherein RM represents a reactive moiety:

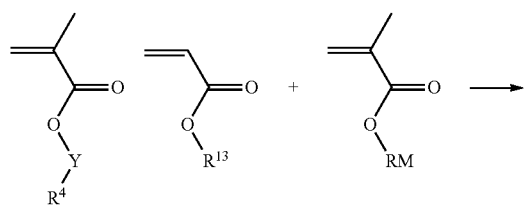

After backbone formation, the polymer is reacted with a compound that contains reactive moieties that can be used to crosslink the linear chains and thereby form a shape memory polymer.

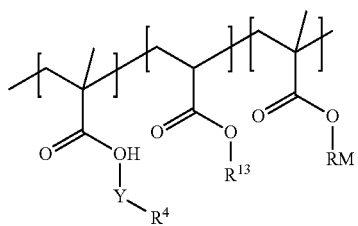

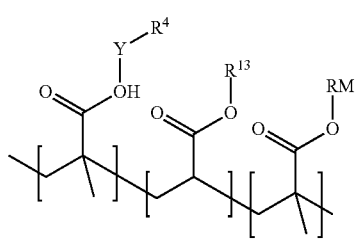

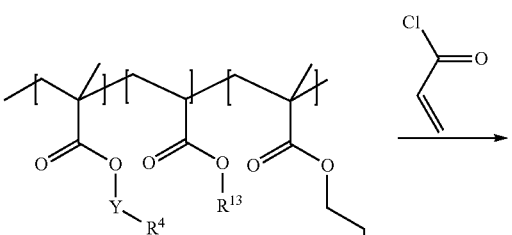

The following is a non-limiting generic example wherein a reactive moiety is added to a polymer backbone after which the polymer can be crosslinked by photo-crosslinking methods using UV radiation and a photoacid generator.

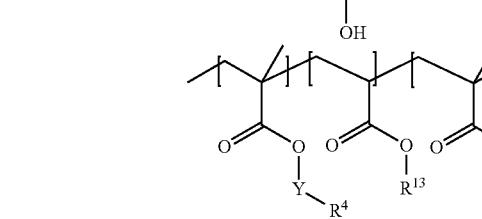

In a third category, the crosslinking monomer may comprise a reactive unit in such a manner that when after the polymer backbones are formed, the formulator may then crosslink the chains to form the final polymer as depicted in the following scheme:

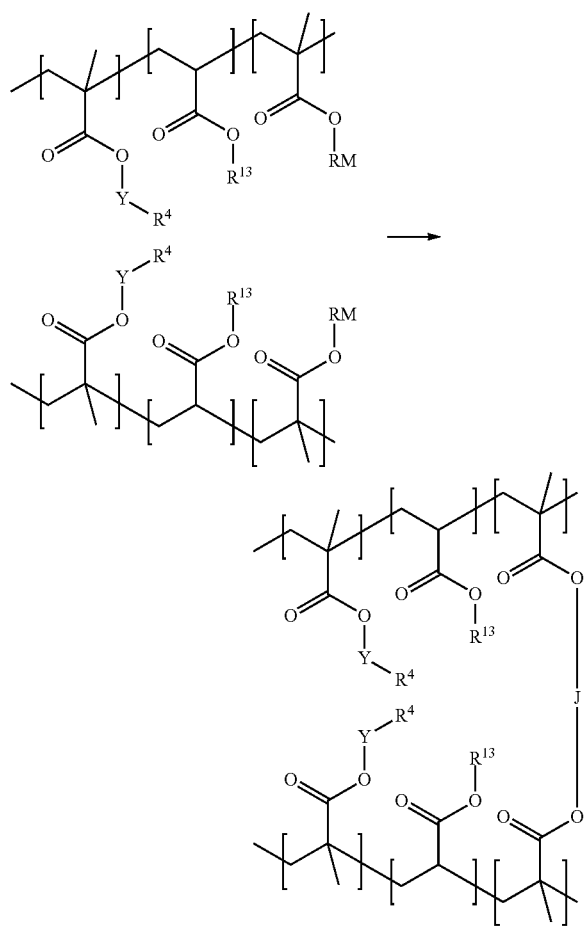

wherein the crosslinking may be accomplished by the use of a chemical reagent, or the formulator may take advantage of special reaction conditions that forms the crosslink.

The compounds that can react with the $R^{20}$ moieties and therefore be used to form the crosslinks, are any compounds capable of reaction with the units to form a J unit as defined herein above.

Non-limiting examples include:
  i) $R^{20}$ units that are —C(O)OH reacting with di-alcohols having the formulae $HO(CH_2)_nOH$ wherein n is from 2 to 20, to form crosslinks having the formulae:

—C(O)O(CH$_2$)$_n$OC(O)—;

ii) $R^{20}$ units that are —C(O)OH reacting with di-amines having the formulae $H_2N(CH_2)_nNH_2$ wherein n is from 2 to 20, to form crosslinks having the formulae:

—C(O)NO(CH$_2$)$_n$NOC(O)—; and iii) $R^{20}$ units that are —NCO reacting with di-amines having the formulae $H_2N(CH_2)_nNH_2$ wherein n is from 2 to 20, to form crosslinks having the formulae:

—NHC(O)NO(CH$_2$)$_n$NHC(O)NH—.

In a fourth category, a linear polymer comprising a plurality of polymer chains is formed as described herein, where the XL group is a photochemical crosslinking group, is exposed to an appropriate wavelength (e.g., 365 nm in the case of a photochemical crosslinking group comprising benzophenone or 300 nm in the case of a photochemical crosslinking group comprising coumarin) resulting in formation of a crosslinked polymer comprising at least one crosslink (e.g., irreversible in the case of a photochemical crosslinking group comprising benzophenone or reversible in the case of a photochemical crosslinking group comprising coumarin). On exposure of a reversibly crosslinked polymer to the appropriate wavelength, the crosslink bond(s) can be broken and the photochemical crosslinking unit reforms its pre-crosslinked state.

Schemes I-III and Examples 1-3 herein below provide examples of the preparation of a hydrogen bonding unit, HB, monomers according to the present disclosure.

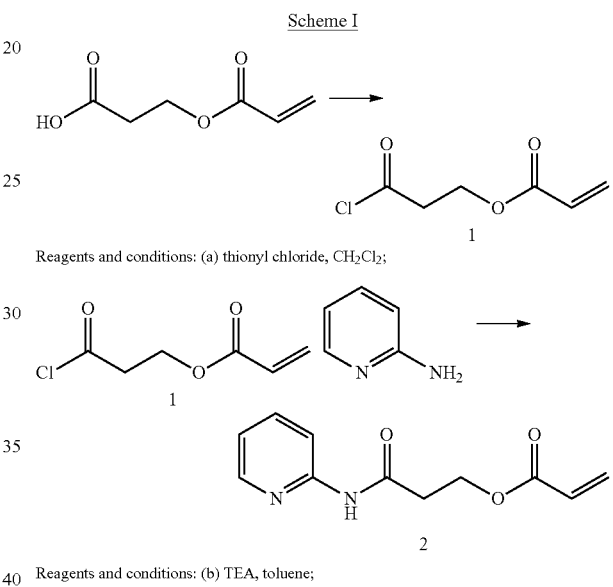

Scheme I

Reagents and conditions: (a) thionyl chloride, CH$_2$Cl$_2$;

Reagents and conditions: (b) TEA, toluene;

Example 1

3-Oxo-3-(pyridin-2-ylamino)propyl acrylate (2)

Preparation of 3-chloro-3-oxopropyl acrylate (1): 2-Carboxyethyl acrylate (1 eq.) is dissolved in CH$_2$Cl$_2$ and the solution is cooled in an ice bath. Thionyl chloride (1 eq.) is added dropwise and the mixture is allowed to warm to room temperature and stir for 4 hours. The solvent is removed under reduced pressure and the desired product is isolated by vacuum distillation.

Preparation of 3-oxo-3-(pyridin-2-ylamino)propyl acrylate (2): 3-Chloro-3oxopropl acrylate, 1, (1 eq.), 2-aminopyridine (1 eg.) and triethylamine (3 eq.) are dissolved in toluene at 0° C. A few crystals of hydroquinone is added to inhibit any polymerization side reactions. The solution is allowed to stir approximately 18 hours at a temperature from about 0° C. to room temperature. The solvent is removed under reduced pressure and the crude material purified over silica. For a more detailed account of this procedure See M. A. Diab, A. Z. El-Sonbati, A. A. El-Sanabori, F. I. Taha *Polymer Degrad. Stab.* 1989, 24, 51, included herein by reference.

Scheme II

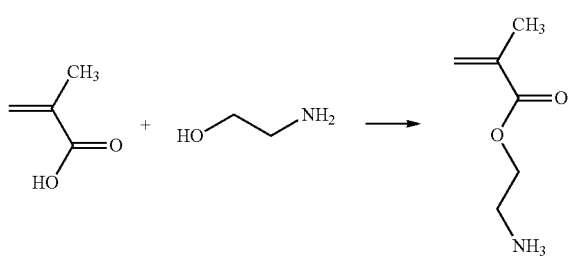

Reagents and conditions: (a) SOCl₂, Cu; 100° C., 2 hr.

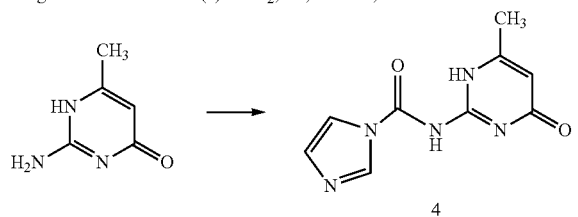

Reagents and conditions: (b) carbonyldiimidazole, DMSO; 60° C., 2 hr.

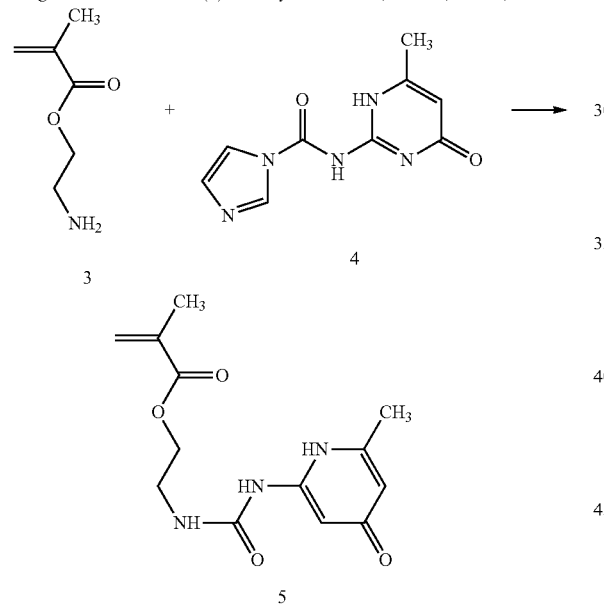

Reagents and conditions: (c) TEA, CHCl₃; 50° C., 4 hr.

Example 2

2-[3-(6-Methyl-4-oxo-1,4-dihydropyridin-2-yl)ureido]etbyl methacrylate (5)

Preparation of 2-amino methacrylate (3): A mixture of ethanolamine hydrochloride (1 eg.) thionyl chloride (1 eg.) and a catalytic amount of Cu powder are heated together to 100° C. Over the next 2 hours methylacrylolyl chloride (2 eq.) is added after which the mixture is cooled to approximately 60° C. and ethyl acetate is added. Crystals may begin to form as the solution cools. The crude product is recrystallized from ethyl acetate/isopropanol to afford the desired product. For a more detailed account of this procedure See J. M. Geurts, C. M. Gottgens, M. A. I. Van Gracfschepe, et. al., *J. of Applied Polymer Science,* 2001, 80, 1401 included herein by reference.

Preparation of N-(6-methyl-4-oxo-1,4-dihydropyrimidin-2-yl)-1H-imidazole-carboxamide (4): A mixture of 6-methylisocytosine (1 eq.) and carbonyldiimidazole (1.5 eq.) were combined in dimethylsulfoxide (DMSO) and the solution was stirred at 60° C. for 2 hours. The mixture was cooled to about room temperature and acetone added after which the desired product precipitated as a white powder that was collected by filtration. The procedure of A. T. Cate, P. Y. W. Dankers, H. Kooijman, A. L. Spek, R. P. Sijbesma, and B. W. Meijer, *J of Am. Chem. Soc.,* 2003, 125, 6860 was followed for this step. The product can be used without further purification.

Preparation of 2-3[(6-methyl-4-oxo-1,4-dihydropyridin-2-yl)ureido]ethyl methacrylate (5): To a solution of 2-amino methacrylate hydrochloride, 3, (1 eq.) and triethylamine (1 eg.) in chloroform (30 mL) is added N-(6-methyl-4-oxo-1,4-dihydropyrimidin-2-yl)-1H-imidazole-1-carboxamide, 4, (1 eq.). The reaction mixture is stirred for 4 hours at 50° C. and the sol vent is removed under reduced pressure. The residue is purified over silica, and the product was obtained by precipitation in methanol. For a more detailed description See A. T. Cate, P. Y. W. Dankers, H. Kooijman, A. L. Spek, R. P. Sijbesma, and E. W. Meijer, *J of Am. Chem. Soc.,* 2003, 125, 6860 include herein by reference.

Scheme III

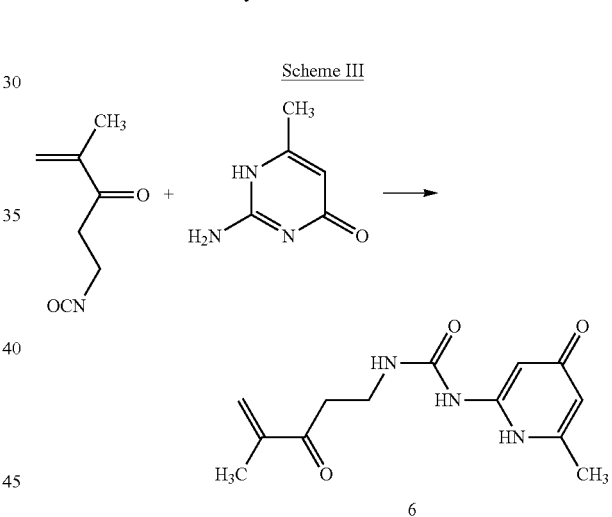

Reagents and conditions: (a) DMSO; 130° C., 1 min.

Example 3

1-(4-Methyl-3-oxopeny-4-enyl)-3-(6-methyl-4-oxo-1,4-dihydropyridin-2-yl)urea [UPy-EA](6)

Preparation of 1-(4-Methyl-3-oxopeny-4-enyl)-3-(6-methyl-4-oxo-1,4dihydropyridin-2-yl)urea [UPy-EA] (6): The procedure of K. Yamauchi; J. R. Lizotte; T. E. Long. *Macromolecules* 2003, 36, 1083-1088, included herein by reference, was followed for the preparation of the title compound, that is summarized herein below. 6-Methylisocytosine (1.25 g, 10.0 mmol) was dissolved in DMSO (10 mL) at 130° C., 2-isocyanatoethyl methacrylate (available from Aldrich Chemical Co.) (1.70 g, 11.0 mmol) was added. In less than 1 min, the mixture was quenched by a water bath. The precipitated white solid was filtered and washed with hexane. Yield ~70%.

The following Scheme IV and Example 4 illustrate the preparation of a shape memory polymer according to the present disclosure.

Scheme IV

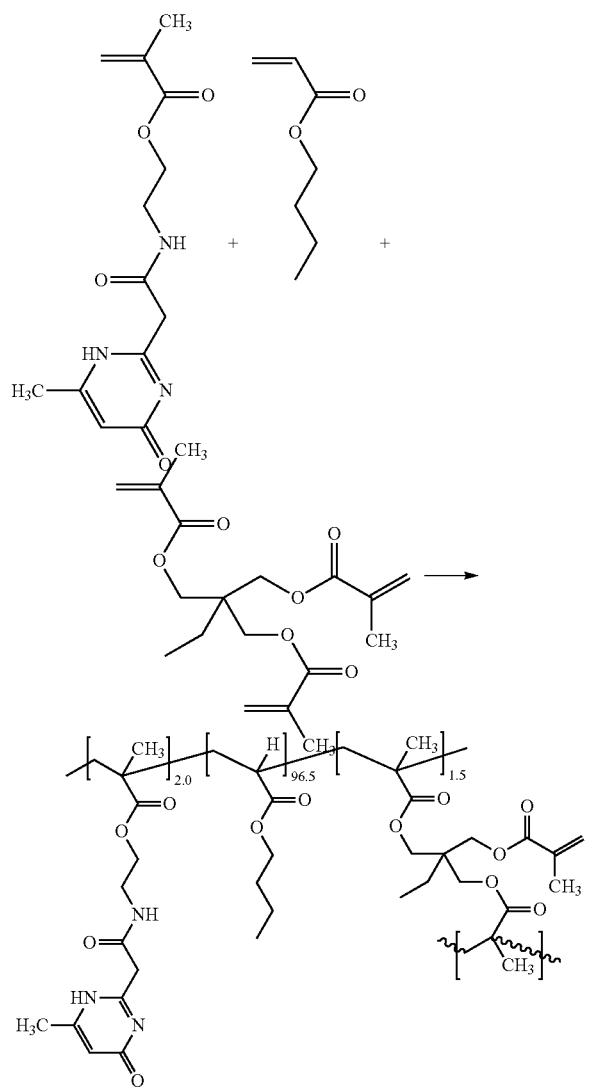

7

Reaction conditions (a): AIBN, NMP; 65° C., 12 hr.

Example 4

[Butyl acrylate]$_{96.5}$[trimethylolpropane trimethacrylate]$_{1.5}$[UPy-EA]$_{2.0}$ Preparation of Butyl acrylate]$_{96.5}$[trimethylolpropane trimethacrylate]$_{1.5}$[UPy-EA]$_{2.0}$ (7): To a reaction vessel was charged butyl acrylate (96.5 mol %), trimethylol-propane trimethacrylate (1.5 mol %), and 1-(4-Methyl-3-oxopeny-4-enyl)-3-(6-methyl-4-oxo-1,4dihydropyridin-2-yl)urea, 7, (2.0 mol %) were combined with N-methyl-pyrrolidinone (50% by wt.) at room temperature. Nitrogen gas was bubbled through the reaction mixture for 30 minutes. Azobisisobutylnitrile [AIBN] (1.0 mmol) was added and the reaction mixture injected onto a Petri dish inside a custom built gas-tight, bell-jar apparatus. The temperature of the reaction was controlled at 65° C. while the reaction apparatus was continuously purged nitrogen during the course of the reaction. After 12 hours the reaction apparatus is cooled and the memory polymer is dried for 48 hours.

The following is an example of another iteration of the polymer outlined in Scheme IV.

Example 5

[Butyl acrylate]$_{97.5}$[trimethylolpropane trimethacrylate]$_{1.5}$[UPy-EA]$_{1.0}$ Preparation of [Butyl acrylate]$_{96.5}$[trimethylolpropane trimethacrylate]$_{1.5}$[UPy-EA]$_{2.0}$ (7): To a reaction vessel was charged butyl acrylate (97.5 mol %), trimethylol-propane trimethacrylate (1.5 mol %), and 1-(4-Methyl-3-oxopeny-4-enyl)-3-(6-methyl-4-oxo-1,4-dihydropyridin-2-yl)urea, 7, (1.0 mol %) were combined with N-methyl-pyrrolidinone (50% by wt.) at room temperature. Nitrogen gas was bubbled through the reaction mixture for 30 minutes. Azobisisobutylnitrile [AIBN] (1.0 mmol) was added and the reaction mixture injected onto a Petri dish inside a custom built gas-tight, bell-jar apparatus. The temperature of the reaction was controlled at 65° C. while the reaction apparatus was continuously purged with nitrogen during the course of the reaction. After 12 hours the reaction apparatus is cooled and the resulting shape memory polymer is dried for 48 hours.

The following are non-limiting examples of shape memory polymers according to the present disclosure.

| | 1$^{st}$ Iteration | |
|---|---|---|
| HB monomer | Q moiety | R$^4$ |
| CH$_2$=C(CH$_3$)Q | —CO$_2$(CH$_2$)$_2$NHC(O)NHR$^4$ | 6-methylpyrimidin-4-(1H)-on-2-yl |
| MOD monomer | R$^{11}$ | R$^{13}$ |
| CH$_2$=CHR$^{11}$ | —CO$_2$R$^{13}$ | n-butyl |
| XL monomer | R$^{16}$ | J |
| CH$_2$=C(CH$_3$)R$^{16}$ | —C(O)OCH$_2$JCH$_2$OC(O)— | —C(C$_2$H$_5$)[CH$_2$O$_2$CC(=CH$_2$)CH$_3$]— |

| No. | MOD mol % | HB mol % | XL mol % |
|---|---|---|---|
| 1 | 96.5 | 1.0 | 2.5 |
| 2 | 97.0 | 1.0 | 2.0 |

-continued

1st Iteration

| | | | |
|---|---|---|---|
| 3 | 96.5 | 2.0 | 1.5 |
| 4 | 97.0 | 2.0 | 1.0 |

2nd Iteration

| HB monomer | Q moiety | $R^4$ | |
|---|---|---|---|
| $CH_2$=$C(CH_3)Q$ | —$CO_2(CH_2)_3NHC(O)NHR^4$ | 6-methylpyrimidin-4-(1H)-on-2-yl | |
| MOD monomer | $R^{11}$ | $R^{13}$ | |
| $CH_2$=$CHR^{11}$ | —$CO_2R^{13}$ | n-butyl | |
| XL monomer | $R^{16}$ | J | |
| $CH_2$=$C(CH_3)R^{16}$ | —$C(O)OCH_2JCH_2OC(O)$— | —$C(C_2H_5)[CH_2O_2CC(=CH_2)CH_3]$— | |

| No. | MOD mol % | HB mol % | XL mol % |
|---|---|---|---|
| 5 | 96.5 | 1.0 | 2.5 |
| 6 | 97.0 | 1.0 | 2.0 |
| 7 | 96.5 | 2.0 | 1.5 |
| 8 | 97.0 | 2.0 | 1.0 |

3rd Iteration

| HB monomer | Q moiety | $R^4$ | |
|---|---|---|---|
| $CH_2$=$C(CH_3)Q$ | —$CO_2(CH_2)_4NHC(O)NHR^4$ | 6-methylpyrimidin-4-(1H)-on-2-yl | |
| MOD monomer | $R^{11}$ | $R^{13}$ | |
| $CH_2$=$CHR^{11}$ | —$CO_2R^{13}$ | n-butyl | |
| XL monomer | $R^{16}$ | J | |
| $CH_2$=$C(CH_3)R^{16}$ | —$C(O)OCH_2JCH_2OC(O)$— | —$C(C_2H_5)[CH_2O_2CC(=CH_2)CH_3]$— | |

| No. | MOD mol % | HB mol % | XL mol % |
|---|---|---|---|
| 9 | 96.5 | 1.0 | 2.5 |
| 10 | 97.0 | 1.0 | 2.0 |
| 11 | 96.5 | 2.0 | 1.5 |
| 12 | 97.0 | 2.0 | 1.0 |

4th Iteration

| HB monomer | Q moiety | $R^4$ | |
|---|---|---|---|
| $CH_2$=$C(CH_3)Q$ | —$CO_2(CH_2)_2C(O)NHR^4$ | 6-methylpyrimidin-4-(1H)-on-2-yl | |
| MOD monomer | $R^{11}$ | $R^{13}$ | |
| $CH_2$=$CHR^{11}$ | —$CO_2R^{13}$ | n-butyl | |
| XL monomer | $R^{16}$ | J | |
| $CH_2$=$C(CH_3)R^{16}$ | —$C(O)OCH_2JCH_2OC(O)$— | —$C(C_2H_5)[CH_2O_2CC(=CH_2)CH_3]$— | |

| No. | MOD mol % | HB mol % | XL mol % |
|---|---|---|---|
| 13 | 96.5 | 1.0 | 2.5 |
| 14 | 97.0 | 1.0 | 2.0 |
| 15 | 96.5 | 2.0 | 1.5 |
| 16 | 97.0 | 2.0 | 1.0 |

5th Iteration

| HB monomer | Q moiety | $R^4$ | |
|---|---|---|---|
| $CH_2$=$C(CH_3)Q$ | —$CO_2(CH_2)_2NHC(O)NHR^4$ | pyridin-2-yl | |
| MOD monomer | $R^{11}$ | $R^{13}$ | |
| $CH_2$=$CHR^{11}$ | —$CO_2R^{13}$ | n-butyl | |
| XL monomer | $R^{16}$ | J | |
| $CH_2$=$C(CH_3)R^{16}$ | —$C(O)OCH_2JCH_2OC(O)$— | —$C(C_2H_5)[CH_2O_2CC(=CH_2)CH_3]$— | |

| No. | MOD mol % | HB mol % | XL mol % |
|---|---|---|---|
| 17 | 96.5 | 1.0 | 2.5 |
| 18 | 97.0 | 1.0 | 2.0 |

-continued

| | 5th Iteration | | |
|---|---|---|---|
| 19 | 96.5 | 2.0 | 1.5 |
| 20 | 97.0 | 2.0 | 1.0 |

6th Iteration

| HB monomer | Q moiety | $R^4$ |
|---|---|---|
| $CH_2=C(CH_3)Q$ | $-CO_2(CH_2)_3NHC(O)NHR^4$ | pyridine-2-yl |
| MOD monomer | $R^{11}$ | $R^{13}$ |
| $CH_2=CHR^{11}$ | $-CO_2R^{13}$ | n-butyl |
| XL monomer | $R^{16}$ | J |
| $CH_2=C(CH_3)R^{16}$ | $-C(O)OCH_2JCH_2OC(O)-$ | $-C(C_2H_5)[CH_2O_2CC(=CH_2)CH_3]-$ |

| No. | MOD mol % | HB mol % | XL mol % |
|---|---|---|---|
| 21 | 96.5 | 1.0 | 2.5 |
| 22 | 97.0 | 1.0 | 2.0 |
| 23 | 96.5 | 2.0 | 1.5 |
| 24 | 97.0 | 2.0 | 1.0 |

7th Iteration

| HB monomer | Q moiety | $R^4$ |
|---|---|---|
| $CH_2=C(CH_3)Q$ | $-CO_2(CH_2)_4C(O)NHR^4$ | pyridin-2-yl |
| MOD monomer | $R^{11}$ | $R^{13}$ |
| $CH_2=CHR^{11}$ | $-CO_2R^{13}$ | n-butyl |
| XL monomer | $R^{16}$ | J |
| $CH_2=C(CH_3)R^{16}$ | $-C(O)OCH_2JCH_2OC(O)-$ | $-C(C_2H_5)[CH_2O_2CC(=CH_2)CH_3]-$ |

| No. | MOD mol % | HB mol % | XL mol % |
|---|---|---|---|
| 25 | 96.5 | 1.0 | 2.5 |
| 26 | 97.0 | 1.0 | 2.0 |
| 27 | 96.5 | 2.0 | 1.5 |
| 28 | 97.0 | 2.0 | 1.0 |

8th Iteration

| HB monomer | Q moiety | $R^4$ |
|---|---|---|
| $CH_2=C(CH_3)Q$ | $-CO_2(CH_2)_2C(O)NHR^4$ | pyridin-2-yl |
| MOD monomer | $R^{11}$ | $R^{13}$ |
| $CH_2=CHR^{11}$ | $-CO_2R^{13}$ | n-butyl |
| XL monomer | $R^{16}$ | J |
| $CH_2=C(CH_3)R^{16}$ | $-C(O)OCH_2JCH_2OC(O)-$ | $-C(C_2H_5)[CH_2O_2CC(=CH_2)CH_3]-$ |

| No. | MOD mol % | HB mol % | XL mol % |
|---|---|---|---|
| 29 | 96.5 | 1.0 | 2.5 |
| 30 | 97.0 | 1.0 | 2.0 |
| 31 | 96.5 | 2.0 | 1.5 |
| 32 | 97.0 | 2.0 | 1.0 |

Figure 6:
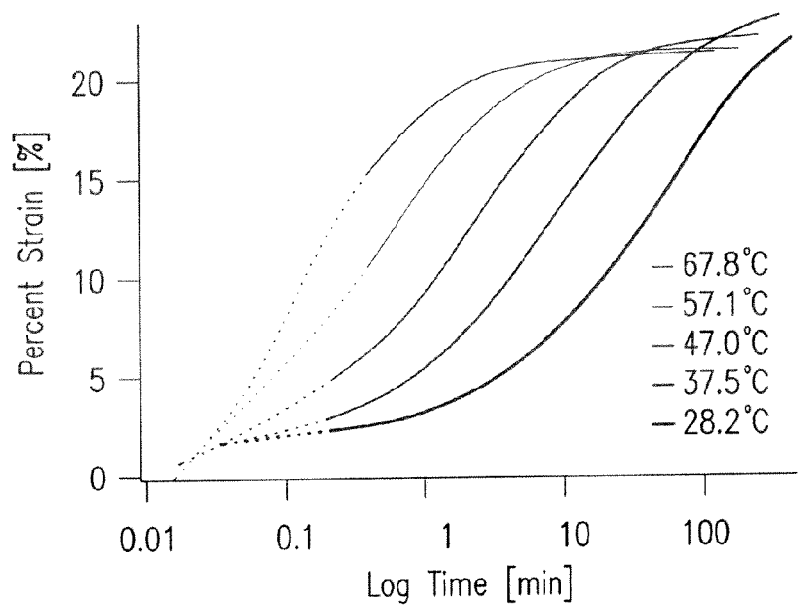
FIG. 6 depicts the percent strain of the polymer of Example 4 at various temperatures over time.

Thermal-mechanical analysis experiments were conducted on the Shape Memory Polymer of Example 4. Experimental data showing typical shape memory responses are shown in FIG. 5. On the left, the solid line indicates percent strain. The sample is initially deformed (approximately 22% strain) at 60° C. using a 50 mN (10 kPa) load. While under load, the temperature (dotted line) is reduced to approximately 5° C., and then the load (dotted line) is removed. The sample is "pinned" in its temporary shape, but slowly recovers. The rate of recovery is accelerated by increasing temperature. Polymers without associating side-groups behave as nearly ideal elastomers. The number of associating side groups present in the polymer influences the time-temperature dependence of shape recovery. To further illustrate this fact, the creep compliance of this polymer is in FIG. 6. The sample is isothermally loaded with a 50 mN load at various temperatures. The data can be collapsed onto a master curve using an appropriate shift factor. These data demonstrate an elastomeric network that is functionalized with a reversibly associating side-group whereby the material has no crystallinity and is well above its glass transition. The architecture of the presently disclosed polymers enables precise fine-tuning of physical properties.

When the disclosed polymers are elastically deformed at a shape memory temperature $T_{SM}$ and subsequently lowered to a shape memory temperature, $T_F$, and the method by which the polymer is elastically deformation is removed, the polymer returns to its original shape at a recovery rate, $R_{REC}$, that is inversely related to the difference in the temperature, $\Delta T_{DEF}$, wherein $\Delta T_{DEF}=T_{SM}-T_F$.

The recovery rate of the shape memory polymers disclosed herein are not always linear over time or over temperature. The formulator can take advantage of this differential recovery rate. In one instance, the formulator can utilize an initial slow shape recovery for embodiments wherein the user needs some amount of time to position and/or adjust the position of the distended polymer. Likewise, in another embodiment, an initial quick recovery rate will allow the polymer to function, for example, in controlling the bleeding of an artery, whereas the slower late recovery rate allows the user to finely adjust the position of the polymer or to cut away unused or unnecessary portions.

The percent strain recovery, $\Delta_{REC}$, at any point along the recovery curve is defined herein as:

$$\Delta_{STRAIN}=S_i-S_t$$

wherein $S_i$, is the initial percent strain and, $S_t$ is the percent strain at time t. Using the solid line curve in FIG. 5, the initial percent strain, $S_i$, is approximately 22% at 50 minutes and the percent strain at about 120 minutes, $S_{120}$, is approximately 17%. Therefore the $\Delta_{STRAIN}$ is 5% at 120 minutes. This corresponds to the polymer recovering approximately 23% of its original form in 70 minutes. Therefore, the rate of recovery over this portion of the curve is approximately 0.33%/minute. Considering the balance of the curve from time 120 minutes to about 140 minutes, the recovery rate over this portion of the curve is approximately 3.9%/minute. The formulator can take advantage of this differential rate of recovery. By manipulation of the polymer backbone and number of crosslinking units, the formulator can adjust the recovery rate to suit any particular application.

The shape memory polymers of the present disclosure have an overall recovery rate, $R_{REC}$, of from about 0.001%/minute to about 100%/minute. One embodiment of the polymers disclosed herein have an overall $R_{REC}$ of from about 0.05%/minute to about 20%/minute. In another embodiment, the polymers disclosed herein have a $R_{REC}$ of from about 0.1%/minute to about 10%/minute. In a further embodiment, the polymers disclosed herein have a $R_{REC}$ of from about 0.5%/minute to about 10%/minute. In still another embodiment, the polymers disclosed herein have a $R_{REC}$ of from about 1%/minute to about 20%/minute. In yet another embodiment, the polymers disclosed herein have a $R_{REC}$ of from about 5%/minute to about 20%/minute.

The shape memory polymers can also have overall recovery rates that include variable recovery rates for portions of the recovery cycle, for example a portion of the overall recovery rate that is slower than the overall recovery rate. In one embodiment of a slower recovery rate, the recovery rate, $R_{REC}$, over at least 10% of the recovery curve, is from about 0.001%/minute to about 5%/minute. In another embodiment of a slower recovery rate, the recovery rate, $R_{REC}$, over at least 10% of the recovery curve, is from about 0.01%/minute to about 1%/minute. In yet another embodiment of a slower recovery rate, the recovery rate, $R_{REC}$, over at least 10% of the recovery curve, is from about 0.1%/minute to about 1%/minute.

The shape memory polymers can also have a faster variable recovery rates for portions of the recovery cycle, for example a portion of the overall recovery rate that is faster than the overall recovery rate. In one embodiment of a faster recovery rate, the recovery rate, $R_{REC}$, over at least 10% of the recovery curve, is from about 1%/minute to about 100%/minute. In another embodiment of a faster recovery rate, the recovery rate, $R_{REC}$, over at least 10% of the recovery curve, is from about 5%/minute to about 75%/minute. In yet another embodiment of a faster recovery rate, the recovery rate, $R_{REC}$, over at least 10% of the recovery curve, is from about 10%/minute to about 50%/minute.

The shape memory polymers of the present invention can be used to form biocompatible devices. For example, shape memory polymers can be used in forming hearing protection. An ear plug formed from a SMP can be deformed at room temperature to over 100% strain, and it returns to its original shape on the order of several minutes after insertion into the ear thereby closing the ear channel and offering a tight, sound reducing ear plug.

Because the human body has a relatively constant temperature, SMP's that have a specific form at body temperature can be elastically deformed at a higher temperature, inserted into the human body, and then returned to their original shape or configuration once equilibrated with the body's temperature. Non-limiting examples of medical uses include stents, sutures, vascular compresses, vascular clips, and the like.

Example 6

Photocrosslinking approaches can be used to prepare shape memory elastomers with reversibly associating hydrogen-bonding side groups. The process involves preparation of linear polymer followed by photocrosslinking. Linear polymers are first prepared that contain both: (i) reversibly associating side-groups or end-groups and (ii) chemically reactive (crosslinkable) side-groups or end-groups. The chemically reactive groups may be photosensitive and, upon irradiation, form covalent crosslinks with other chains. Alternatively, the side-groups may be reactive toward free radicals that are generated or seeded from a photosensitive additive.

Figure 7:
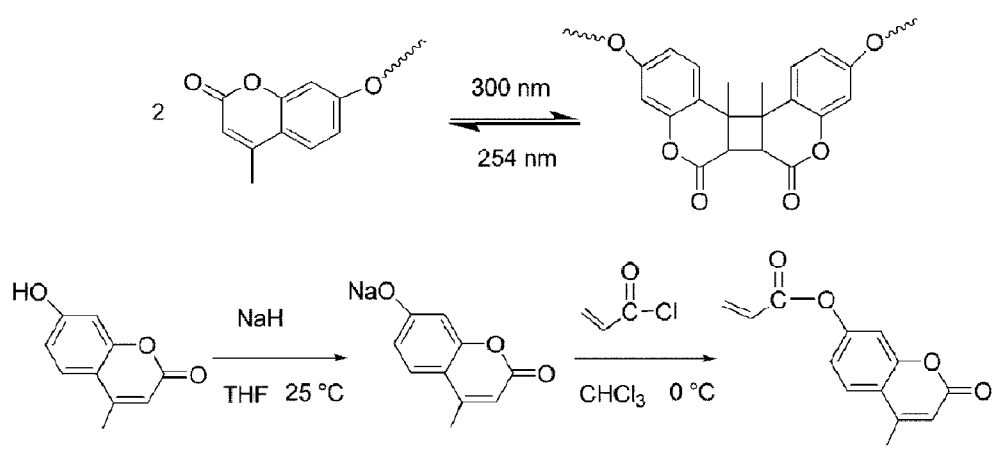
FIG. 7 is an example of reversible covalent bonding of coumarin moieties and example of monomer with photochemical crosslinking group having a coumarin moiety.
Figure 8:
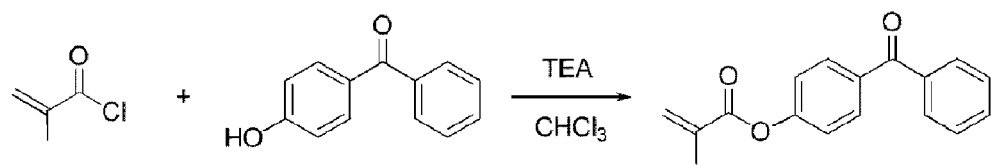
FIG. 8 is an example of a monomer with a photochemical crosslinking group having a benzophenone moiety.

The following provides an example of photocrosslinked shape memory polymers. Poly(butyl acrylate) linear polymers containing self-complementary hydrogen bonding side-groups, (e.g., ureidopyrimidinones (see, e.g., FIG. 7)) and photocrosslinkable side-groups, (e.g., benzophenone (see, e.g., FIG. 8)) were first prepared using conventional free radical polymerization in chloroform. The product polymer was isolated and cast into a film form. Upon exposure to UV light (365 nm) it is considered that the benzophenone side-groups dissociate into free radicals, and the side-group can react with other polymer chains to form covalent crosslinks, resulting in an insoluble polymer network.

There are at least four advantages of using photocrosslinking methods to prepare shape memory elastomers. One, prior to crosslinking, linear polymers can be more fully characterized (e.g., by NMR and GPC) since they can be dissolved into solution. The composition of the network, which is important for developing new formulations, can then be accurately deduced from the composition of the linear polymers. Two, a greater amount of reversibly associating hydrogen bonding group may be incorporated into the polymer network because the polymerization reaction is conducted in solution. Three, the linear polymers can be molded and photo-crosslinked into complex shapes that are defined by a mold or a light pattern. Since solvent does not need to be removed during the crosslinking step, the mold may completely enclose the material and shrinkage can be minimized. Four, intrinsic stress does not develop during solvent removal, and, therefore, the formed polymer network should be near its stress-free state. A stress-free network is expected to have a lower modulus at low strains, and, therefore, is expected to have more pronounced shape memory effects.

Figure 9:
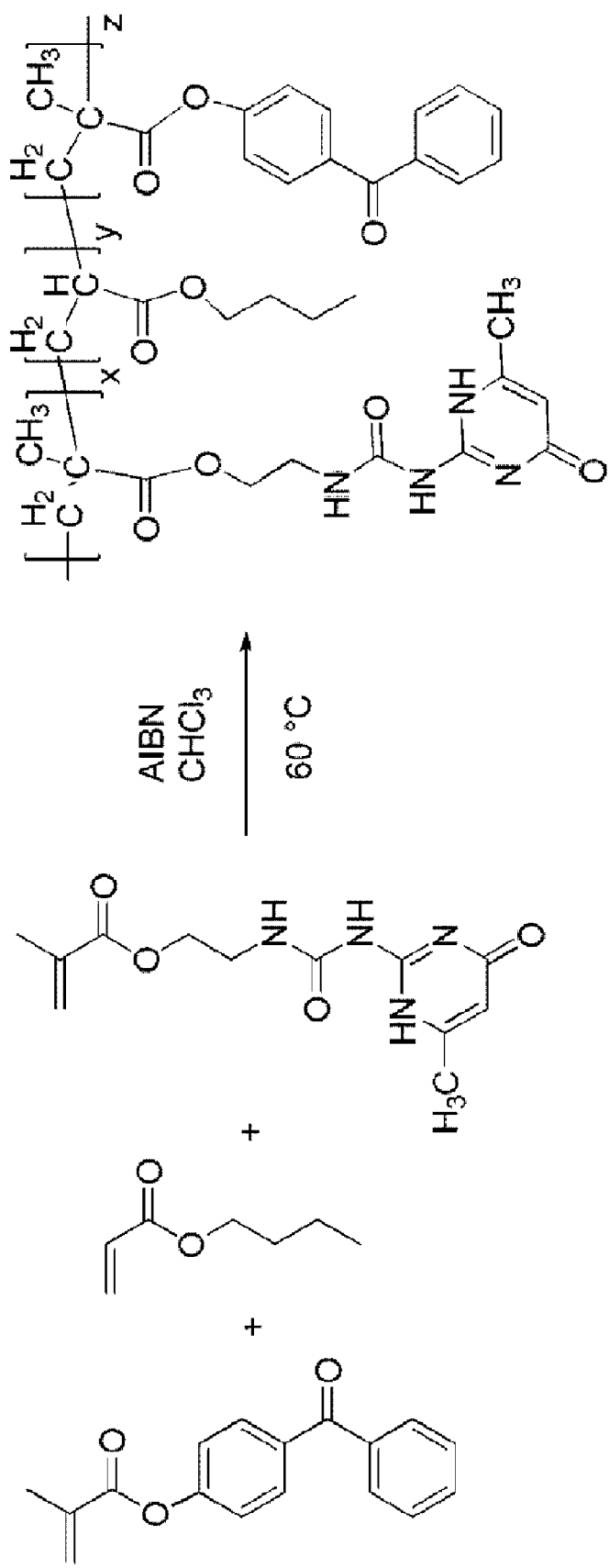
FIG. 9 is an example of polymer with photochemical crosslinking groups.

Synthesis of an example of a benzophenone-containing shape memory polymer (see, e.g., FIG. 9). 4-methacryloyloxy benzophenone monomer. 1.98 g (10 mmol) of 4-hydroxyl benzophenone was dissolved in $CHCl_3$, 1.11 g of triethylamine was also added. Under ice water bath, 1.15 g of methacryloyl chloride was added dropwise. The reaction was kept in ice water bath for 6 hrs. The solution was passed through a short silica gel filter, and the filtrate solution was rotavaporated to give light yellow color product, yield about 90%. The raw product was then further purified via column chromatography.

Copolymer synthesis. Polymer (butyl acrylate) with 1 mol % bezophenone monomer. In an air-free reaction flask, 79 mg (03 mmol) 4-methacryloyloxy benzophenone and 3.84 g (30 mmol) Butyl acrylate were charged. 4.8 mg of azobisisobutyronitrile (AIBN) was added as initiator. 30 ml of $CHCl_3$ was added as solvent. After the mixture was degassed $O_2$ by $N_2$ bubbling for 0.5 hr, the flask was immersed into a 75° C. heating oil bath for a reaction time of 8 hrs. The resulting polymer solution was reprecipitated from $CH_3OH$ to get viscous polymers, yield ~80%.

Polymer (butyl acrylate) with 1 mol % bezophenone monomer and 2 mol % UPy monomer. In an air-free reaction flask, 79 mg (03 mmol) 4-methacryloyloxy benzophenone and 164 mg (0.6 mmol) ureidopyrimidinone ethyl methacrylate and 3.84 g (30 mmol) Butyl acrylate was charged. 4.8 mg of azobisisobutyronitrile (AIBN) was added as initiator. 30 ml of $CHCl_3$ was added as solvent. After the mixture was degassed $O_2$ by $N_2$ bubbling for 0.5 h, the flask was immersed into a 75° C. heating oil bath for a reaction time of 8 hrs. The resulting polymer solution was reprecipitated from $CH_3OH$ to get viscous polymers, yield ~80%.

Curing Procedure. 1 mm thick cured films were produced by spreading prepolymer onto a 1 mm thick quartz slide. The film thickness was maintained by the use of a 1 mm thick PTFE gasket sandwiched between the two quartz slides. To aid in spreading of the high viscosity prepolymer melt, samples were placed on a hot plate with a temperature of 60° C. maintained on the surface. The assembly was then placed into a closed glass vessel, evacuated, and filled with argon gas. Cross linking of the film was carried out at room temperature for 30 mins using a Spectroline® UV-400 Superflood UV™ curing lamp. The intensity of the incident radiation at λ=360 nm was verified to be 19.0+/−05 mW/cm² (as measured through the top surface of the glass enclosure) before and after each exposure to ensure consistent dosage.

Linear photoactive pre-polymers can achieve UPy containing elastomers with benefits such as, for example:
  no UPy content limitation as solvent is needed for the UPy monomer;
  easy purification, linear prepolymers can be easily purified to get rid of unreacted monomers, solvents, and other small molecules;
  simple characterization, linear prepolymers can be readily characterized using solution-based techniques that can not be applied to crosslinked samples. For example, gel permeation chromatography (GPC) and $^1H$ NMR;
  stress free elastomers, subsequent crosslinking will enable stress-free networks to be formed, and will enable the covalent crosslinking density to be systematically tuned.

Figure 10:
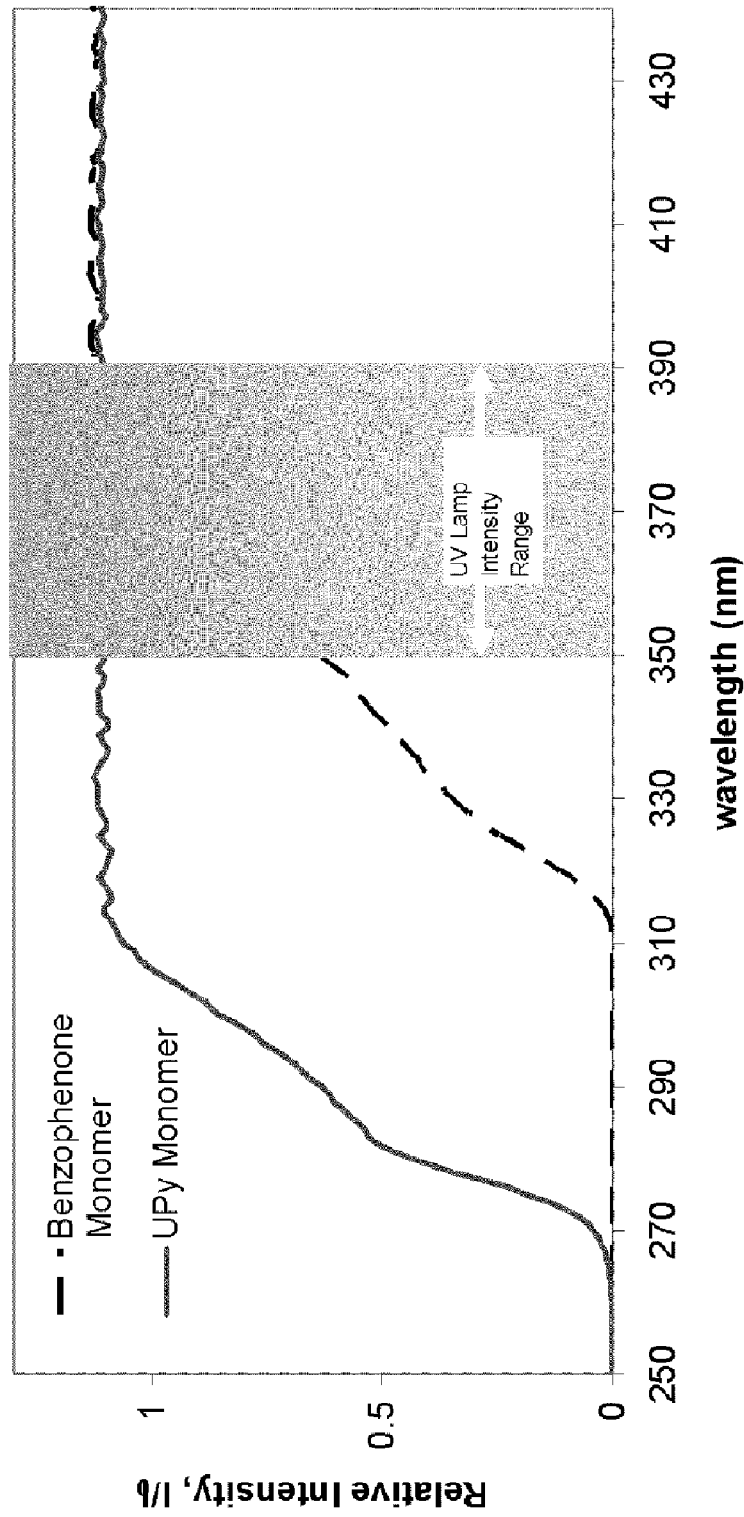
FIG. 10 is an example of absorption characteristics of benzophenone and Upy monomers.

Coumarin chemistry and benzophenone chemistry are two examples of chemistry for formation of photocrosslinkable shape memory polymers (see, e.g., FIG. 10). Both chemistries have been demonstrated to be practical to cure thin polymer films. Both monomer synthesis are simple. An advantage of coumarin chemistry is that it is a reversible process. In order to UV cure bulk polymers, UV penetration depth is an important factor. For example, coumarin chemistry requires two molecules.

Example 7

Crosslinked elastomers containing reversibly-binding side-groups are capable of storing elastic energy on multiple time-scales, giving rise to shape-memory and self-healing properties. Photo-crosslinkable coumarin and benzophenone side-groups were incorporated into linear macromers containing reversible (2-ureido-4-pyrimidinone, UPy) side-groups. The method and resulting polymers enables melt-processing of shape-memory elastomers into complex permanent shapes, and samples can be prepared with much higher UPy-content. UV-Vis spectroscopy was applied to study the efficacy of the crosslinking process. Resulting elastomer networks with variable densities of covalent crosslinks and reversibly associating side-groups were systematically prepared and studied. Dynamic mechanical analysis revealed the presence of two storage modulus plateaus: a high-temperature plateau attributed to covalent crosslinks, and a lower temperature plateau attributed to both reversible and covalent crosslinks. Results also show that dynamic crosslinks behave nearly as effectively as permanent crosslinks below the UPy hydrogen bond transition, and that the presence of a covalent network supports cooperative binding of UPy side-groups.

Elastomers can have macromolecular chains bound together into a network by covalent or non-covalent crosslinks. Crosslinks serve as permanent entanglements, restricting long-range and irreversible chain slippage. When deformed, chains are distorted from their most probable and preferable configurations, giving rise to an entropic restoring force.

A thermoresponsive shape-memory polymer (SMP) is capable of fixing a temporary-shape when cooled, under elastic strain, beneath a well-defined shape-memory temperature ($T_{SM}$) that is often accompanied by crystallization or the formation of a polymer glass. At temperatures beneath $T_{SM}$, the deformed shape is stabilized by the formation of crystalline or glassy domains, and this shape can be maintained indefinitely, even in the absence of stress. However, upon subsequent heating above $T_{SM}$, the SMP can be triggered to revert to its original shape as stored elastic strain-energy is recovered. Compared to shape-memory alloys and ceramics, SMPs are lightweight, relatively inexpensive, and the shape-recovery temperature can be adjusted through modification of polymer structure or architecture. In addition to crystallization and vitrification, dynamic transitions can also be used to stabilize mechanically deformed elastomers. Reversible hydrogen bonding can stabilize elastically deformed states. For example, poly(butyl acrylate) covalent networks containing 2-ureido-4-pyrimidinone (Upy) side-groups have been synthesized. The UPy group contains a linear array of four hydrogen bonding groups and undergoes self-dimerization with extraordinarily high solution dimerization constants ($K_{dim}$ $10^7$~$M^{-1}$ in $CDCl_3$). A unique feature of these networks containing UPy side-groups is that the rate of shape-recovery is adjustable and depends on temperature and the density of associating sidegroups. Moreover, the materials behave as elastomers both above and below the shape-memory transition temperature. Creep and rheology experiments of these and similar dynamic networks show Arrhenius-like temperature dependence, suggesting that mechanical relaxation is controlled by the rate of H-bond dissociation. The integration of hydrogen bonding groups into soft materials has been extended to titan-mimicking modular polymers and the concept of introducing both reversible and covalent crosslinks has been applied to improve stress relaxation of coatings below the glass transition temperature.

Figure 11:
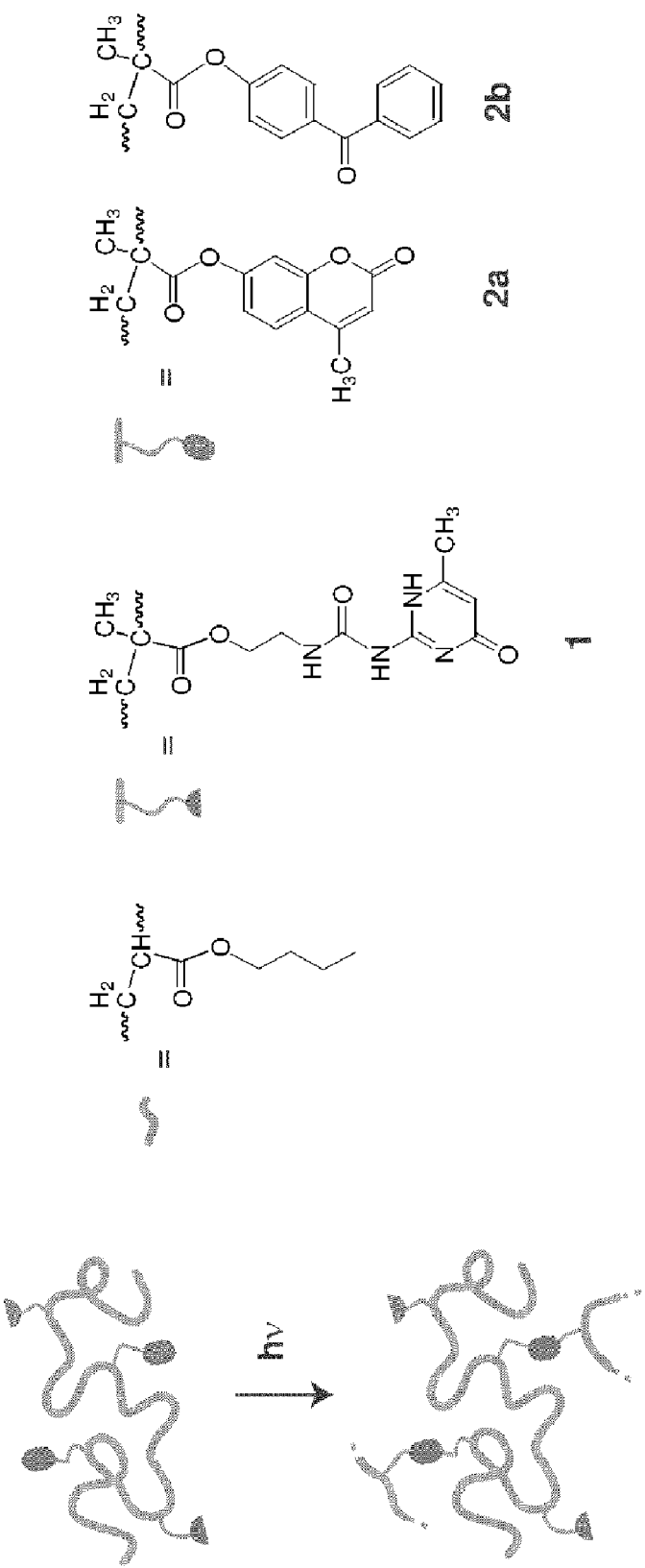
FIG. 11 is a scheme illustrating photo-crosslinking of network precursors to form dynamic networks containing both covalent (e.g., irreversible) and reversibly-associating crosslinks.

In this example, a method of preparing shape-memory networks that utilize reversible association to temporarily stabilize mechanically deformed states is demonstrated. A series of linear polymer melts containing different amounts of reversibly associating UPy-groups and photocrosslinkable side-groups were synthesized and crosslinked using UV light (see FIG. 11). This approach offers several advantages over the previously reported reactive-casting method. Since linear polymers are prepared in solution, a greater density of hydrogen bonding side groups can be introduced into polymer networks, and more pronounced shape-memory effects are expected. Prior to crosslinking, linear polymers can be chemically characterized to properly deduce the composition of resulting networks. Network precursors can be molded into complex shapes that are defined by a transparent mold or a light pattern. Furthermore, since solvent removal is avoided, the network is formed near the stress-free state.

In this example, two different photosensitive monomers were synthesized: one containing coumarin (2a) and the other containing benzophenone (2b). Coumarin dimerizes upon exposure to UV light to form covalent crosslinks (a bimolecular process), whereas benzophenone undergoes photolysis upon irradiation (a unimolecular process) followed by hydrogen extraction to form crosslinks. This example describes the efficacy of photo-crosslinking and the physical properties of formed networks. The resulting dynamic mechanical properties are also discussed and related to the density of permanent and reversible crosslinks with the goal of assessing the degree to which dynamic H-bond interactions act like permanent crosslinks.

Methods

Materials. All chemicals were reagent-grade and used without further purification. Butyl acrylate, 2-isocyonatoethyl methacrylate, azobisisobutyronitrile (AIBN), triethyl amine, and deuterated chloroform ($CHCl_3$) were purchased from Aldrich. 2-amino-4-hydroxy-6-methylpyrimidine and methacryloyl chloride were purchased from Alfa Aesar. Solvents N-methylpyrrolidone (NMP), methanol, and dimethyl sulfoxide (DMSO) were purchased from Alfa Aesar. Solvent tetrahydrofuran (THF), $CHCl_3$ were purchased from J.T. Baker. THF and $CHCl_3$ used in this synthesis were purified using a Pure Solve PS-MD-3 solvent purification system from Innovative Technology.

Polymerization of linear macromers (2a, 2b). Monomers 7-acryloyloxy-4-methyl coumarin, 4-methacryloyloxy Benzophenone, and ureidopyrimidinone ethyl methacrylate were prepared according previously published methods. A typical polymerization procedure to prepare macromer 2a will be briefly described. In an air-free reaction flask, 73 mg (0.3 mmol) of 7-acryloyloxy-4-methyl coumarin, 164 mg (0.6 mmol) of ureidopyrimidinone ethyl methacrylate and 3.84 g (30 mmol) of butyl acrylate were charged. 4.8 mg of azobisisobutyronitrile (AIBN) was added as initiator; and 30 ml of $CHCl_3$ was added as solvent. After the mixture was degassed by $N_2$ bubbling for 0.5 hr, the flask was immersed into a 75° C. oil bath and reacted overnight. The resulting polymer-solution was precipitated in methanol, yielding a viscous liquid, yield=80%. An analogous procedure was followed to prepare macromers 2b using 4-methacryloyloxy benzophenone as a reagent. $^1$H NMR (Bruker 400) was used to determine the chemical compositions of the synthesized macromers. Molecular weight and polydispersity were measured by GPC (Agilent 1100) using THF as an eluent.

Photo-crosslinking and swelling of macromer films. Macromer solutions (~5 wt %, in chloroform) were cast onto quartz slides using a Teflon spacer with a 40×10 mm window. After solvent removal, the thickness of resulting films was about 0.5 mm. Films were placed into vacuum oven and dried overnight at 60° C. Irradiation was conducted in a nitrogen glove box to avoid oxygen inhibition. Samples were irradiated with a UV lamp (UVLM-28) with a measured intensity of 5 mW/cm$^2$ at 365 nm for 10 min increments. After each exposure, samples were held for one hour to ensure free radical intermediates were consumed. The procedure was repeated until free radical intermediates were no longer observed using ultraviolet spectroscopy. Typically this required a total exposure time of 60 min.

Swelling and Gel fraction measurements. Weight and volume were measured in triplicate for 0.5 mm thick specimens with an initial area measuring roughly 5×10 mm. Specimens were individually exposed to 15 ml of isopropyl alcohol (23° C./48 hours) and the sample mass and volume change recorded. Volume-swell is calculated according to the following relationship:

$$Q = 1 + \frac{\rho_p}{\rho_s}\left(\frac{M_{Swell}}{M_{Dry}} - 1\right)$$

where Q is the volume swell (i.e. ratio of volume of swollen polymer to volume of dry polymer), $\rho_s$ and $\rho_p$ are the solvent and polymer densities, respectively, and $M_{Dry}$ and $M_{Swell}$ are the measured masses in the dry and swollen states, respectively. Specimens were subsequently dried in a vacuum oven at 80° C. for 48 hours and weighed to determine gel fraction, expressed as the ratio of the final dry mass to the initial mass.

Dynamic Mechanical Testing. Photo-cured samples were cut into 6 mm×10 mm films, and dynamic mechanical analysis was performed using a solid-state rheometer (Rheometrics, RSA-2). Frequency sweeps from 0.01 to 100 rad/s, at 2% strain, were acquired at temperatures ranging from 30° C. to 100° C. at 10° C. increments. Storage modulus E', loss modulus E" and tan δ were recorded at each experimental/frequency and temperature. Data were analyzed using a commercial software package (TA Orchestrator v7) and time-temperature superposition was performed using a least-squares fitting routine.

Discussion

Synthesis of photo-crosslinkable macromers. The characteristics of synthesized poly(butyl acrylate) macromers containing both UPy and photo-crosslinkable side-groups are summarized in Table 1. The sample name specifies the mol % of the functional monomers in the feed: coumarin (Cm), benzophenone (Bp), and ureidopyrimidinone (UPy). Macromers could be prepared with UPy-contents exceeding 10 mol %, and this is significantly higher than the UPy-content of prior shape memory elastomers (~2 mol %). Statistical copolymer compositions determined using $^1$H NMR, agree fairly well with experimental feed compositions. Molecular weights, determined using SEC, ranged from 38 to 104 kDaltons—note that all copolymers exceed the entanglement molecular weight (~25 kDaltons) of poly(butyl acrylate). The polydispersity indexes shown in Table 1 are lower than expected. It is suspected that this results from the removal of low molecular weight species during reprecipitation. For samples with high UPy-content, the polydispersity index was generally higher. For these samples, the presence of intermolecular UPy-UPy association may preclude the/removal of low molecular weight species.

resulted in photocleavage of dimers and a recurrence of the coumarin absorption peak. The efficiency of photocleavage appeared to decrease from one cycle to the next, with ~60% of the coumarin groups cleaving as compared to the previous cycle.

TABLE 1

Molecular weight and composition of photo-crosslinkable macromers.

| Macromer | Crosslinker content | | UPy content | | $x_x$ | $x_{UPy}$ | $M_n^b$ | $PDI^b$ |
| | Feed (mol %) | Meas.[a] (mol %) | Feed (mol %) | Meas.[a] (mol %) | | | | |
| --- | --- | --- | --- | --- | --- | --- | --- | --- |
| Coumarin-containing | | | | | | | | |
| Cm1 | 1.0 | 1.20 | 0 | 0 | 3.5 | 0 | 38,000 | 1.70 |
| Cm1-UPy2 | 1.0 | 1.30 | 2.0 | 2.2 | 4.0 | 6.7 | 40,000 | 1.65 |
| Benzophenone-containing | | | | | | | | |
| Bp1 | 1.0 | 0.70 | 0 | 0 | 5.6 | 0 | 104,000 | 1.14 |
| Bp1-UPy1 | 1.0 | 0.78 | 1.0 | 0.6 | 5.8 | 4.4 | 96,400 | 1.21 |
| Bp1-UPy2 | 1.0 | 0.77 | 2.0 | 1.7 | 5.9 | 12 | 98,800 | 1.22 |
| Bp1-UPy5 | 1.0 | 1.10 | 5.0 | 6.4 | 3.5 | 19 | 42,500 | 1.82 |
| Bp1-UPy10 | 1.0 | 0.86 | 10.0 | 11.8 | 3.6 | 49 | 61,400 | 1.77 |
| Bp½-UPy2 | 0.5 | 0.54 | 2.0 | 2.1 | 2.6 | 10 | 62,100 | 1.39 |
| Bp2-UPy2 | 2.0 | 1.65 | 2.0 | 2.5 | 5.4 | 8.2 | 43,000 | 1.72 |

[a] 1H NMR,
[b] GPC,
[c] $x_{x1}$, & $x_{UPy}$ refer to average number of photo-crosslinkable (Cm or Bp) and reversibly-binding (Upy) side-groups per macromer chain, respectively.

For coumarin-containing macromers, on average, each copolymer chain contains between 3-4 coumarin moieties; and, for Bp-containing macromers, each copolymer chain contains between 2-6 benzophenone moieties. Only a fraction of available functional groups must be crosslinked to form an incipient gel. In the absence of cycle formation, gelation occurs when the average number of formed crosslinks per primary chain exceeds $p_w/(p_w-1)$ where $p_w$ is the weight average degree of polymerization. For high molecular weight polymers, $p_w$ is large, and, therefore, on average, each chain requires just over one crosslink to form an incipient gel.

Macromer Bp1-UPy10 appeared to be a glassy polymer after precipitation and vacuum-drying. Solvent-casting resulted in stress accumulation and cracking during solvent removal; and macromer Bp1-UPy10 was not photo-crosslinked. Further efforts to prepare quality Bp1-UPy10 films for mechanical testing may involve slow solvent removal and thermal annealing.

Photo-crosslinking of macromer films. Coumarin-containing macromers. The UV-Vis spectrum of a 30 μm-thick film of macromer Cm1 during irradiation (302 nm light, 5 mW/cm$^2$) is displayed in FIG. 12a. Initially, the film exhibited characteristic absorptions at 275 nm and 312 nm. The intensity of both peaks decreased during irradiation. This is consistent with the [2+2] photo-cycloaddition of nearby coumarin side-groups to form cyclobutane dimers. The spectra further indicate that after hours of exposure more than 80% of coumarin side-groups had reacted. In addition, irradiated films were insoluble in chloroform, confirming that chemical crosslinks had formed.

Figure 12:
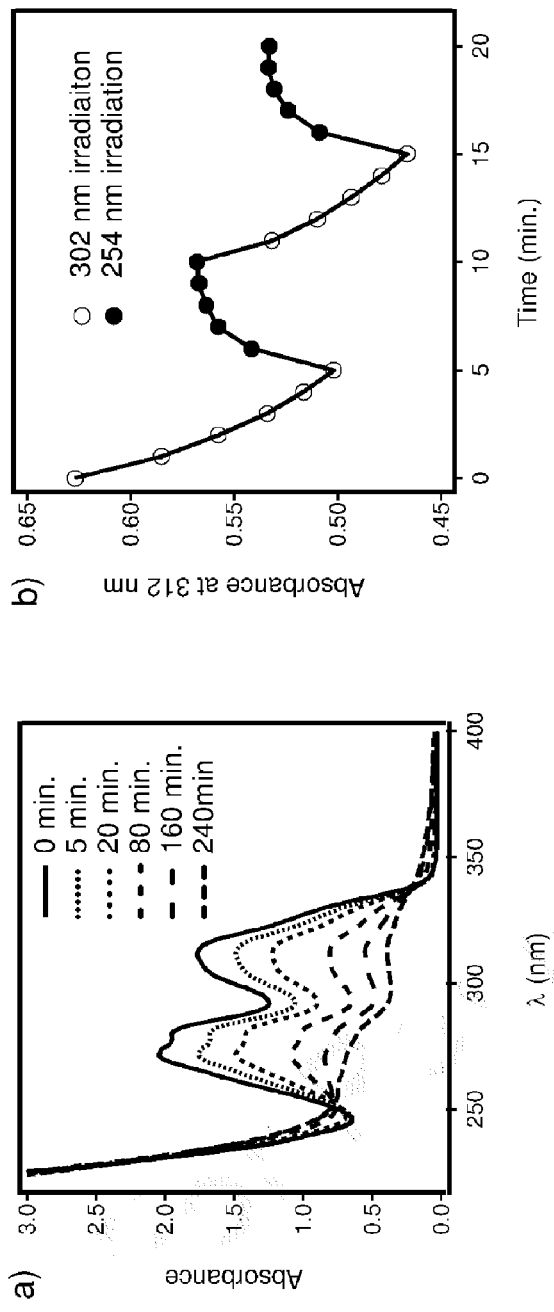
FIG. 12 depicts photo-crosslinking of coumarin-containing macromers: a) UV-Vis spectra of coumarin containing macromer thin film (~30 µm) during irradiation; b) photoreversibilty of coumarin crosslinking in a macromer thin film (~0 µm); the absorbance peak at 312 nm was plotted against UV irradiation time where circles represent 302 nm irradiation, and dots represent 254 nm irradiation; and c) scheme showing photoreversible crosslinking of nearby coumarin side-groups.
Figure 12:
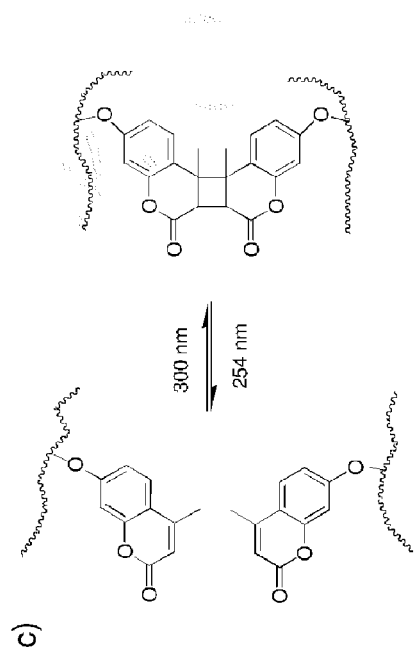

A thin film (~10 μm-thick) was irradiated to test-the reversibility of the coumarin photoreaction. FIG. 12b shows two coumarin addition-cleavage cycles using 302 nm and 254 nm light, respectively. Upon irradiation with 302 nm light, photo-addition occurred, and the coumarin absorption peak decreased. Subsequent irradiation with 254 nm UV light While thin films could be easily crosslinked by UV exposure, efforts to photo-crosslink thick films were unsuccessful. For example, a 500 μm thick film was still not completely crosslinked even after a high dose of UV irradiation (6 hrs at 300-320 nm, 12 mW/cm$^2$). The absorption at 312 nm was nearly that of the uncrosslinked film, and most of the film remained soluble in chloroform. Incomplete curing is attributed to the relatively high molar attenuation coefficient of coumarin ($6\times10^5$ m$^2$/mol, at 312 nm) and, hence, the inability of desired wavelengths to penetrate far enough into the film. An insoluble skin-layer was observed, and this is consistent with incomplete penetration of UV light through the film. In principle, higher doses should fully cure the films, however, at the intensities used in this study, overdosing leads to chemical degradation. Future efforts to photo-cure thick films may involve irradiation at lower intensities over longer times, or the use of higher molecular weight macromers with just enough coumarin side-groups to ensure the formation of a connected network.

The incorporation of both photo-crosslinkable coumarin and UPy side-groups into butyl acrylate elastomers represent an example of light tunable shape-memory elastomers. If coumarin or other photoreversible dimmers are used as the only source of covalent crosslinks, and the UPy groups are used as reversible crosslinks, then the photo-reversibility of coumarin dimerization offers a way to change a shape-memory elastomer's "permanent" shape. For example, irradiation with the longer wavelength can be used to define a material's permanent shape, and irradiation with the shorter wavelength (254 nm) can be used to convert the elastomer back to a deformable melt. If, on the other hand, light-insensitive crosslinks are also present, then the use of both coumarin and UPy side-groups offers two independent, non-interfering mechanisms for shape pinning: temperature and light. This will enable triple-stage shape-memory elastomers that can be fixed by cooling or irradiation and can be recovered by heating or irradiation at a different wavelength.

Benzophenone-containing macromers. Macromers containing benzophenone side-groups were cast into films and irradiated with a lamp measuring 5 mW/cm² at 365 nm. Hydrogen abstraction of benzophenone in polymer matrices has been well studied. Through a two-photon process, the benzophenone group is excited to an nπ* triplet state that abstracts a proton from the surrounding polymer matrix, forming a radical pair. The resulting ketyl radical recombines with the formed radical on the polymer matrix, resulting in a light-absorbing transient (LAT). The LAT has a distinct, long-lived UV absorption signature, and it further reacts to form stable photo-products that are covalently bound to the surrounding polymer matrix.

Figure 13:
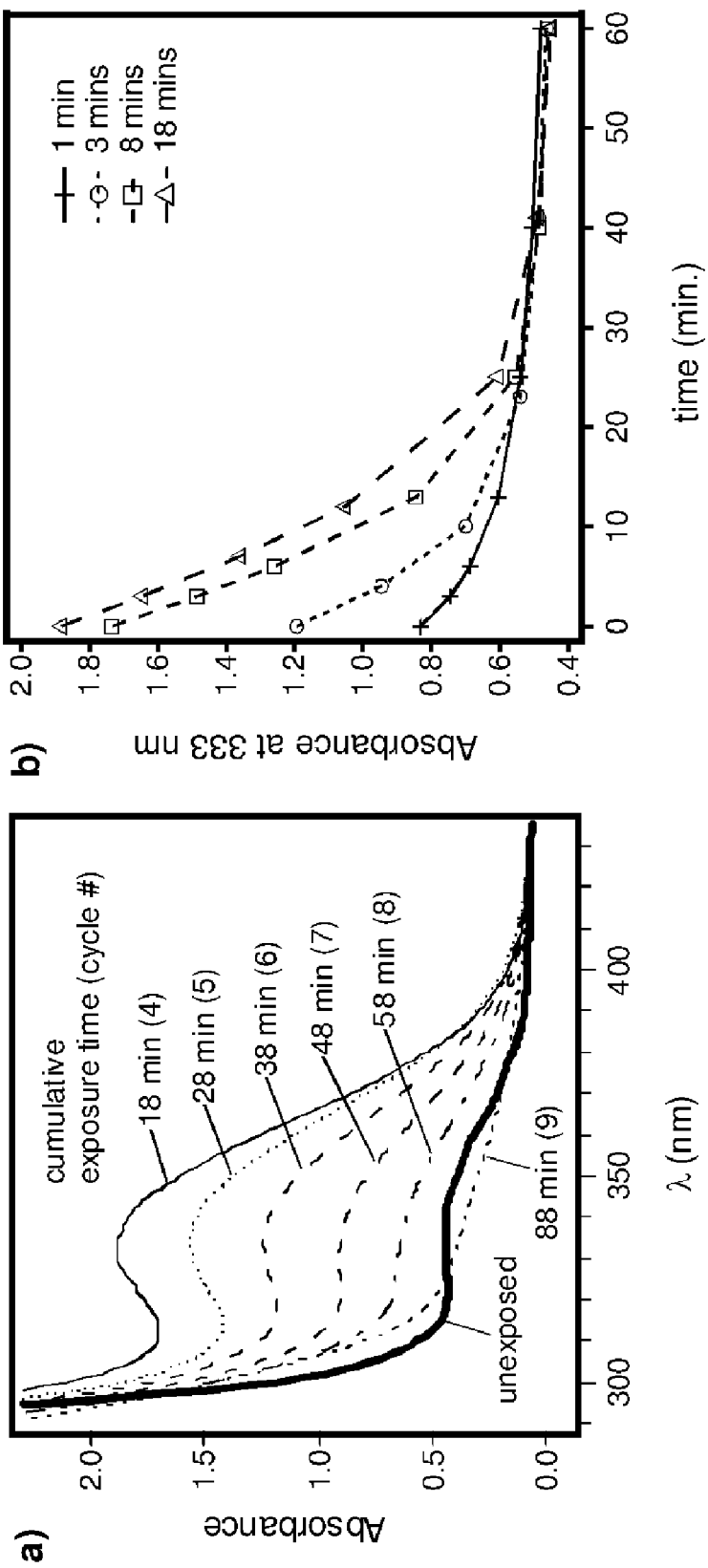
FIG. 13 depicts photo-crosslinking of benzophenone-containing macromer Bp½-UPy2: a) UV-Vis spectra taken immediately after 10 minute periods of UV periods—the absorption a λ=333 nm indicates photo-crosslinking is incomplete; and b) the absorbance maximum (at 333 nm) of the LAT decays following the end of each UV exposure period.

Absorption spectra of macromer films, displayed in FIG. 13, were obtained before and after UV exposures. Exposures were conducted in sequential 1, 2, 5 and 10-minute periods. A characteristic absorption band at 333 nm was observed following exposure and is attributed to the LAT. The molar attenuation coefficient corresponding to the LAT band is 1.2×10⁵ m²/mol, and this is about 4 times that of the initial Bp coefficient. The observed band is similar to earlier reports of free benzophenone in substituted poly(methacrylate)s. Following each exposure, films were held for a minimum of one hour to allow photochemical intermediates to decay into stable photo-products. The decay of the LAT band at 333 nm was studied, and the observed absorbance is plotted against time in FIG. 13b. The half-life of this decay is about 8 minutes, and the rather high rate of decay is attributed to the low rigidity and low microviscosity of the poly(butyl acrylate) network. The initial absorbance of the LAT band decreased following each irradiation period, indicating a reduction in the number of unreacted benzophenone sidegroups. UV exposures (ten minute periods) were repeated until the LAT band was no longer observed, suggesting the film is fully cured. This typically required about eight exposure-decay cycles.

To ensure that UV exposure does not damage the poly(butyl acrylate) backbone, homopolymers were exposed to doses (10-100 J/cm²) well beyond those used to cure benzophenone-containing polymers (~10-30 J/cm²). The molecular weights of irradiated samples-were measured using GPC. Even after an irradiation dose of 100 J/cm², the polymer's number average molecular weight decreased by only about 10%. Additional experimental details and a plot of molecular weight versus irradiation dosage are shown below.

Equilibrium volume-swell and gel fraction of crosslinked elastomers were measured by swelling in isopropanol followed by vacuum drying, and the results are presented in Table 2. Gel fractions all exceeded 90%, indicating the majority of chains were fixed to the crosslinked network. As expected, the gel fraction tended to be higher for samples with a high number of benzophenone side-groups per chain ($x_x$). For example, for Bp1-UPy1, $x_x$=5.8, and for Bp½-UPy2, $x_x$=2.6. The volume swell did not appear to differ significantly for most of the samples investigated. A plot of volume swell versus strand density is provided as Supporting Information.

TABLE 2

Gel fractions of UV-cured elastomers determined from swelling in isopropyl alcohol.

|  | Gel fraction | Q |
|---|---|---|
| Bp1 | 98 ± 1.9 | 2.5 ± 0.17 |
| Bp1-UPy1 | 100 ± 1.7 | 2.5 ± 0.02 |
| Bp1-UPy2 | 98 ± 1.5 | 2.4 ± 0.09 |
| Bp1-UPy5 | 93 ± 1.5 | 1.7 ± 0.04 |
| Bpy½-UPy2 | 91 ± 2.0 | 2.5 ± 0.04 |
| Bp2-UPy2 | 96 ± 2.0 | 1.7 ± 0.06 |

Data reported as mean ± one standard deviation.

Dynamic Mechanical Analysis of Dynamic Networks

Elastic Energy Storage. Photo-crosslinked benzophenone films were subjected to dynamic mechanical analysis. Frequency sweeps were performed at different temperatures, and resulting storage modulus measurements were shifted to yield the master curves shown in FIG. 14. Samples with up to 2 mol % UPy content displayed two distinct plateaus. The lower plateau modulus, observed at low frequencies ($10^{-4}$ to $10^{-2}$ Hz), corresponds to a network of covalent bonds created during photo-crosslinking Evidently, the modulus of this plateau is proportional to the benzophenone content. The upper plateau, observed at higher frequencies (10-10² Hz) corresponds to the overall crosslink density—including both photo-crosslinked net points and reversible net points arising from the UPy dynamic network. The highest storage modulus plateau of about 2.5 MPa was observed for Bp2-UPy2, bearing ~2 mol % of UPy and Bp sidegroups.

At higher UPy-contents, samples exhibited remarkably high storage modulus at all frequencies examined (see FIG. 14b). For example, the storage modulus of Bp1-UPy5 at 1 Hz was about 8 MPa, nearly an order of magnitude higher than samples with lower UPy content at the same conditions. Moreover, the storage modulus for Bp1-UPy5 increased strictly with frequency, over the range studied, and plateaus were not observed.

The classical theory of rubber elasticity can be applied to further understand how covalent and reversible crosslinks affect storage modulus. Affine deformation of an ideal, incompressible elastomer results in a stress given by:

$$\sigma = nRT\left((1+\gamma) - \frac{1}{(1+\gamma)^2}\right) \quad [1]$$

where n is the number of strands per unit volume, R is the gas constant, T is temperature on an absolute scale, and y is strain. In the limit of small strain, Hooke's law is valid, and the ratio of stress to strain (Young's modulus) becomes:

$$E = 3nRT \quad [2]$$

Figure 14:
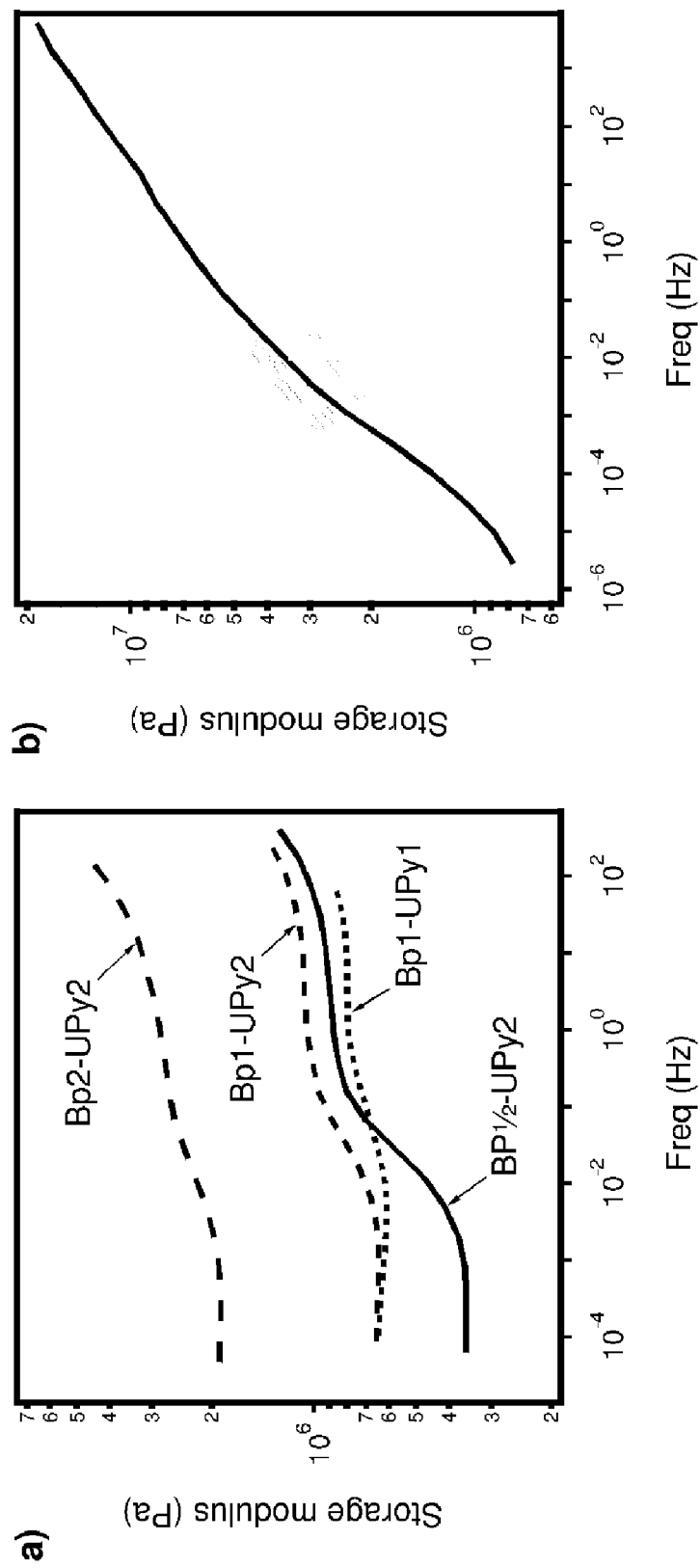
FIG. 14 depicts storage modulus master curves for photo-crosslinked elastomers: a) Bp½-UPy2, Bp1-UPy1, Bp1-UPy2, and Bp2-UPy2; and b) Bp1-UPy5. All data have been time-temperature superimposed to a 60° C. reference temperature.

Thus, neglecting temperature dependence and chain-ends, each plateau modulus in FIG. 14 corresponds to a different strand density n. The strand density corresponding to the lower plateau is plotted against the measured benzophenone concentration, i.e. the maximum possible crosslink density, in FIG. 14b. The data are fairly linear, and a least-squares fit through the origin results in a slope of ~1.4. According to the classical theory of rubber elasticity, if every benzophenone formed a tetrafunctional crosslink, then each crosslink would contribute two new strands to the network, and therefore a slope of two in FIG. 14b is expected. The difference between the observed and theoretical slopes may arise from the following factors: (1) chain ends, which do not contribute to stored elastic energy, are present but are neglected; (2) chain connectivity is ignored; and (3) not all benzophenone sidegroups may have reacted to form interchain crosslinks. In light of these considerations, the data confirm that, upon irradiation, benzophenone groups successfully form chemical crosslinks that influence mechanical properties in an expected and predictable way.

Figure 15:
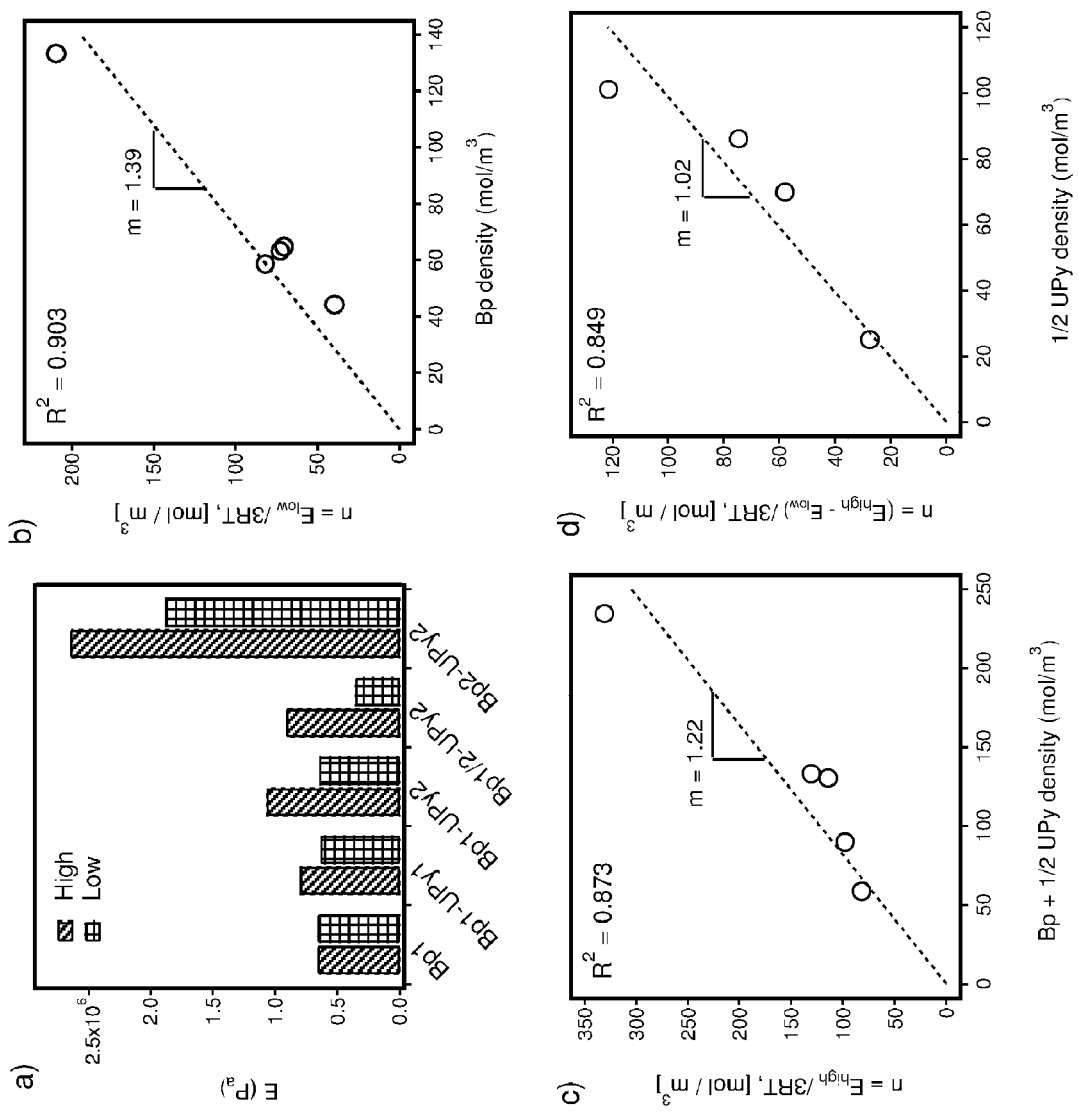
FIG. 15 depicts the relationship between plateaus in storage modulus and the composition of examples of photo-crosslinked elastomers: a) bar chart comparison between high and low plateaus of storage modulus for different compositions; b) plot of strand density obtained from high temperature plateau modulus versus concentration of permanent crosslinks based on Bp content; c) plot of strand density obtained from low temperature plateau modulus versus total crosslink density based on Bp and UPy content; and d) plot of strand density attributed to UPy net-points versus UPy crosslink density.

To examine whether reversible crosslinks also behave as net points, the strand density corresponding to the upper plateau modulus is plotted against the overall crosslink density in FIG. 15c. Since two UPy groups can dimerize to form a single interchain crosslink, the overall crosslink density is taken as the sum of the density of Bp side-groups and one-half the density of UPy side-groups. This choice of the abscissa results in a least-squares slope of 1.22 and a coefficient of determination of $r^2$=0.87. If the same-strand density is plotted against Bp density alone or UPy density alone the data are less correlated ($r^2$=0.85 and 0.46, respectively). Thus, the data indicate that reversible crosslinks are behaving like irreversible crosslinks at these time scales.

The fact the slope in FIG. 15c is less than that in FIG. 15b indicates that UPy dynamic crosslinks are not as effective as Bp permanent crosslinks. To further isolate the effectiveness of UPy crosslinks, the data in FIG. 15c were corrected by subtracting strand density contributions from permanent crosslinks. FIG. 15d displays the corrected strand density that is attributed to only UPy net-points versus UPy crosslink density. Least squares fitting results in a slope of 1.02, and, comparing this to the slope in FIG. 15b suggests that, UPy crosslinks are about 70% as effective as covalent crosslinks at these concentrations. Furthermore, the data in FIG. 15d are not linear. The slope increases with increasing UPy-content, indicating that UPy crosslinks become more effective by increasing their concentration. This effect is attributed to cooperative dynamics, as will be discussed later.

Figure 16:
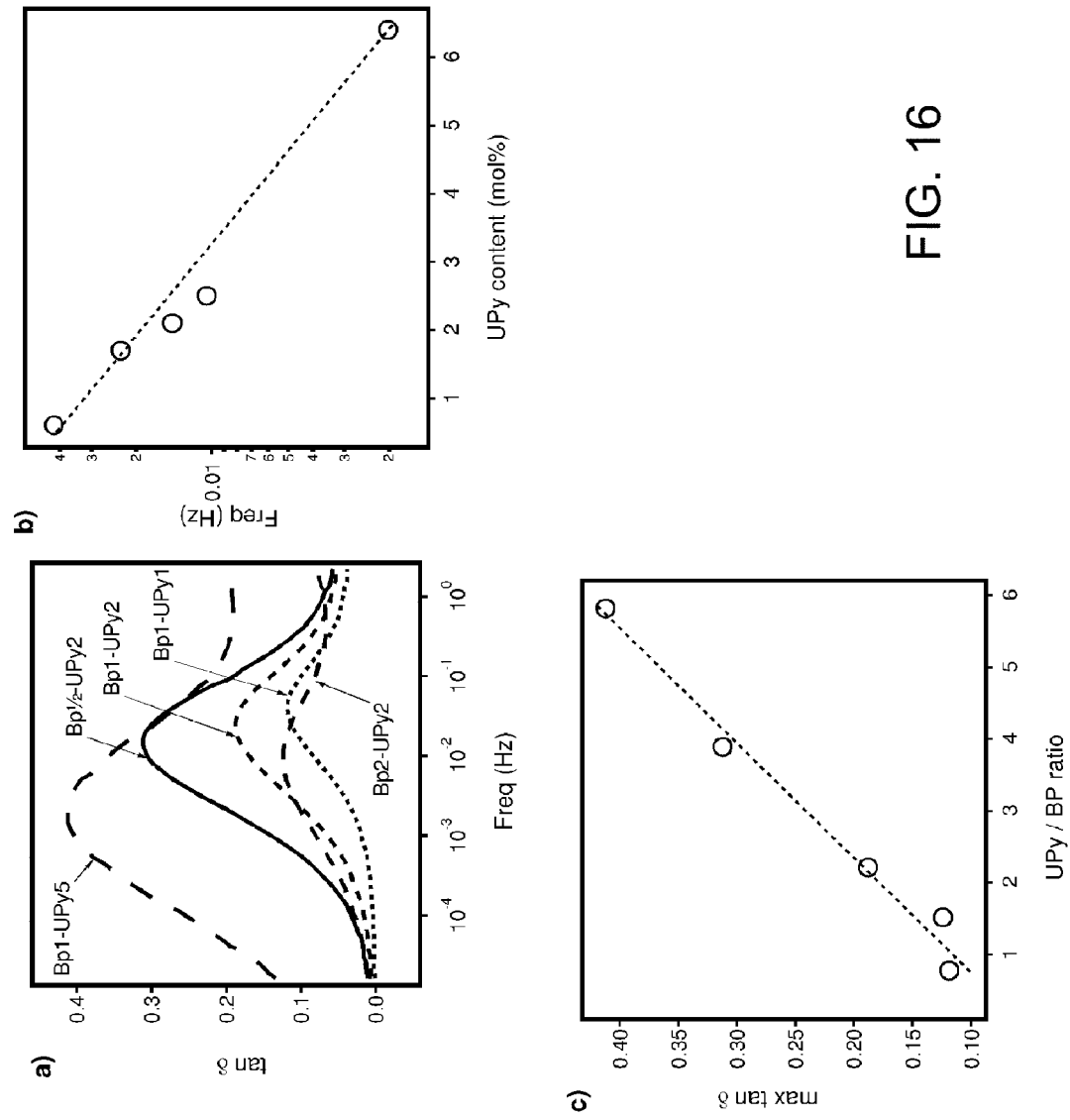
FIG. 16 depicts the influence of UPy-content on damping properties of photo-crosslinked elastomers: a) tan δ master curves (using a reference temperature of 60° C.) of elastomers with different compositions, b) tan δ peak frequency (at 60° C.) vs. UPy content, and c) the magnitude of the peak in tan δ versus the ratio of reversible to chemical crosslinks.

Viscous Dissipation of Energy. In addition to the enhancement of the storage modulus, UPy side-groups also significantly impact the materials' damping properties. FIG. 16 shows time-temperature superimposed tan δ peaks for all photo-crosslinked samples containing UPy sidegroups. Both the magnitude and peak frequency of the loss-tangent depend on UPy-content.

As UPy-content increases, the damping peak shifts to lower frequencies (FIG. 16b). At high frequencies less damping occurs because UPy dissociation events are too slow compared to the imposed strain frequency. At low frequencies the opposite occurs, and UPy bond dynamics are too fast to store and dissipate energy. The maximum viscous dissipation of energy occurs when the rate of chain relaxation, influenced by H-bond dynamics, nearly matches the experimental frequency. This frequency is nearly coincident with the inflection point of the storage modulus curves in FIG. 14. Prior studies have indicated that H-bonding events in transient networks are correlated, resulting in slower dynamics for networks with higher concentrations of associating groups. The correlated dynamics of UPy binding may explain the shift in the loss-tangent to lower frequencies with increasing UPy content observed in this study.

FIG. 16c indicates that the magnitude of the loss-tangent peak is proportional to the molar ratio of UPy to Bp functional groups. UPy hydrogen bond dynamics influence the rate of chain relaxation by providing an additional mechanism to absorb energy. Enhanced frictional energy loss is attributed to continuous breaking and reforming of hydrogen bonds during the chain relaxation process giving rise to the observed relationship between tan δ and the number density of UPy groups. On the other hand, an increase in Bp concentration will yield an increase in storage modulus, which serves to reduce tan δ at a given UPy concentration. The ability of the UPy-groups to increase material stiffness while also increasing the level of viscous energy dissipation provides an exception to the engineering trade-off between material stiffness and loss.

Figure 17:
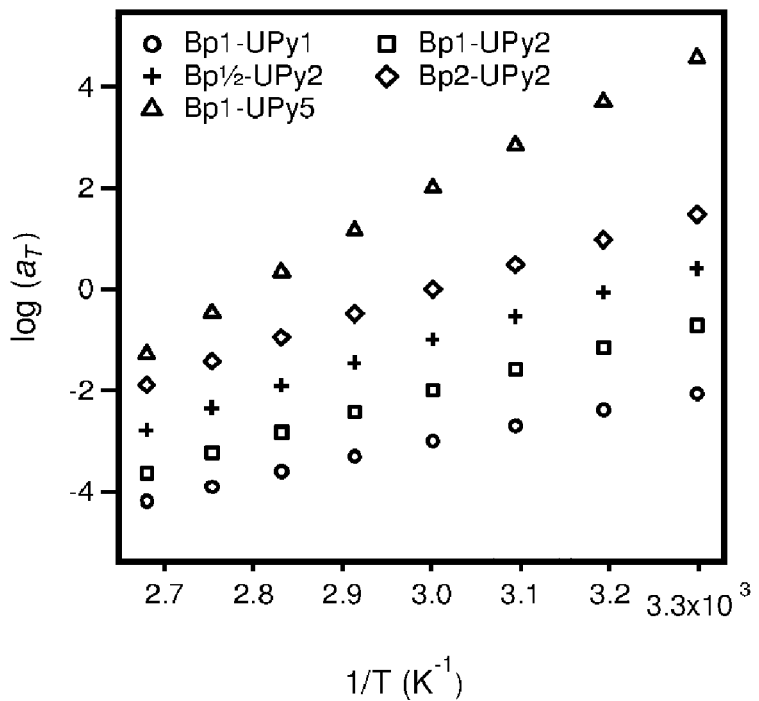
FIG. 17 depicts shift factors for UPy-containing elastomers determined from time-temperature superposition of storage modulus using a reference of 60° C. Data sets were shifted vertically to avoid overlap.

Cooperativity of UPy Dynamics. UPy bond dissociation leading to mechanical stress relaxation is a thermally-activated process that exhibits an Arrhenius-dependence on temperature. FIG. 17 shows how the shift factor, obtained when superimposing storage modulus-curves, depends on inverse temperature for each dynamic network. As expected, the data are linear, confirming that UPy-dissociation leads to a loss of elastically stored energy and is thermally-activated. The observed linearity is consistent with that observed in melts of random and triblock copolymers containing UPy side-groups.

Figure 18:
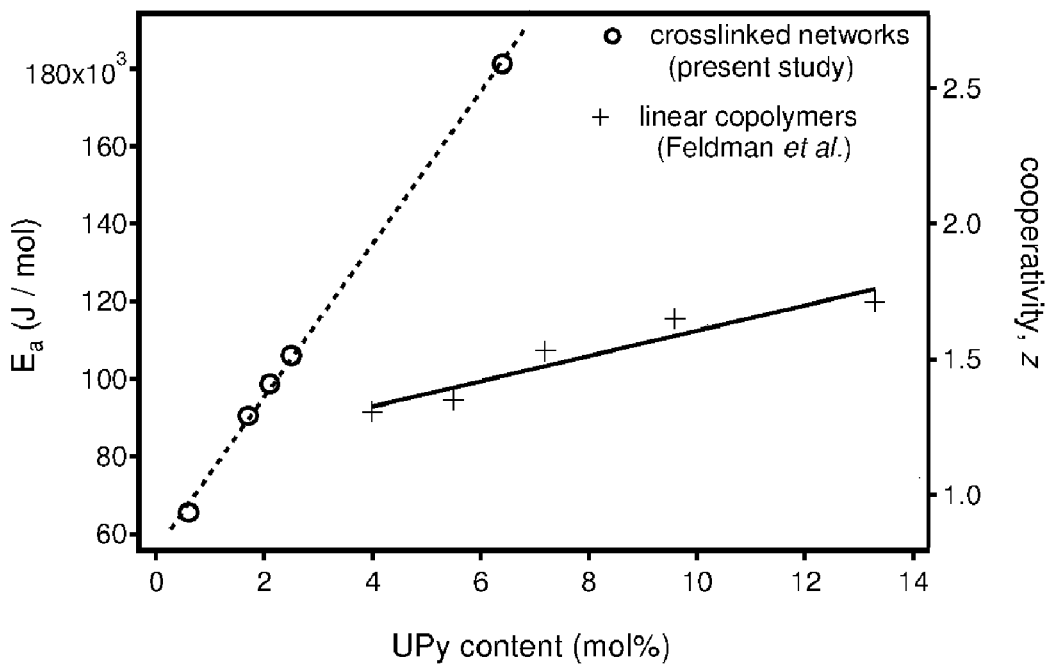
FIG. 18 is a plot of activation energies calculated from storage modulus shift factor versus measured UPy-content in photo-crosslinked elastomers.

The activation energies obtained from least-squares fits to the data in FIG. 17 are plotted versus UPy-content in FIG. 18. The activation energy depends linearly on UPy-content indicating that UPy dissociation dynamics are correlated. As a gauge for interpretation, the activation energy of UPy dissociation in chloroform determined using temperature-dependent NMR Exchange Spectroscopy is 70±2 kJ/mol. The energies in FIG. 18 can be rescaled by this experimental value to yield a cooperativity factor, z (right-hand ordinate) that represents the average-number of cooperative dissociation events required for an incremental loss in stored elastic energy. As a comparison, activation energies of UPy-containing random copolymers are also included in FIG. 18. The comparison shows that the activation energy is more sensitive to UPy-content in crosslinked networks than in linear copolymers. Thus, covalent crosslinking is an effective way to support the cooperative dynamics and bonding of reversibly associating groups.

Example of $^1$H NMR Spectra to Determine Copolymer Composition

Figure 19:
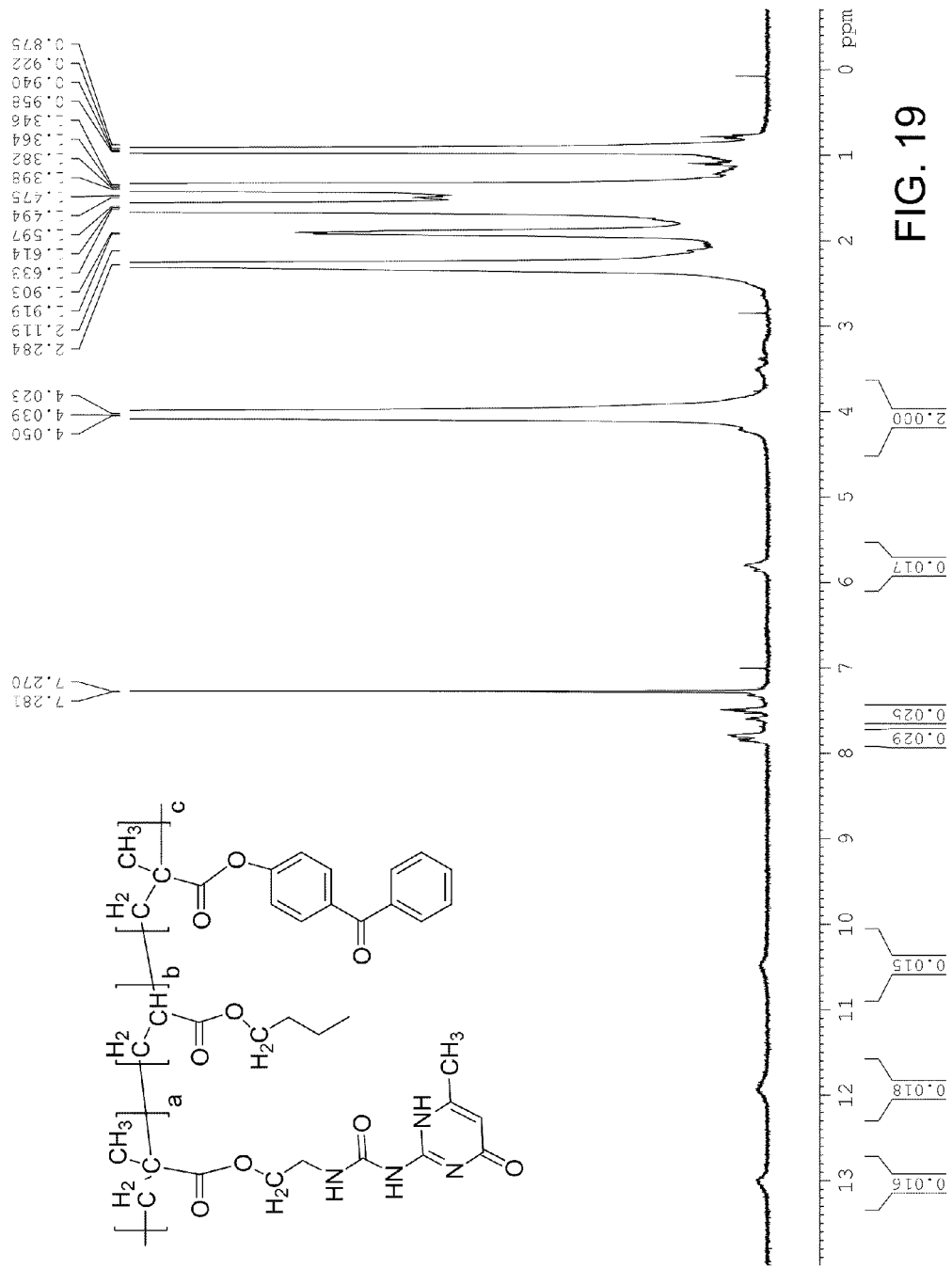
FIG. 19 is a $^1$H NMR spectrum of macromer Bp1-UPy2 in $CDCl_3$.

FIG. 19 shows an example of a macromer NMR spectrum. UPy-content was determined from comparing the UPy group's signature peaks at 5.8 (aromatic CH), 10.5 (NH), 11.9 (NH), 13.0 (NH) ppm to the —OCH$_2$— peak around 4.0 ppm. Likewise, Bp-content was derived using its signature aromatic CH peaks around 7.5 and 7.8 ppm.

Analysis of Volume Swell Data

The classical theory of polymer swelling is often viewed in the context of the Flory-Rehner equation (Flory, P. J. and Rehner, J., Journal Chem. Phy., 1943), which suggests that the degree to which a polymer swells in a solvent depends on the net energy resulting from the competition between the entropy of mixing, which favors swelling, and the enthalpy of mixing and reduction in configuration entropy, both of which oppose swelling. Mathematically, this is expressed as follows:

$$-[\ln(1-v_2) + v_2 + \chi_1 v_2^2] = v_1 n \left[ v_2^{\frac{1}{3}} - \frac{v_2}{2} \right]$$

where $v_1$ is the molar volume of the solvent, $v_2$ is the volume fractions of the polymer, $\chi_1$ is the polymer-solvent interaction parameter, and n is the number of strands in tension (molar basis) per unit volume.

Figure 20:
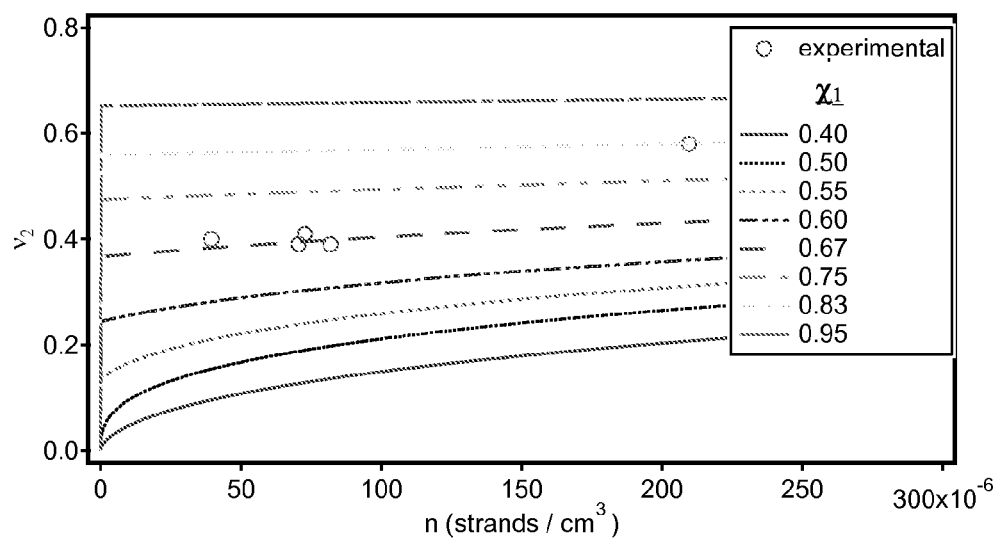
FIG. 20 a graph of volume fraction of polymer ($v_2$) as a function of strand density (n). Experimental data are compared to solution to the Flory-Rehner equation for various values of polymer-solvent interaction parameter ($\chi_1$).

Solutions to the Flory-Rehner equation are plotted as a function of n for various values of $\chi_1$ in FIG. 20. Experimental values of $v_2$, arising from permanent crosslinks, are also included in the figure. The majority of samples fall on a line corresponding to $\chi_1 \approx 0.67$ in the Flory-Rehner equation.

However, the volume swell of Bp2-UPy2 corresponds to a somewhat higher value of the interaction parameter ($\chi_1 \approx 0.83$).

Linear PBA Degradation Study

Figure 21:
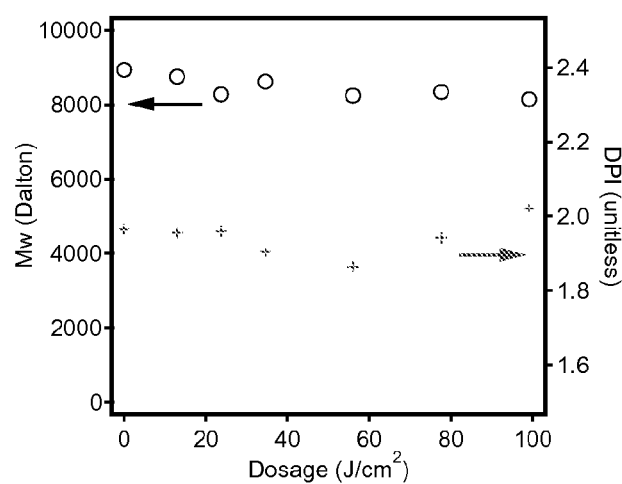
FIG. 21 is an example of the influence of cumulative UV irradiation on weight average molecular weight and polydispersity index (DPI).
Figure 22:
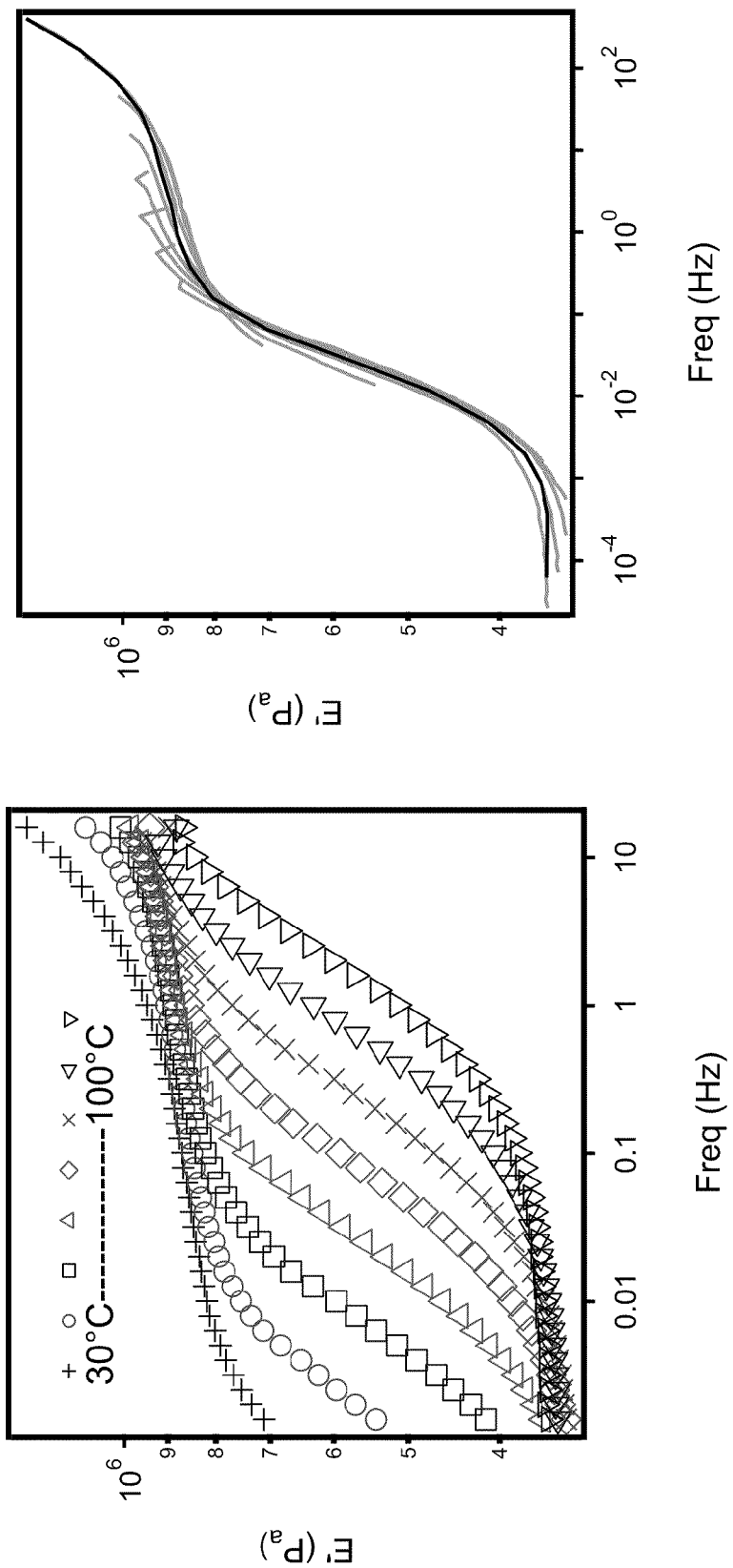
FIG. 22 is a graph of TTS of storage modulus for elastomer Bp½-UPy2.
Figure 23:
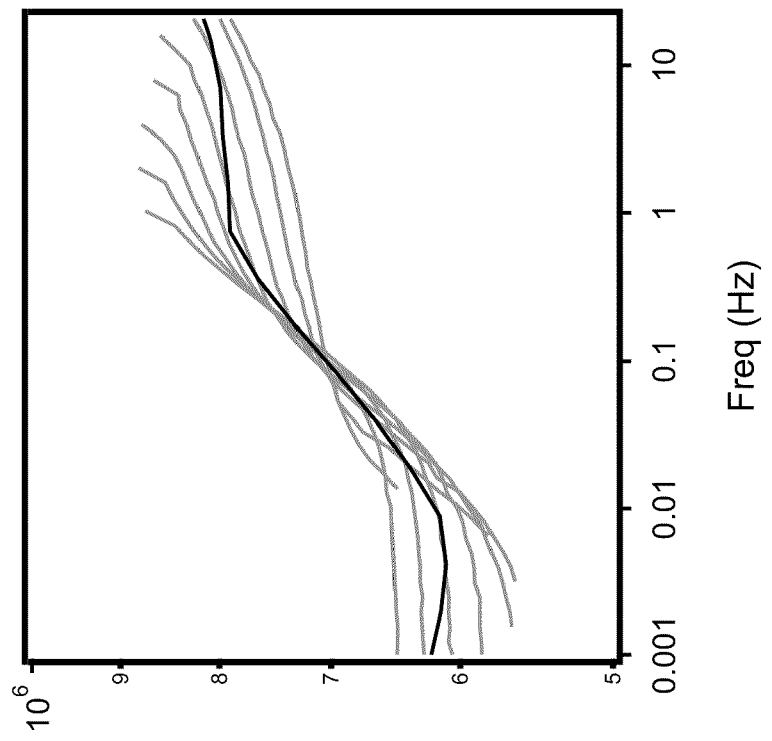
FIG. 23 is a graph of TTS of storage modulus for elastomer Bp1-UPy1.
Figure 23:
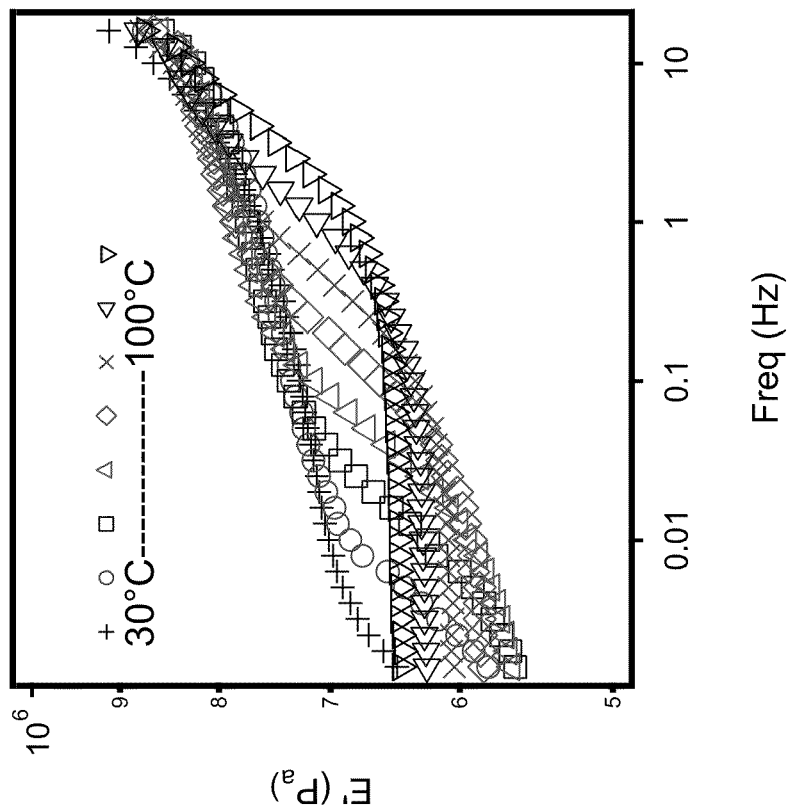
Figure 24:
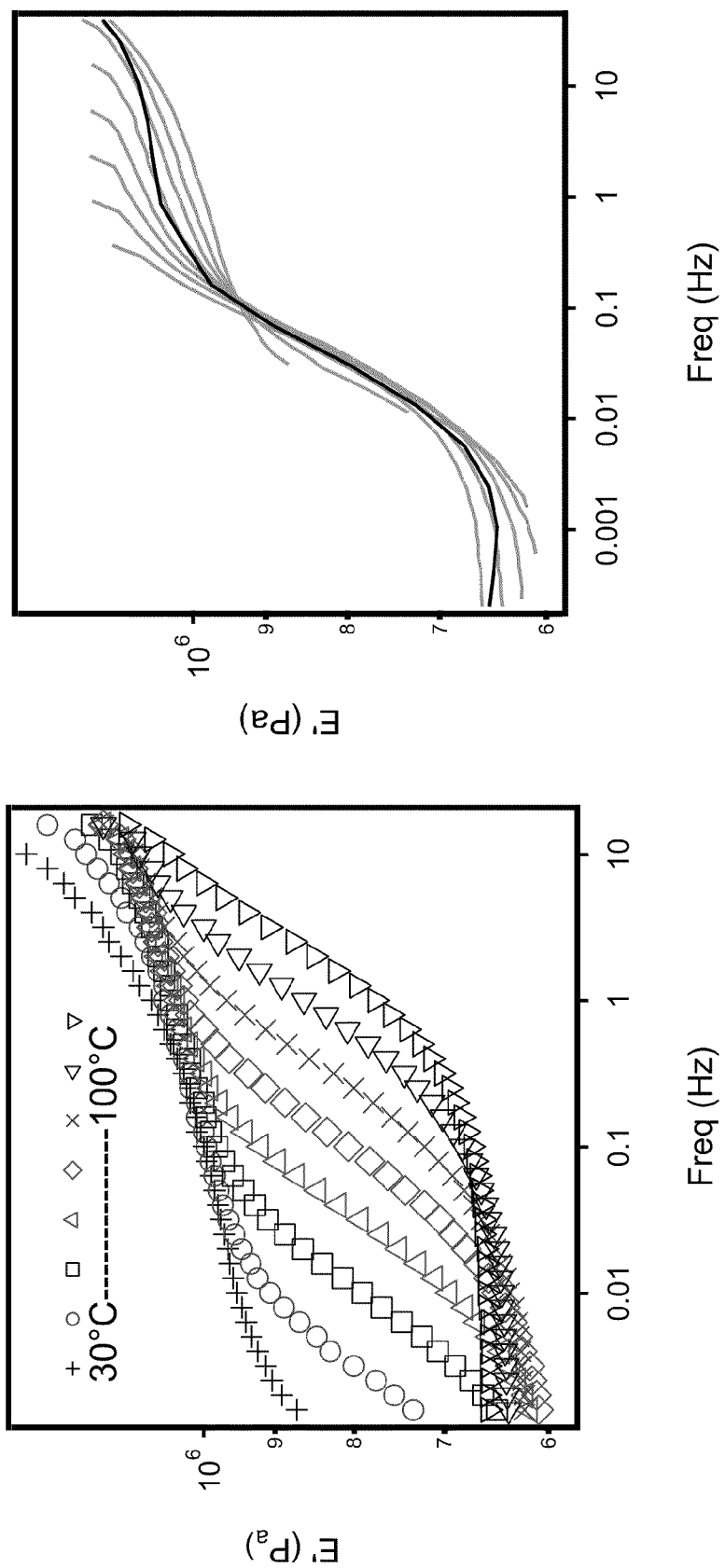
FIG. 24 is a graph of TTS of storage modulus for elastomer Bp1-UPy2.
Figure 25:
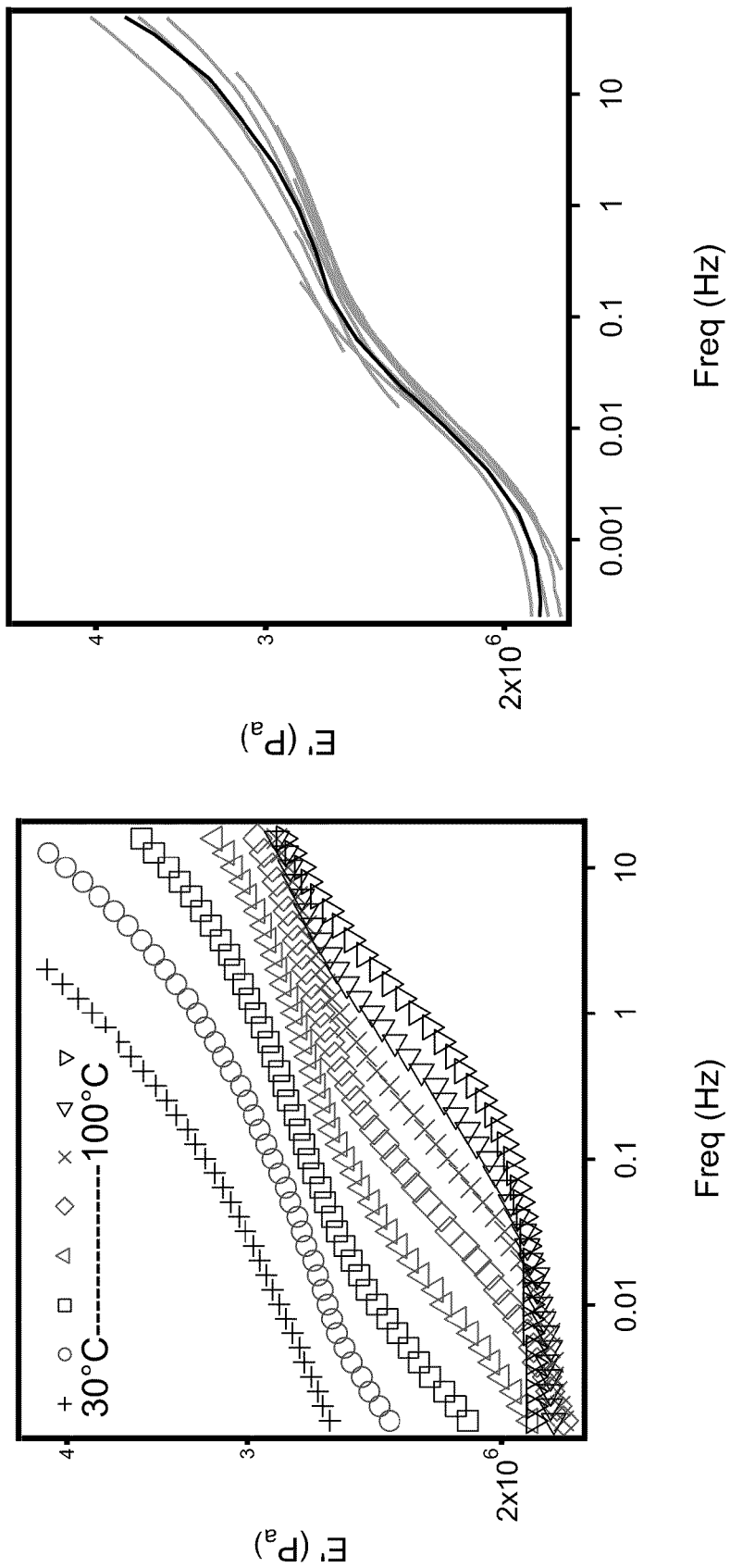
FIG. 25 is a graph of TTS of storage modulus for elastomer Bp2-UPy2.
Figure 26:
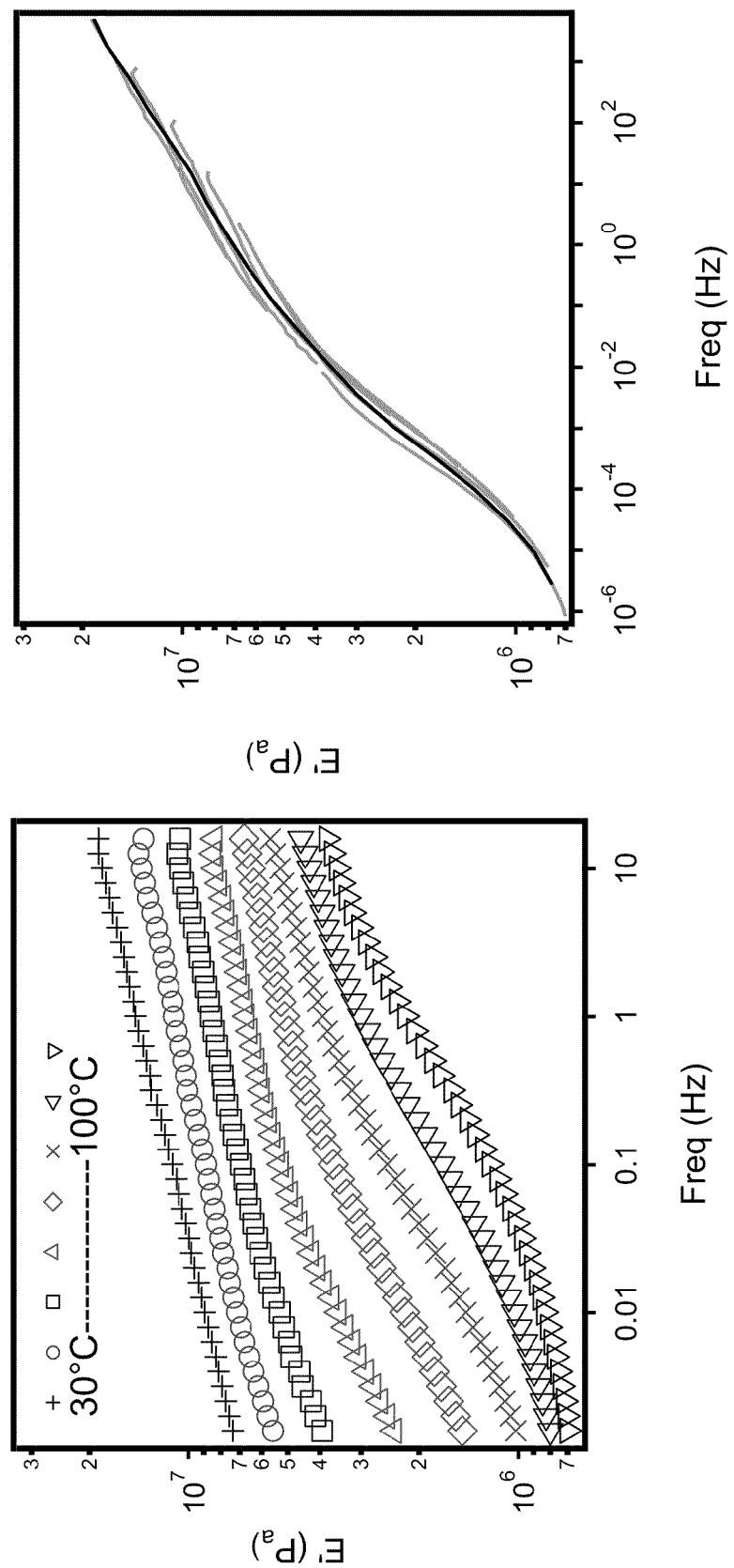
FIG. 26 is a graph of TTS of storage modulus for elastomer Bp1-UPy5.

A study was conducted to determine whether the UV irradiation procedure resulted in degradation of linear macromers. Poly(butyl acrylate) (PBA) homopolymers were prepared in a manner consistent with that used to produce copolymer samples (see experimental section). Disc-shaped samples, 11 mm in diameter and 2.3 mm thick, were solvent-cast (i.e. 150 mg PBA/ml THF) stage wise into glass vials followed by vacuum drying. UV Irradiation was conducted using a Spectroline 400 (400 W lamp with 320-400 nm spectral distribution). The source-to-sample distance was altered in order to achieve a flux of 18.0+/−1.5 mJ/cm$^2$ at 365 nm (measured through the top of the glass cylinder using a hand-held radiometer). Specimens were placed in an evacuated glass cylinder that was subsequently filled with argon gas (3×). Samples were then exposed for a specified period of time. Following each exposure, the vessel was removed from the UV source, the glass chamber opened up, and a sample removed. The glass chamber was resealed and evacuated as described above and placed back into the chamber for continued irradiation. This process was repeated for several time intervals. Sample molecular weight and polydispersity were measured using GPC (measured in THF) as a function of total dosage, and the results are presented in FIG. 21. These data indicate the UV procedure employed does not induce appreciable polymer degradation. Note also that exposure times in FIG. 21 greatly exceed those used in the manuscript.

Time-Temperature Superposition (TTS) to Obtain Storage Modulus Master Curves

TTS enables properties measured over a range of temperatures and frequencies to be shifted to represent a wider range of frequencies for a single temperature. Typically, this is done by graphing the viscoelastic data taken at many different temperatures versus frequency or time on one log-scale plot. Each curve at a different temperature is then shifted horizontally by a shift factor $a_T$ along the frequency axis until it overlaps with the curve at an arbitrary reference temperature. The end result of this process is a single curve that represents viscoelastic behavior of the polymer versus frequency or time at the chosen reference temperature, over a much wider range of frequencies than originally measured. Master curves of different samples at the same reference temperature can then be compared to each other. A program was written (Igor Pro, 6.2) that employed a non-linear regression routine to yield shift-factors for each of the provided temperature curves. FIG. 22-26 show storage modulus DMA data and the corresponding master curves for different photo-crosslinked elastomers. Plots on the left are raw data (frequency sweeps) from the DMA measurements repeated in at 10° C. integrals from 30° C. to 100° C. Plots on the right are the resulting TTS shifted data where the bold solid curves are master curves.

Conclusions

A photo-crosslinking approach to preparing shape-memory elastomers bearing reversibly associating groups was demonstrated. Unlike solution-based approaches, photo-crosslinking is advantageous because: (i) macromer precursors can be thoroughly characterized using NMR and SEC techniques; (ii) the crosslinking process is solventless—avoiding stress accumulation that arises from solvent removal steps; (iii) a much greater fraction of H-bonding side-groups can be achieved due to favorable solubility of the macromer, and (iv) the technique provides the ability to tune the number density of both permanent and reversible crosslinks. Synthesis involved conventional free radical co-polymerization of butyl acrylate, a monomer containing a photoreactive coumarin or benzophenone group, and a monomer containing the UPy side-group. Benzophenone-containing macromers are readily crosslinked upon UV exposure, and 500 micron-thick films were nearly completely crosslinked. Coumarin-containing macromers could only be crosslinked to form thin elastomer films (~30 um) because coumarin's high extinction coefficient the majority of irradiation was absorbed near the surface. Upon exposure of thin coumarin-containing crosslinked films to higher energy (254 nm) UV light, partial (~60%) photo-cleavage of coumarin dimers was observed.

To understand how network architecture and reversible binding affects mechanical properties, photo-crosslinked elastomers containing benzophenone side-groups were prepared with varying number density of permanent and dynamic crosslinks. Dynamic mechanical analysis revealed two plateaus in the storage modulus master curves. A high-temperature plateau was attributed only to the permanent network, and the low-temperature plateau was attributed to both permanent and reversible crosslinks. Moreover, a maximum in the loss tangent was observed that depends strongly on the UPy content. Higher UPy contents, and lower Bp contents, increased the magnitude of the damping (tan δ) peak, while also enhancing the materials stiffness. Activation energies could be calculated from the temperature-dependence of shift factors obtained from time-temperature superposition of storage modulus curves. The activation energy was found to increase with UPy content, and this is consistent with cooperative dynamics of UPy binding. Finally, by comparing measured activation energies to those of linear UPy-containing polymers, the UPy binding effectiveness is clearly enhanced by covalent crosslinks. Thus, in addition to providing mechanical support, covalent networks may be engineered to reinforce internal, complementary binding, and this idea may open new approaches to engineering shape-memory, self-healing, and other stimuli-responsive materials.

While the invention has been particularly shown and described with reference to specific embodiments (some of which are preferred embodiments), it should be understood by those having skill in the art that various changes in form and detail may be made therein without departing from the spirit and scope of the present invention as disclosed herein.

What is claimed is:

1. A polymer having the formula:

comprising:
a) hydrogen bonding units, HB, having at least one hydrogen bond donor moiety and at least one hydrogen bond acceptor moiety;
b) backbone modifier units, MOD; and
c) photochemical crosslinking units, PXL, that are capable of reversibly forming one or more crosslinks as a result of photochemical reactions;

the indices x, y, and z represent the mole fraction of each unit, the index x is from 0.1 to 40, the index y is from 0.5 to 99.8, and the index z is from 0.1 to 20.

2. The polymer of claim 1, wherein the HB unit has the formula:

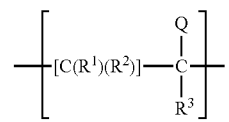

wherein each $R^1$ and $R^2$ is independently chosen from: hydrogen; $C_1$-$C_6$ alkyl, halogen; cyano; phenyl;

wherein $R^3$ is chosen from hydrogen, $C_1$-$C_6$ alkyl;

wherein Q is a unit having at least one hydrogen bond donor moiety or at least one hydrogen bond acceptor moiety; and.

3. The polymer of claim 2, wherein Q has the formula:

-[L]$_i$-R$^4$ wherein when the index i is equal to 1, the linking group L is present, when the index i is equal to 0 the linking unit is absent;

L is a linking unit having the formula:

—[W]$_h$—[Y]$_j$—[Z]$_k$— and Z are each independently chosen from —C(O)—; —C(O)O—; —OC(O)—, —NH—; —C(O)NH—; —NHC(O)—; —NHC(O)NH—; —NHC(=NH)NH— and —O—;

the indices h and k are independently equal to 0 or 1; when h is 0 the W unit is absent, when h is 1 the W unit is present; when k is 0 the W unit is absent, when k is 1 the W unit is present;

Y is a unit having one or more units chosen from —(CR$^{5a}$R$^{5b}$)$_s$—; —[(CR$^{5a}$R$^{5b}$)$_v$(CR$^{5a'}$R$^{5b'}$)$_u$]$_w$—; —[(CR$^{5a}$R$^{5b}$)$_t$O]$_w$—; and —[(CR$^{5a}$R$^{5b}$)$_t$O]$_w$(CR$^{5a}$R$^{5b}$)$_s$—;

each $R^{5a}$ and $R^{5b}$ is independently chosen from hydrogen and $C_1$-$C_4$ alkyl;

$R^{5a'}$ and $R^{5b'}$ are each independently $C_1$-$C_4$ alkyl;

the index j is 0 or 1;

when j is equal to 0 the Y unit is absent, when j is equal to 1 the Y unit is present;

the index s is from 0 to 10, the index t is from 2 to 10, the index u is from 1 to 10, the index v is from 1 to 10, the index w is from 1 to 10;

$R^4$ is a unit chosen from hydrogen; a substituted carbocyclic ring; a substituted aryl ring; a substituted or unsubstituted heterocyclic ring; and a substituted or unsubstituted heteroaryl ring; the substitution is a moiety capable of being a hydrogen bond donor or a hydrogen bond acceptor.

4. The polymer of claim 3, wherein the $R^4$ unit is a $C_3$, $C_4$ or $C_5$ heterocyclic or heteroaryl ring substituted with one or more units chosen from: $C_1$-$C_4$ linear or branched alkyl; —NR$^{6a}$R$^{6b}$; —C(O)OR$^7$; —C(O)R$^7$; —C(O)NR$^{6a}$R$^{6b}$; —NR$^8$C(O)NR$^{6a}$R$^{6b}$; —NR$^8$C(O)R$^7$; and —NR$^{8C}$(=NR$^8$) NR$^{6a}$R$^{6b}$; R$^{6a}$, R$^{6b}$, R$^7$, and R$^8$ are each independently chosen from hydrogen, methyl or ethyl.

5. The polymer of claim 3, wherein $R^4$ is a substituted or unsubstituted $C_3$, $C_4$, $C_5$ or $C_6$ heterocyclic or heteroaryl ring selected from:

a) pyrrolidinyl ring having the formula:

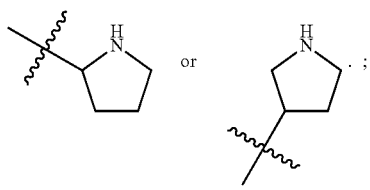

b) a pyrrolyl ring having the formula:

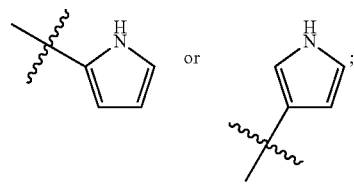

c) a 4,5-dihydroimidazolyl ring having the formula:

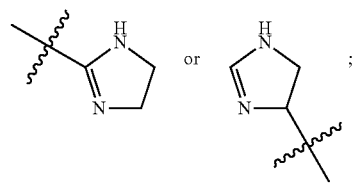

d) an imidazolyl ring having the formula:

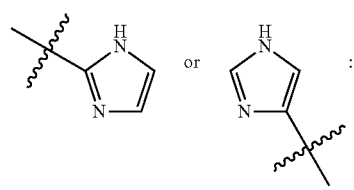

e) a pyrrolidinonyl ring having the formula:

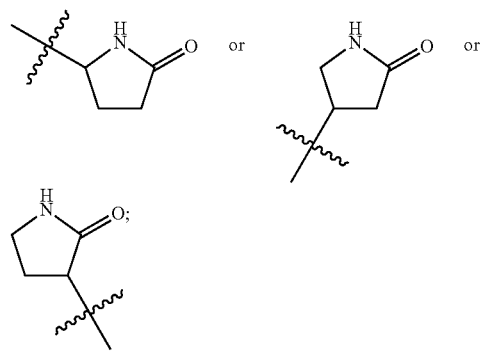

f) an imidazolidinonyl ring having the formula:

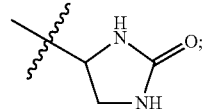

g) an imidazol-2-only ring having the formula:

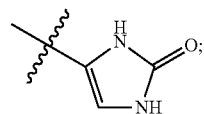

h) an oxazolyl ring having the formula:
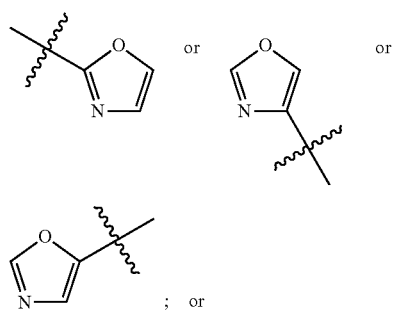
i) a furanly ring having the formula:
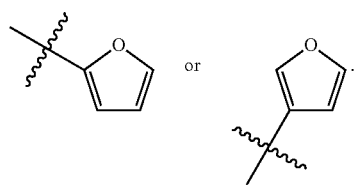
j) a morpholinyl ring having the formula:
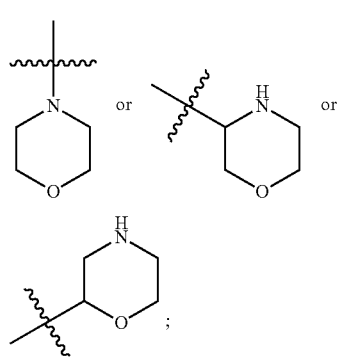
k) a piperidinyl ring having the formula:
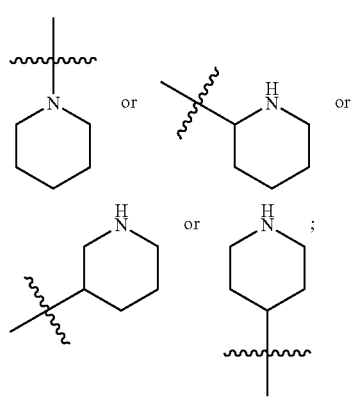
l) a pyridinyl ring having the formula:
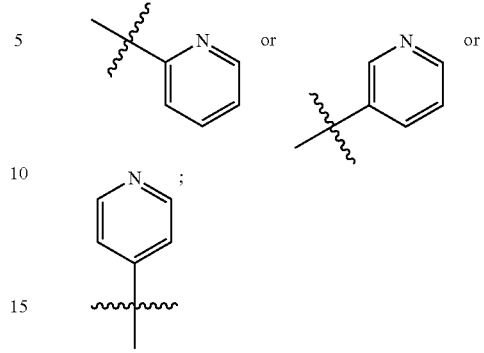
m) a piperazinyl ring having the formula:
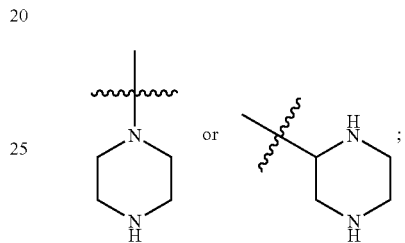
n) a ketopiperazinyl ring having the formula:
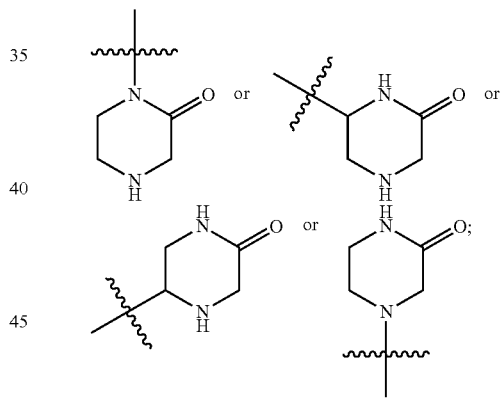
o) a dihydropyrazin2-onyl ring having the formula:
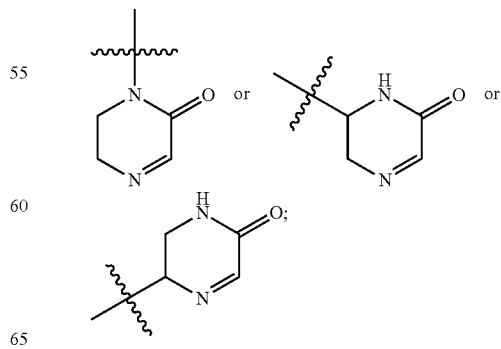

p) a pyrazin2-onyl ring having the formula:
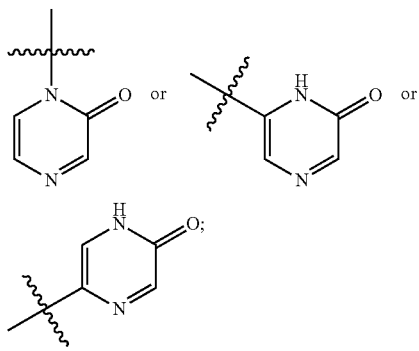
q) dihydropyrimidin-4-onyl having the formula:
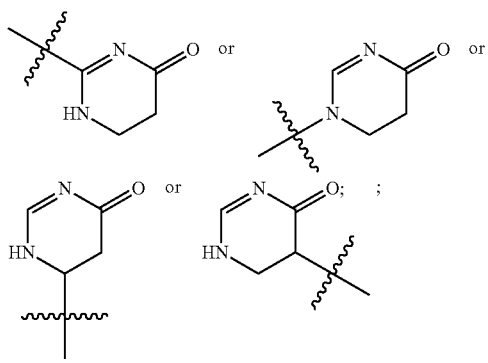
r) a uracil ring having the formula:
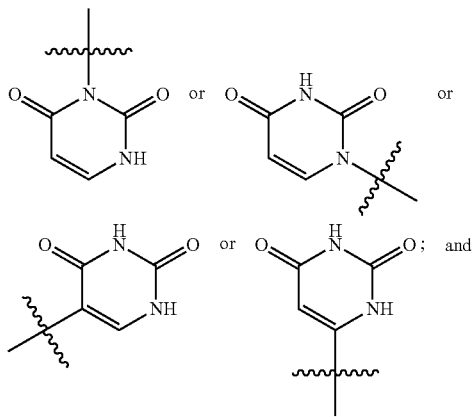
s) a triazinyl ring having the formula:
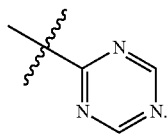
t) purinyl rings having the formula:
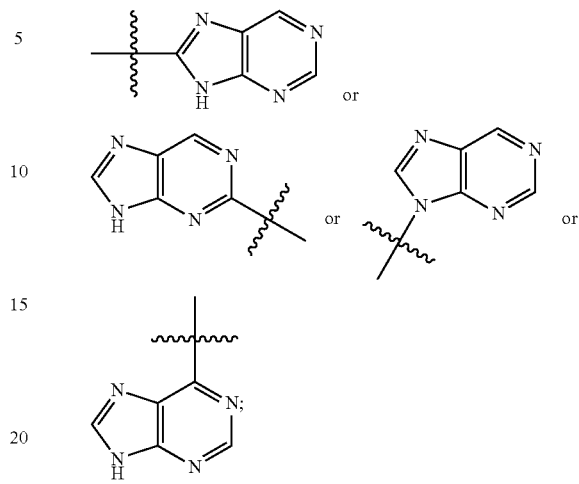
u) amino purinyl rings having the formula:
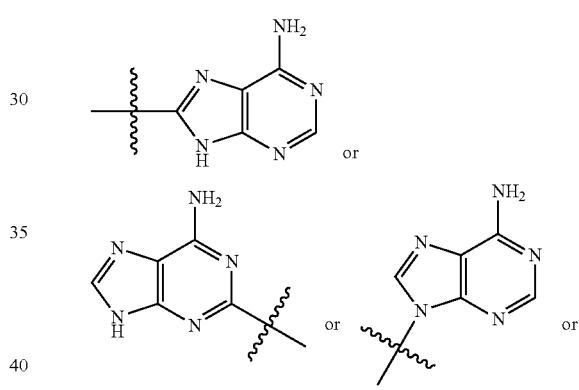
v) aminopurinonyl rings having the formula:
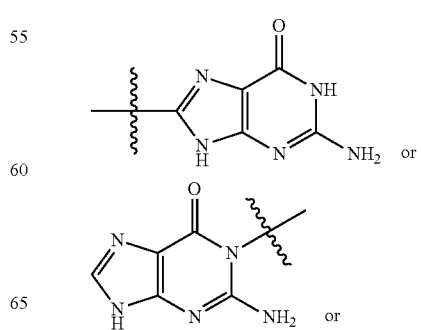

-continued

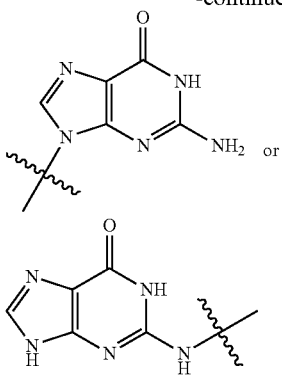

w) pyrrolo[3,2-d]pyrimidinyl rings having the formula:

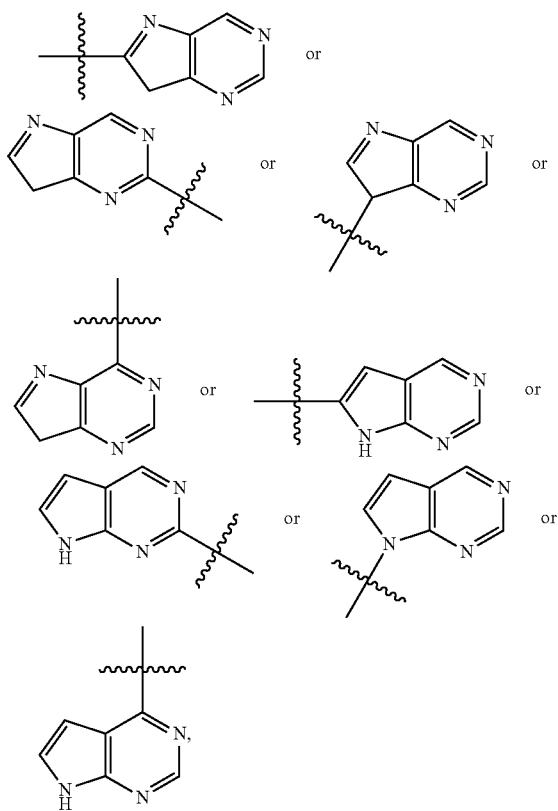

and combinations thereof.

6. The polymer of claim 1, wherein the MOD unit has the formula:

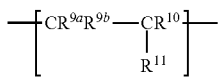

wherein each $R^{9a}$, $R^{9b}$, and $R^{10}$ are independently selected from: hydrogen, $C_1$-$C_4$ alkyl, and $C_5$-$C_6$ aryl;
$R^{11}$ is a unit independently chosen from hydrogen, $C_1$-$C_4$, —$NR^{12a}R^{12b}$, —C(O)$OR^{13}$, —C(O)$R^{13}$, and —C(O)$NR^{12a}R^{12b}$,
wherein $R^{12a}$, $R^{12b}$, and $R^{13}$ are each independently hydrogen or $C_1$-$C_{10}$ alkyl.

7. The polymer of claim 1, wherein the PXL unit has the formula:

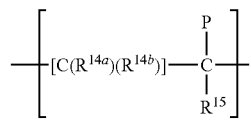

wherein each $R^{14a}$ and $R^{14b}$ is independently chosen from: hydrogen, $C_1$-$C_6$ alkyl, halogen, cyano, and $C_5$-$C_6$ aryl, wherein each $R^{15}$ is independently selected from hydrogen and $C_1$-$C_6$ alkyl;
wherein P is a unit that on exposure to a first wavelength causes formation of an intrachain crosslink or interchain crosslink bond.

8. The polymer of claim 7, wherein the formation of the intrachain or interchain bond is formed by photoreaction of two P units, and exposure of the intrachain or interchain bond to a second wavelength results in breakage of the bond and regeneration of the unexposed P unit state.

9. The polymer of claim 7, wherein P has the formula:

wherein when the index m is equal to 1 the linking group L is present and when the index m is equal to 0 the linking unit is absent;
L is a linking unit having the formula:

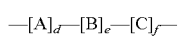

and A are each independently chosen from —C(O)—; —C(O)O—; —OC(O)—, —NH—; —C(O)NH—; —NHC(O)—; —NHC(O)NH—; —NHC(=NH)NH— and —O—;
the indices d and f are independently equal to 0 or 1; when d is 0 the A unit is absent, when f is 1 the A unit is present; when f is 0 the C unit is absent, when f is 1 the C unit is present;
B is a unit having one or more units chosen from —$(CR^{18a}R^{18b})_b$—; —$[(CR^{18a}R^{18b})_c(CR^{18a'}R^{18b'})_d]_e$—; —$[(CR^{18a}R^{18b})_gO]_e$—; and —$[(CR^{18}R^{18b})_gO]_e(CR^{18}R^{18b})_b$—; each $R^{18a}$ and $R^{18b}$ is independently chosen from hydrogen and $C_1$-$C_4$ alkyl;
$R^{18a'}$ and $R^{18b'}$ are each independently $C_1$-$C_4$ alkyl;
the index e is 0 or 1;
when e is equal to 0 the B unit is absent, when e is equal to 1 the B unit is present;
the index b is from 0 to 10, the index g is from 2 to 10, the index d is from 1 to 10, the index c is from 1 to 10, the index e is from 1 to 10;
$R^{17}$ is a unit chosen from hydrogen; a substituted carbocyclic ring; a substituted aryl ring; a substituted or unsubstituted heterocyclic ring; and a substituted or unsubstituted heteroaryl ring; the substitution is a moiety that on exposure to electromagnetic radiation having the appropriate wavelength undergoes chemical reaction with another P unit in sufficient proximity on the same polymer chain or an adjacent polymer chain to form a intrachain or interchain crosslinking bond and, optionally, that on exposure to electromagnetic radiation having the appropriate wavelength undergoes another chemical reaction resulting in the breaking of intrachain or interchain crosslinking bond and return of the P unit to its original chemical structure being a hydrogen bond donor or a hydrogen bond acceptor.

10. The polymer of claim 9, wherein the $R^{17}$ unit is a benzophenone group or a coumarin group having the following structure:

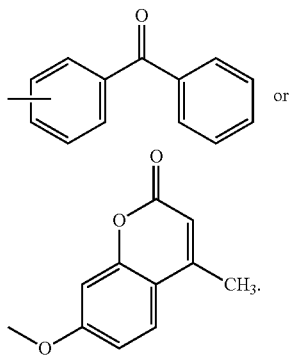 or

11. The polymer of claim 1, wherein PXL is a benzophenone containing group, and wherein the polymer has been exposed to electromagnetic radiation having a wavelength of 365 nm such that at least two benzophenone groups on the same chain or different chains have reacted to form an intrachain crosslink or interchain crosslink bond.

12. The polymer of claim 1, wherein the polymer is characterized by having a shape memory temperature, $T_{SM}$, such that the polymer can be elastically deformed at the shape memory temperature, and subsequently lowered to a shape memory freezing temperature, $T_F$, and the method of elastic deformation is removed, the polymer will return to its original shape with a rate slower than the rate observed if the method of mechanical elastic deformation were removed at $T_{SM}$, provided the shape memory freezing temperature $T_F$ is above the glass transition, $T_G$, of the polymer, and provided the polymer is in the amorphous state at $T_F$.

13. The polymer of claim 1, wherein when the polymer is elastically deformed at a shape memory temperature $T_{SM}$ and subsequently lowered to a shape memory temperature, $T_F$, and the method by which the polymer is elastically deformation is removed, the polymer returns to its original shape at an overall recovery rate, $R_{REC}$, and wherein further the recovery rate is inversely related to the difference in the temperature, $\Delta \cdot T_{DEF}$, wherein $\Delta \cdot T_{DEF} = T_{SM} - T_F$.

14. The polymer of claim 13, wherein the overall $R_{REC}$ is from about 0.001%/minute to about 100%/second.

15. The polymer of claim 14, wherein the overall recovery rate includes a variable recovery rate over at least 10% of the recovery rate that is from about 0.001%/minute to about 5%/minute.

16. A device comprising one or more polymers of claim 1.

17. The device of claim 16, wherein the device is a medical device, a hearing safety device or data storage device.

18. The medical device of claim 17, chosen from stents, sutures, vascular compresses, and vascular clips.

19. The hearing safety device of claim 17, wherein the device is an ear plug.

* * * * *

UNITED STATES PATENT AND TRADEMARK OFFICE
CERTIFICATE OF CORRECTION

PATENT NO. : 8,172,873 B2  
APPLICATION NO. : 13/047354  
DATED : May 8, 2012  
INVENTOR(S) : Anthamatten et al.

Page 1 of 1

It is certified that error appears in the above-identified patent and that said Letters Patent is hereby corrected as shown below:

In the claims:

Column 73, line 6, "moiety; and." should read --moiety.--.

Signed and Sealed this
Fourteenth Day of August, 2012

David J. Kappos
*Director of the United States Patent and Trademark Office*